(12) United States Patent
Keller

(10) Patent No.: US 11,596,548 B2
(45) Date of Patent: *Mar. 7, 2023

(54) DEVICE FOR AUTOMATED CAPSULOTOMY

(71) Applicant: Centricity Vision, Inc., Fremont, CA (US)

(72) Inventor: Christopher Guild Keller, El Cerrito, CA (US)

(73) Assignee: CENTRICITY VISION, INC., Carlsbad, CA (US)

(*) Notice: Subject to any disclaimer, the term of this patent is extended or adjusted under 35 U.S.C. 154(b) by 378 days.

This patent is subject to a terminal disclaimer.

(21) Appl. No.: 16/440,999

(22) Filed: Jun. 14, 2019

(65) Prior Publication Data

US 2019/0380872 A1 Dec. 19, 2019

Related U.S. Application Data

(63) Continuation of application No. 14/423,928, filed as application No. PCT/US2013/060988 on Sep. 20, 2013, now Pat. No. 10,363,167.

(Continued)

(51) Int. Cl.
*A61B 18/14* (2006.01)
*A61F 9/007* (2006.01)
(Continued)

(52) U.S. Cl.
CPC ........ *A61F 9/00754* (2013.01); *A61B 18/082* (2013.01); *A61B 2018/00107* (2013.01);
(Continued)

(58) Field of Classification Search
CPC .. A61F 9/00754; A61F 9/0079; A61B 18/082; A61B 2018/00601;
(Continued)

(56) References Cited

U.S. PATENT DOCUMENTS 3,768,482 A 10/1973 Shaw
5,030,218 A 7/1991 Alexander
(Continued)

FOREIGN PATENT DOCUMENTS

CN 101557769 A 10/2009
CN 102026600 A 4/2011
(Continued)

OTHER PUBLICATIONS

Chinese First Office Action, Chinese Application No. 201380058138.0, dated Jul. 29, 2016, 14 pages.
(Continued)

*Primary Examiner* — Jaymi E Della
(74) *Attorney, Agent, or Firm* — Fenwick & West LLP

(57) ABSTRACT

A surgical device is disclosed for cutting tissue, including for performing a capsulotomy of a lens capsule of an eye. This device includes a reversibly collapsible cutting element for cutting a portion of a capsule membrane of the eye. The cutting element includes an outer layer, an inner layer, and a bottom layer that has a higher electrical resistance than the electrical resistance of the outer layer and the inner layer. The bottom layer is configured to conduct an electrical current between the outer layer and the inner layer, which causes a temperature increase in the bottom layer for cutting tissue.

18 Claims, 49 Drawing Sheets

Related U.S. Application Data

(60) Provisional application No. 61/703,514, filed on Sep. 20, 2012.

(51) Int. Cl.
  *A61B 18/08* (2006.01)
  *A61B 18/00* (2006.01)

(52) U.S. Cl.
  CPC ............... *A61B 2018/00321* (2013.01); *A61B 2018/00601* (2013.01); *A61F 9/0079* (2013.01)

(58) Field of Classification Search
  CPC .. A61B 2018/1407; A61B 2018/00107; A61B 2018/00321; A61B 2018/00327; A61B 2018/00607
  See application file for complete search history.

(56) References Cited

U.S. PATENT DOCUMENTS

| | | | |
|---|---|---|---|
| 5,486,183 A * | 1/1996 | Middleman | A61B 17/0469 606/127 |
| 5,603,711 A * | 2/1997 | Parins | A61B 10/06 606/51 |
| 7,785,321 B2 | 8/2010 | Baerveldt et al. | |
| 7,967,855 B2 | 6/2011 | Furst et al. | |
| 8,137,344 B2 | 3/2012 | Jia et al. | |
| 8,142,425 B2 | 3/2012 | Eggers | |
| 8,162,931 B2 | 4/2012 | Ben-Nun | |
| 8,235,978 B2 | 8/2012 | Ben-Nun | |
| 8,657,813 B2 | 2/2014 | Ben-Nun et al. | |
| 8,702,698 B2 | 4/2014 | Keller | |
| 2002/0161365 A1 | 10/2002 | Martins | |
| 2004/0260254 A1 | 12/2004 | Neilson et al. | |
| 2005/0165346 A1 | 7/2005 | Neilson et al. | |
| 2006/0217706 A1 | 9/2006 | Lau et al. | |
| 2007/0191862 A1 | 8/2007 | Ellis | |
| 2007/0287999 A1 | 12/2007 | Malecki et al. | |
| 2009/0112200 A1 | 4/2009 | Eggers | |
| 2010/0094278 A1 | 4/2010 | Jia et al. | |
| 2010/0179544 A1 * | 7/2010 | Boukhny | A61F 9/00754 606/48 |
| 2011/0071524 A1 * | 3/2011 | Keller | A61B 18/085 606/45 |
| 2011/0213359 A1 * | 9/2011 | Ben-Nun | A61B 18/082 606/39 |
| 2013/0197548 A1 | 8/2013 | Keller | |
| 2014/0074088 A1 | 3/2014 | Ben Nun et al. | |
| 2014/0207137 A1 | 7/2014 | Keller | |

FOREIGN PATENT DOCUMENTS

| | | |
|---|---|---|
| CN | 102271606 A | 12/2011 |
| JP | S5233438 B2 | 8/1997 |
| JP | 2008-534068 A | 8/2008 |
| JP | 2012-515017 A | 7/2012 |
| WO | WO 2009/140414 A1 | 11/2009 |
| WO | WO 2011/155922 A1 | 12/2011 |

OTHER PUBLICATIONS

Chinese Second Office Action, Chinese Application No. 201380058138.0, dated Jun. 5, 2017, 7 pages.
European Extended Search Report, European Application No. 13838217.1, dated Jun. 6, 2016, 6 pages.
Japanese Office Action, Japanese Application No. 2015-533229, dated Jun. 6, 2017, 8 pages.
Japanese Second Office Action, Japanese Application No. 2015-533229, dated Jun. 5, 2018, 9 pages.
Patent Cooperation Treaty, International Search Report and Written Opinion, International Patent Application No. PCT/US2013/060988, dated Feb. 21, 2014, 15 Pages.
United States Office Action, U.S. Appl. No. 14/423,928, filed Oct. 10, 2018, 14 pages.
United States Office Action, U.S. Appl. No. 14/423,928, filed Nov. 16, 2017, 11 pages.
United States Office Action, U.S. Appl. No. 14/423,928, filed May 24, 2017, 13 pages.
Japan Patent Office, Japanese Application No. 2018-227545, Office Action, dated Dec. 3, 2019, 5 pages.

* cited by examiner

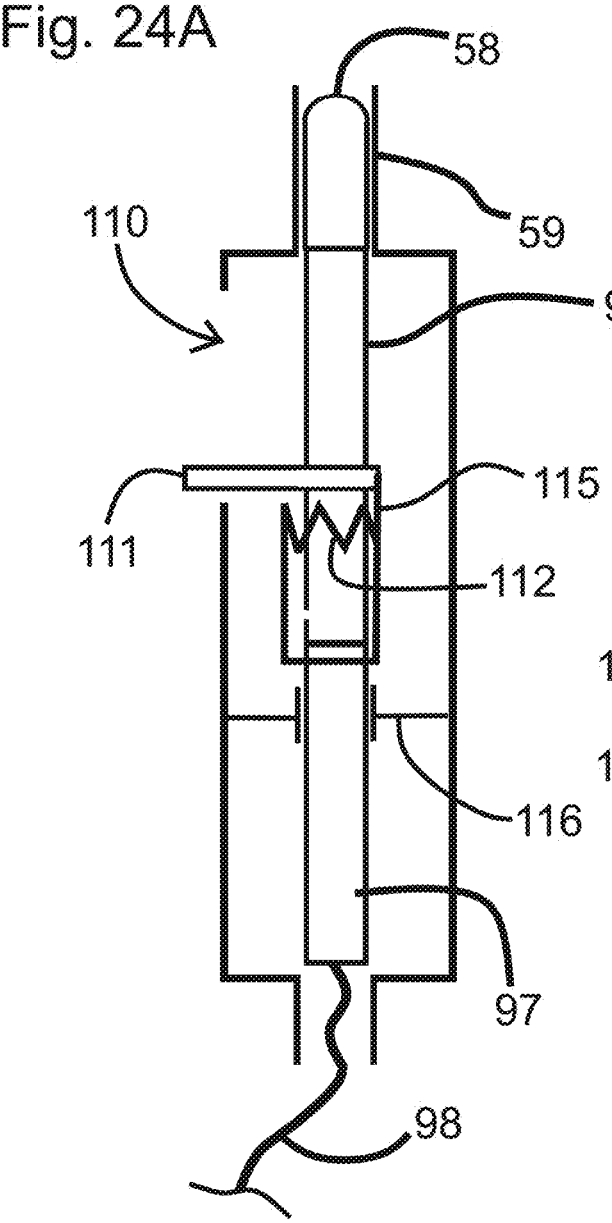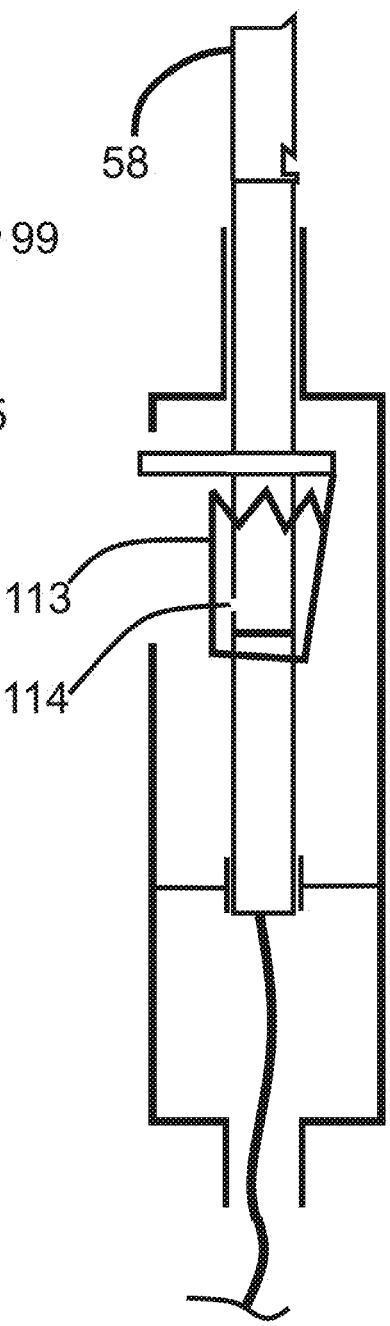

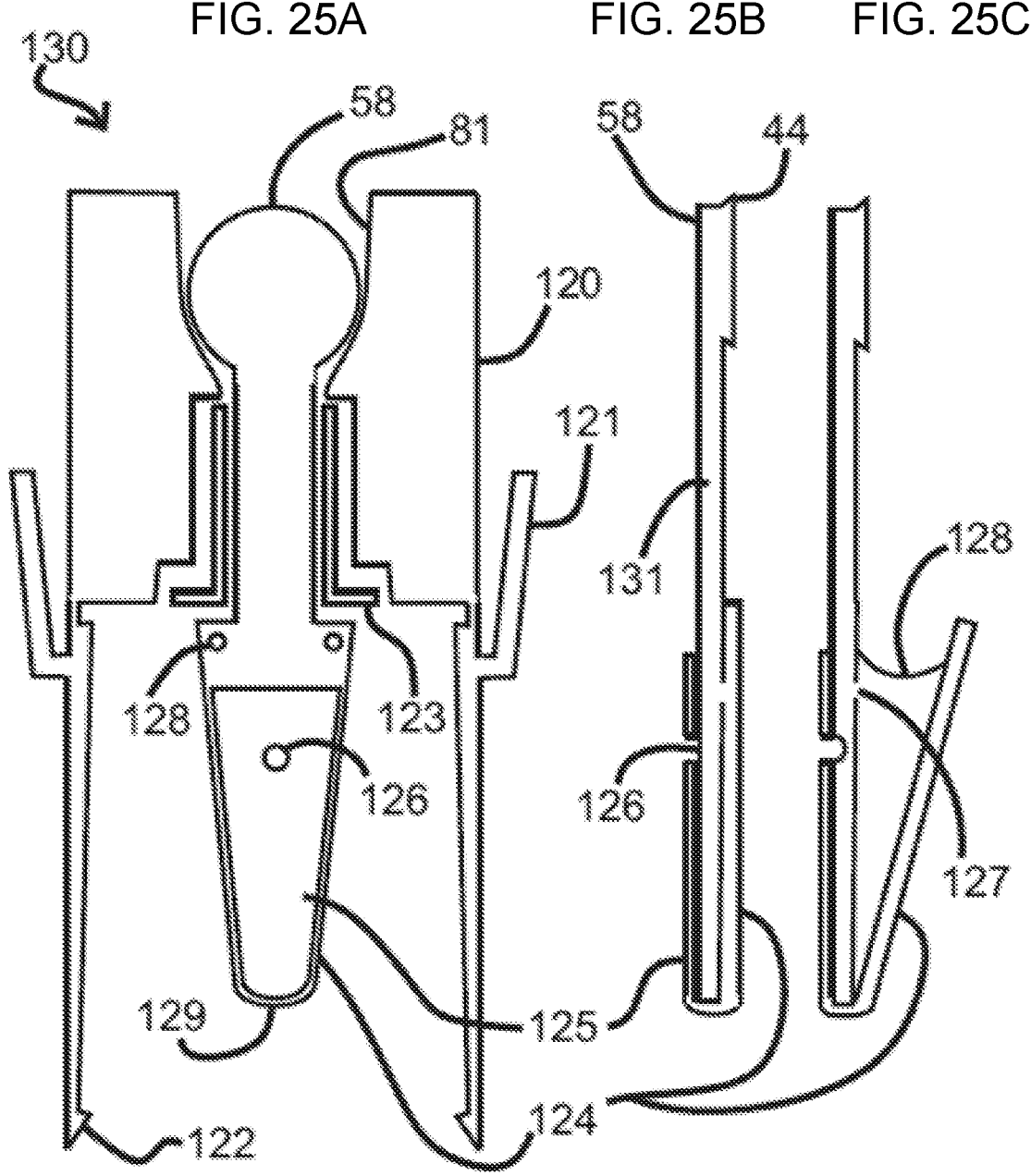

DEVICE FOR AUTOMATED CAPSULOTOMY

CROSS-REFERENCE TO RELATED APPLICATIONS

This application is a continuation of U.S. application Ser. No. 14/423,928, which has a 371 date of Feb. 25, 2015, now U.S. Pat. No. 10,363,167, which is a national stage entry of International Application No.: PCT/US2013/060988 filed Sep. 20, 2013, which claims priority to U.S. Provisional Application No. 61/703,514, filed Sep. 20, 2012, all of the foregoing are incorporated herein by reference in their entirety.

STATEMENT REGARDING FEDERALLY SPONSORED RESEARCH OR DEVELOPMENT

This invention was made with government support under Grant Numbers 3R44EY021023-03S1, 5R44EY021023-03, 2R44EY021023-04, and 2R44EY021023-02, awarded by the National Institutes of Health. The government has certain rights in the invention.

BACKGROUND

Technical Field

This disclosure relates to devices and methods for performing a capsulotomy, and more specifically, devices and methods for using an electrical cutting element to cut a membrane of the eye during a capsulotomy.

Description of the Related Art

Lens cataract is the leading cause of blindness worldwide and surgical treatment by cataract removal is the treatment of choice. If the lens of an eye develops opaque areas, as in a cataract, the lens must be surgically removed. The lens can be replaced with an artificial intraocular lens (IOL) to provide better vision after cataract removal. There may also be other reasons such as presbyopia to replace a lens that is not serving its functions appropriately.

The removal of the lens for replacement with an IOL is a surgical procedure that requires substantial precision. The lens is completely enclosed by a membrane called the lens capsule, so the surgeon must first cut through the capsule to access the lens. Creating an opening in the lens capsule with the required level of precision is a difficult task for a surgeon controlling and guiding conventional handheld cutting instruments and attempting to trace a precise circular route on the lens capsule. Currently, to perform a capsulotomy (the creation of an opening in the lens capsule), the surgeon typically manually creates a small tear in the anterior region of the lens capsule, and uses a small forceps to try to extend the edge of the tear so as to follow a circular path of the specified diameter and centered on the optic axis of the eye. In practice, it often happens that the hole does not end up circular, or the correct diameter, or centered on the optic axis. There can also be radial tears in the edge of the hole that greatly weaken the capsule. As a result of any of these errors, the capsule may not be able to hold the IOL properly, and optimal visual outcome cannot be achieved.

Microsurgery instruments commonly are not sufficiently compact or streamlined in shape, making it difficult for a surgeon to minimize the incision size or possibly risking tears or other damage at the incision site. Cutting elements or other sharp components are sometimes exposed during insertion, requiring the surgeon to be very precise and creating further risk of collateral damage to tissue when inserting the instrument through the incision. Further, this insertion often requires multiple steps and sometimes complex maneuvering of instruments by the surgeon, leaving little room for error. Once inserted, instruments are often not easily manipulated and the surgeon may be forced to handle and move multiple separate pieces in a small space. Any of these problems can make it very difficult for a surgeon to access a second layer of tissue behind a first layer, particularly when the second layer is tissue in a very small area, such as within the eye.

Given the drawbacks of existing treatment devices/procedures for accessing tissue, such as the lens capsule, to perform surgery, improved techniques and devices for performing microsurgery and capsulotomy are needed.

SUMMARY

This invention provides a surgical device for cutting tissue. The device includes a reversibly collapsible supporting element and a reversibly collapsible cutting element that is attached to the supporting element. The cutting element includes electrically conductive outer and inner layers on the outer and inner diameters (respectively) of the supporting element, as well as a bottom layer on the bottom edge of the supporting element. The bottom layer is associated with the outer and inner layers, but the bottom layer has a higher electrical resistance than that of the outer and inner layers. The bottom layer can conduct an electrical current between the outer and inner layers, causing a temperature increase in the bottom layer for cutting tissue. In an embodiment, the device is a capsulotomy device for performing a capsulotomy on a lens capsule of an eye.

In one embodiment, the cutting element is circular. In another embodiment, a suction cup is attached to the supporting element. In another embodiment, the bottom layer has a thickness of 10-200 angstroms, and is thinner than the inner and outer layers. In still another embodiment, the supporting element has a thickness of 25-50 microns where the supporting element is between the outer and inner layers. In another embodiment, the device can conduct the electrical current as a single electrical current pulse, or a series of electrical current pulses.

In an embodiment, the outer layer of the device is coupled to a lead, which conducts electrical current to the outer layer and the bottom layer. The inner layer is also coupled to a lead, and the inner layer can conduct electrical current from the bottom layer to this lead. In another embodiment, the supporting element is made of an elastic material and is coated with an insulating layer, and the conductive outer, inner, and bottom layers are coated over the insulating layer. In another embodiment, the outer, inner and bottom layers include a first conductive layer, and the inner and outer layers include a second conductive layer. The second conductive layers are electrically connected by way of the first conductive layer on the bottom edge, and the first conductive layer comprises a heating element when current flows through the device.

In one embodiment, the inner and outer layers include at least two conductive layers, such that one layer is thinner and has a higher resistance than the other. In another embodiment, the supporting element is composed of nitinol, and the inner, outer, and bottom layers are coated with a tantalum layer coated with a tantalum oxide layer coated with a second tantalum layer. Furthermore, the inner and outer layers also have a gold layer coated over the second tantalum layer. In another embodiment, the supporting element is composed of an elastic material. In a further embodiment, a portion of the elastic supporting element is coated with an adhesion material. In a still further embodiment, a portion of the adhesion material is coated with a diffusion barrier material.

BRIEF DESCRIPTIONS OF THE DRAWINGS

The disclosed embodiments have other advantages and features which will be more readily apparent from the following detailed description of the invention and the appended claims, when taken in conjunction with the accompanying drawings, in which:

FIG. 24A illustrates a schematic cross-sectional side view of a support structure of a surgical device for performing a capsulotomy, according to an embodiment of the invention.

FIG. 24B illustrates a schematic cross-sectional view illustrates a schematic cross-sectional side view of a support structure of a surgical device for performing a capsulotomy, according to an embodiment of the invention.

FIG. 25A illustrates a schematic cross-sectional view of a surgical device for performing a capsulotomy including a compression chamber and a suction cup, according to an embodiment of the invention.

FIG. 25B illustrates a schematic side view of a suction cup of a surgical device for performing a capsulotomy, according to an embodiment of the invention.

FIG. 25C illustrates a schematic side view of a suction cup of a surgical device for performing a capsulotomy, according to an embodiment of the invention.

DETAILED DESCRIPTION

Figure 1:
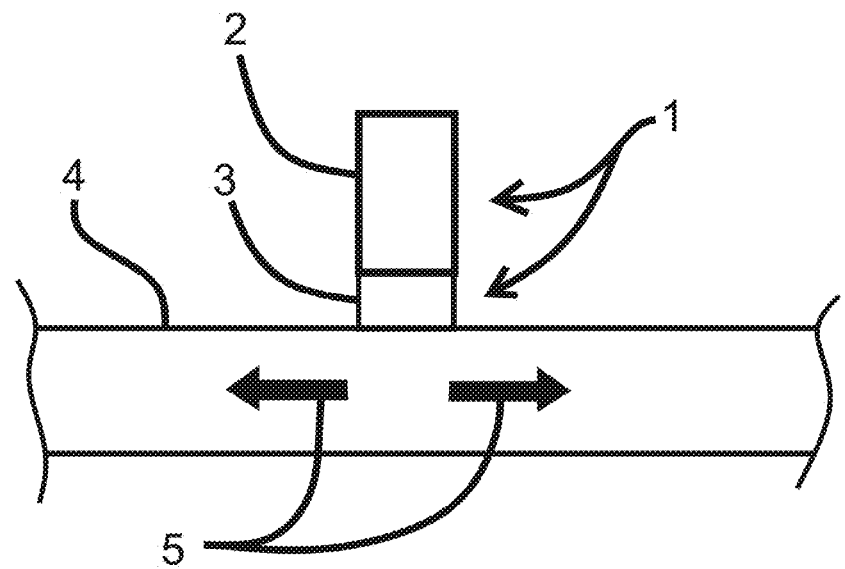
FIG. 1 illustrates a schematic cross-sectional view of an electrical cutting element in contact with a membrane, according to an embodiment of the invention.

The figures and the following description relate to various embodiments of the invention by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Embodiments of the invention include a surgical device for performing a capsulotomy on the eye, the device including any combination of some or all of the following features: a hand piece (that may include or attach to a support structure) coupled to an electrical cutting element, an elastomeric structure, such as a suction cup that is slidably mounted to the hand piece, a suction system (which may reside within the hand piece), an electrical cutting element (also can include or can be referred to as an electrical cutting element, a heater, or a heating element, though in some cases the terms "heater" or "heating element" are used to refer to only a portion of the electrical cutting element) coupled to the suction cup, and a compression chamber (to reduce the width of the suction cup and electrical cutting element prior to insertion through a corneal incision) that is removably mounted to the hand piece (or that can be a structure separate from the hand piece). The suction cup and suction system are not included in some embodiments.

In one embodiment, the electrical cutting element is a reversibly collapsible electrical cutting element that is configured for cutting a portion of the capsule membrane of the eye. In a further embodiment, the electrical cutting element is an electrode. In another embodiment, the electrical cutting element is circular in shape. The electrical cutting element may be constructed for circumferential current flow, and thus composed of patterned gold on nitinol, patterned gold on stainless steel, unpatterned gold on nitinol, unpatterned gold on stainless steel, nitinol only, or stainless steel only. The electrical cutting element may alternatively be constructed for radial current flow.

In an embodiment, the entire surgical device is preassembled (hand piece/cable/compression chamber/suction cup/electrical cutting element) as a single-use disposable unit. In another embodiment, the device includes a single-use prepackaged compression chamber containing the suction cup/electrical cutting element/suction producing component or components, which is plugged into the hand piece prior to use, with the hand piece and cable being reusable. In another embodiment, the device includes a single-use prepackaged suction cup/electrical cutting element/suction producing component or components, which is plugged into the hand piece prior to use, with the hand piece and cable being reusable. In a further embodiment, the suction cup/electrical cutting element is pre-compressed and pre-packaged into the inserter.

The term "gold," as used herein, may be interchangeable with any suitable good conductor, such as Pt, Cu, Ni, Ta, Ir, Re, and their alloys. In some embodiments, an insulator includes polymers (e.g., kapton, silicone, etc), glass (e.g., chemically strengthened glass), or ceramic (including tantalum oxide, titanium oxide, nonconductive oxides, nitrides, and oxynitrides, etc.). A heating element may be made from a large set of suitable conductive materials including: gold, Pt, Ta, Ir, Re, Al, Ag, and their alloys (e.g., Ta/Al, Pt/Ir, etc), tantalum nitride, titanium nitride, carbides that are doped to be conductive, etc. In addition, the term "nitinol," as used herein referring to a mechanical support element (or supporting element), may be interchangeable with any suitable elastic material, such as chemically strengthened glass, Hi Ten steel, stainless steel, polymer, or kapton.

Though the description is focused throughout on capsulotomies, the device and method can also be used for other surgical procedures associated with the eye or other parts of the body.

FIGS. 1 though 15 illustrate key structural features and modes of operation of embodiments of the invention. The devices illustrated in the figures can represent separate embodiments or can be used together or portions thereof interchanged in some embodiments.

FIG. 1 illustrates a schematic cross sectional view of an electrical cutting element, according to an embodiment. In an embodiment, the electrical cutting element is an electrical cutting element configured for cutting a portion of a capsule membrane of the eye. The electrical cutting element (1) includes a surgical device having a mechanical support element (2), and an electrical heating element (3). The electrical heating element (3) or heater is brought into contact with a membrane, or layer of tissue (4), that has a tensile stress field (as indicated by the arrows labeled 5) within it. In an embodiment, the device itself may create tensile stress after it contacts the tissue.

Figure 2:
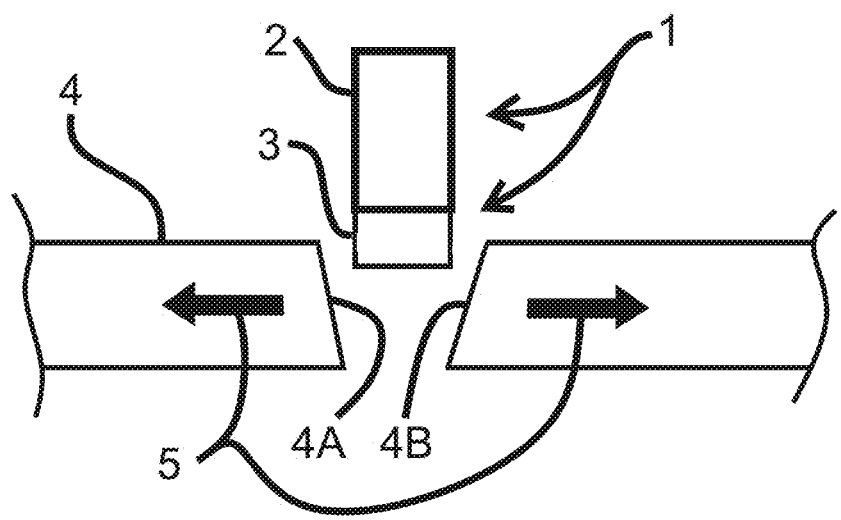
FIG. 2 illustrates a schematic cross-sectional view of an electrical cutting element and a cut membrane, according to an embodiment of the invention.

FIG. 2 also illustrates a schematic cross sectional view of an electrical cutting element, and shows the immediate result of sending a prescribed electrical pulse or series of pulses through the heating element (3), according to an embodiment. The membrane under the heater is cut, and the tensile stress has pulled the newly created cut surfaces (4A and 4B) away from each other.

FIGS. 3 through 6 show various electrical cutting element design strategies in schematic cross sectional views. In some embodiments, the heated region is isolated to the vicinity of the heating element in contact with the tissue to be cut, and a lower temperature is maintained within the mechanical support element/support structure (or supporting element).

Figure 3:
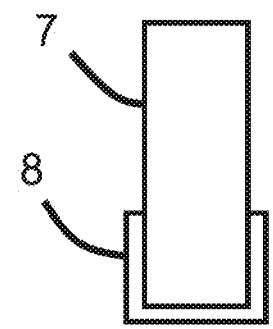
FIG. 3 illustrates an electrical cutting element including a support structure and an electrical cutting element, according to an embodiment of the invention.

FIG. 3 shows an electrical cutting element including a mechanical support element (or support structure or supporting element) (7), and electrical heating element (8), according to one embodiment. The heating element is in direct contact with the mechanical support so the ratio of the current that flows through them depends on the relative resistivity ($\rho$) of their respective materials, and their relative cross sectional areas. In one example, the mechanical support is made of nitinol ($\rho$=82 micro ohm-cm), which is a superelastic metal alloy, and the heater is gold ($\rho$=2.24 micro ohm-cm), thus the conductivity of the material for the heater is 37 times greater than the conductivity of the material of the mechanical support. If the cross sectional of the area of the heater is 1/3.7 the area of the mechanical support, then the current in the heater will be 10 times the current in the mechanical support. Since power is current squared times resistance, the power dissipated by the gold will be 10 times greater than the mechanical support, and since the volume is smaller by a factor of 3.7, the power density is 37 times greater in the gold. The consequence of this strategy is that the temperature rise at the gold heating element is significantly greater than in the mechanical support element.

Figure 4:
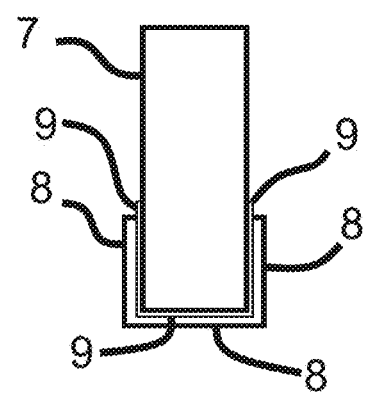
FIG. 4 illustrates an electrical cutting element including a support structure and an electrical cutting element with an insulating layer, according to an embodiment of the invention.

FIG. 4 shows an electrical cutting element in which the heating element or heater (8) is electrically isolated from the mechanical support structure (7) by an insulating layer (9), according to one embodiment. All heat generation occurs in the heater, resulting in increased efficiency. In an embodiment, the mechanical support is made of nitinol. The following layers can be deposited (e.g., by sputtering) onto the electrical cutting element and/or support structure: Ta (e.g., 1000 angstroms, adhesion layer), $Ta_2O_5$ (e.g., 1 micron insulating layer), Ta (e.g., 1000 angstroms, adhesion layer), W (1000 angstroms, optional anti-diffusion layer), Au (e.g., 1000 angstroms, plating seed layer), and thick Au (e.g., 2 microns) patterned (e.g., by sputtering shadow mask, or if plated, by photoresist). The pattern places the thick gold heater on the bottom region of the electrical cutting element where it can contact the tissue.

Figure 5:
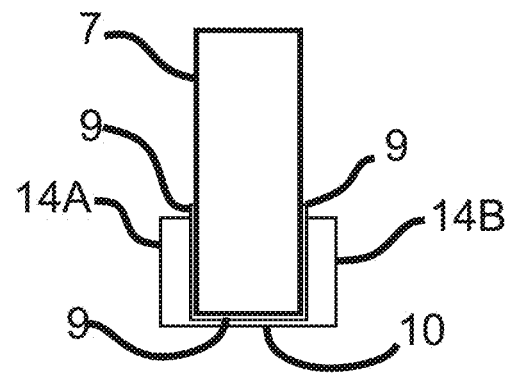
FIG. 5 illustrates an electrical cutting element including a support structure a low thickness heating element, according to an embodiment of the invention.

FIG. 5 shows an electrical cutting element including a heater construction in which only a low thickness heating element (10) will increase in heat, according to one embodiment. In FIG. 5, a mechanical support (7) is isolated from the electrical conducting elements (14A, 14B, 10) by an insulating layer (9). The side walls (14A-B on both the inner diameter (ID) and the outer diameter (OD) sides of the electrical cutting element) of the electrical element are relatively thicker and have lower resistance than the low thickness heating element (10). Therefore a short pulse of electric current (along the path shown in FIG. 11 by the arrows labeled I (i.e., into 14A, then through 10, then to 14B, then out of 14B)) will cause a significant temperature increase only in the low thickness heating element (10). In an embodiment, the low thickness heating element (10) is or includes a bottom layer on a bottom edge of the electrical cutting element. Note that, in FIG. 5, the current flow occurs in the plane of the drawing, while in FIGS. 3, 4, 6, 7, 8, 11, and 15, the current flow is perpendicular to the plane of the drawing (i.e., in the low thickness heating element of FIG. 5, the current flow is radial in the ring, while in FIGS. 3, 4, 6, 7, 8, 11, and 15, it is circumferential).

Figure 6:
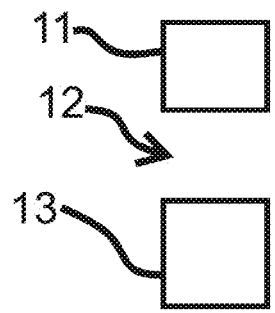
FIG. 6 illustrates an electrical cutting element including a support structure and composed of electrically conductive material, according to an embodiment of the invention.

FIG. 6 shows an electrical cutting element in which the entire structure is made up of electrically conductive material, and the geometry of the design is used to confine the current to the heater region, according to one embodiment. The heating region (13) makes a continuous circuit, while the mechanical support region (11) has breaks that eliminate a circuit path, and also has empty gaps (12) that physically isolate it from thermal conduction from the heater. FIG. 14B shows a partial side view of an electrical cutting element using this strategy. This geometric isolation strategy (FIGS. 6, 14B) can be used in combination with any of the other strategies.

Figure 7:
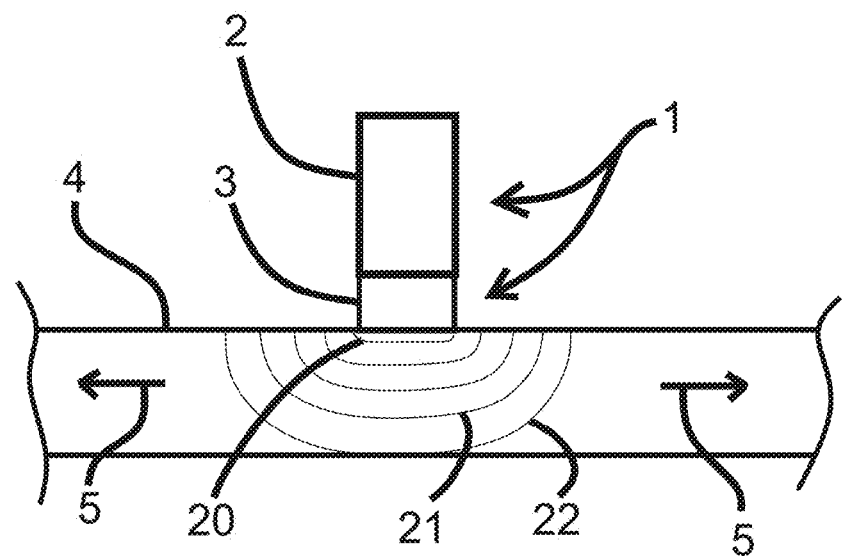
FIG. 7 illustrates a schematic cross-sectional view of a heating electrical cutting element that is capable of delivering a single electrical current pulse to a membrane, according to an embodiment of the invention.
Figure 8:
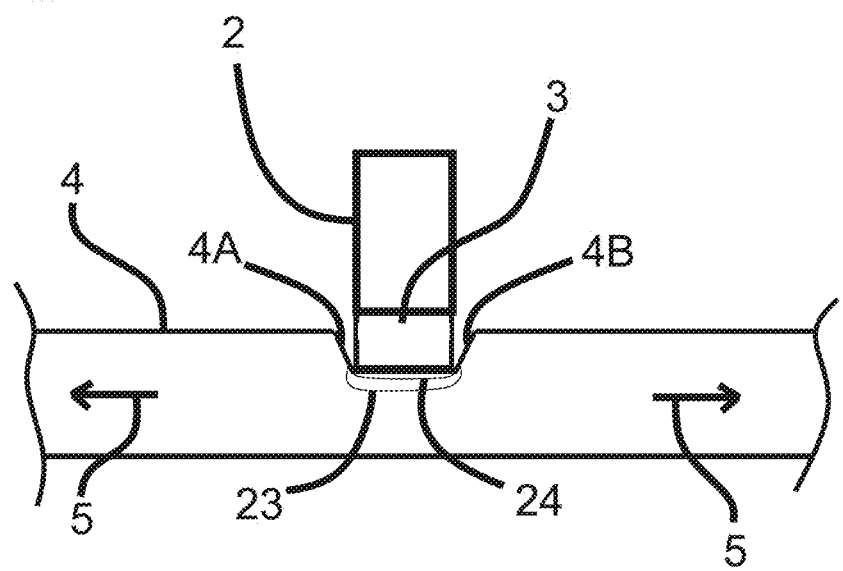
FIG. 8 illustrates a schematic cross-sectional view of a heating electrical cutting element that is capable of delivering a series of short electrical current pulses to a membrane, according to an embodiment of the invention.

FIGS. 7 and 8 show schematic cross sectional views of a heating electrical cutting element (3) in contact with a membrane (4), such that the heating electrical cutting element (3) can be operated with different strategies in timing for the electrical current pulse. In FIG. 7, a single pulse is used to cut the membrane in one shot, according to one embodiment. Isotherms (20, 21, 22) show contours of constant temperature at a given instant (for example, at the instant just before explosive vaporization occurs, and the material located on isotherm 20 is at the threshold temperature at which explosive vaporization can occur, while the material at isotherm 22 is still at 50 C).

In FIG. 8, the membrane is cut incrementally by a series of shorter pulses, according to one embodiment. Newly created surfaces (4A and 4B) move away from each other due to the tensile stress field (indicated by arrows 5) and the electrical cutting element proceeds deeper through the membrane with each succeeding pulse. At the instant just before explosive vaporization, material that has reached the threshold temperature (e.g., at isotherm 24) is just a few microns from the heater, and the distance to the 50 C isotherm (e.g., 23) is less than the width of the electrical cutting element. The total energy needed for the multi-pulse method is less than for the single pulse method, since there is less time for heat conduction laterally to neighboring tissue, and a smaller volume is heated. In an embodiment, a low thickness heating element strategy (seen in FIGS. 5, 11, 12, 13) uses a multi-pulse method to cut a membrane. A shorter pulse duration (e.g., 1 to 10 microseconds) allows the possibility of increased instantaneous power, but decreased total energy. The cool down time is longer for a single large pulse, thus more extensive annealing of collagen is expected for the newly formed surfaces when a single pulse strategy is used. The multi-pulse strategy may extend annealing time further by modifying the falling edge of the current pulse to hold at a predetermined annealing temperature for a predetermined time (e.g., at 80 C for 1 millisecond).

In an embodiment, the electrical cutting element cuts tissue at the microscale. In a further embodiment, the electrical cutting element cuts a membrane by imposing a state of tensile stress along the path where the cut is desired, and then creates a very quick pulse of heat to make the cut. The geometry of the mechanical structure controls the applied tensile stress field, and the electronic circuitry controls the heat pulse. In the case where the membrane to be cut is the capsular membrane of the lens of the eye, there is a wide spectrum of parameters that can be used. The lens capsule is made of type IV collagen, and has a melting point of less than about 50 C. A number of electronic heating methods can be used to achieve the needed temperature, such as simple DC current heating of an electrical cutting element, or RF, or plasma heating. In all cases, heat generation must be ramped up quickly and maintained for a short duration so that only the volume of material to be cut is heated significantly, and nearby tissue is not harmed. There are several mechanisms of cutting that can occur in the presence of a tensile stress field, including: (1) melting, (2) thermal weakening of the membrane in combination with thermally-generated pressure, and (3) dielectric breakdown and plasma heating.

In one example, the heating element has to be heated above about 50 C to melt a collagen membrane so that the molecules on opposite sides of the cutting line can slide away from each other under the influence of the force already present in the tensile stress field. The melting can be done on the time scale of microseconds, but the cooling is on the scale of a millisecond, so there is time during cooling for the collagen molecules on the newly formed surfaces to anneal into a very smooth surface with a low population of defects. Scanning electron microscopy can show the surface of the cuts to be smoother than the surfaces produced by capsularhexis (which is done by manually tearing the membrane, and which stays below the annealing temperature and the melting point). The membrane edge surfaces produced in this example are much smoother than can be obtained by any of the other devices that have been demonstrated, such as the plasma knife (Fugo blade) and the femtosecond laser.

FIG. 8 shows a schematic view of a membrane having a tensile stress field (indicated by arrows 5) within it, and an electrical cutting element in contact with one surface where a cut is desired, according to one embodiment. At time t=0, a current pulse is applied to the electrical cutting element to generate heat. FIG. 8 shows isotherms (contours of equal temperature) at a short time (e.g., one, or a few, microseconds) after energizing the pulse. The electrical cutting element is now at a high temperature (e.g., greater than 400 C) and heat is flowing into the tissue that contacts it. The current in the electrical cutting element is maintained at the high temperature, and the temperature in the tissue adjacent to the electrical cutting element has exceeded the threshold needed for spontaneous vaporization. Although water normally boils at 100 C, it takes time to nucleate bubble formation because diffusion of gases through the liquid is required. During a short thermal transient, bubble formation will not have time to nucleate, so the temperature can rise substantially above 100 C without a phase change. This results in a superheated liquid. As the temperature continues to rise, the thermal energy density in the heated volume reaches the point at which molecules directly go into the vapor phase without requiring the nucleation of a bubble. In pure water, the critical temperature is 374 C (since biological tissue, while not pure water, has sufficient concentration of water to generate high pressure vapor).

The processes of flash melting and flash vaporization can occur instantaneously after exceeding a threshold temperature, since no diffusion of molecules is needed. In one embodiment, the heat generation is ramped up quickly enough so that vaporization can occur in a volume of tissue within a few micrometers of the electrical cutting element (e.g., 5 micrometers), though the distance from the electrical cutting element to the 50 C isotherm is still on the cellular scale (e.g., 30 micrometers). The vaporized volume expands with a pressure that acts in concert with the pre-existing tensile stress to move the tissue away from the electrical cutting element, thereby producing a cut. When no further heat production is needed, the electrical cutting element current can be turned off, and within less than about 1 to 2 milliseconds the tissue and electrical cutting element will have cooled down. The electrical cutting element can then move deeper into the tissue and come into contact with new tissue, and the pulse/cut process can be repeated to make a still deeper incision. This sequence of events can be repeated as many times as appropriate to achieve a specific depth of incision.

The lens capsule may generally already be in a state of tensile stress due to the internal fluid pressure that is naturally maintained. Using capsularhexis, this natural internal pressure is lost as soon as the initial tear is made in the center, thus the actual manual rhexis is made without the benefit of a pre-established tensile stress in the membrane. In an embodiment of the invention, the electrical cutting element or electrical cutting element, cuts the membrane simultaneously in a 360 degree circle, thus the pre-existing membrane stress is present to assist the entire rhexis.

In another embodiment, a device may apply additional tensile stress to a membrane. Such stress may only be required over the micro scale volume immediately adjacent to the electrical cutting element. Methods of applying stress to the tissue include using suction, electrostatic attraction, chemical adhesion, or simply pushing the electrical cutting element against the tissue.

Figure 9:
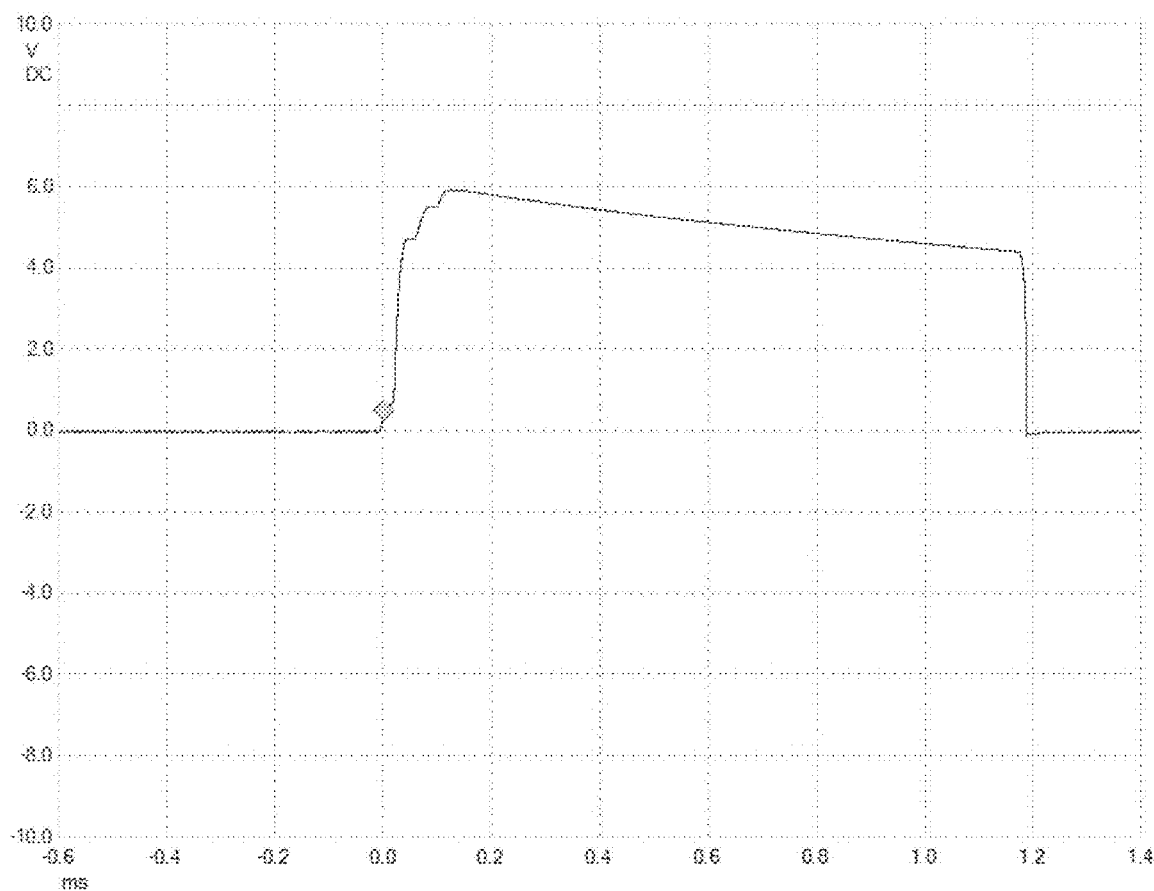
FIG. 9 illustrates a graph depicting a voltage drop of an electrical cutting element over a period of time, according to an embodiment of the invention.

FIG. 9 shows data from an anterior capsulotomy performed on the lens of an eye removed from a rabbit, using the current invention with the single pulse strategy, according to one embodiment. The left axis shows the voltage drop across a 0.1 ohm sense resistor. Multiplying the voltage drop by 10 generates the current in amps through the electrical cutting element (e.g., $I_{max}$=about 59 amps). The horizontal axis shows the time with 0.2 milliseconds per division (total pulse width about 1.1 milliseconds). As the pulse progresses, the current decreases because the voltage across the capacitor (that supplies the current) drops as it discharges.

Figure 10:
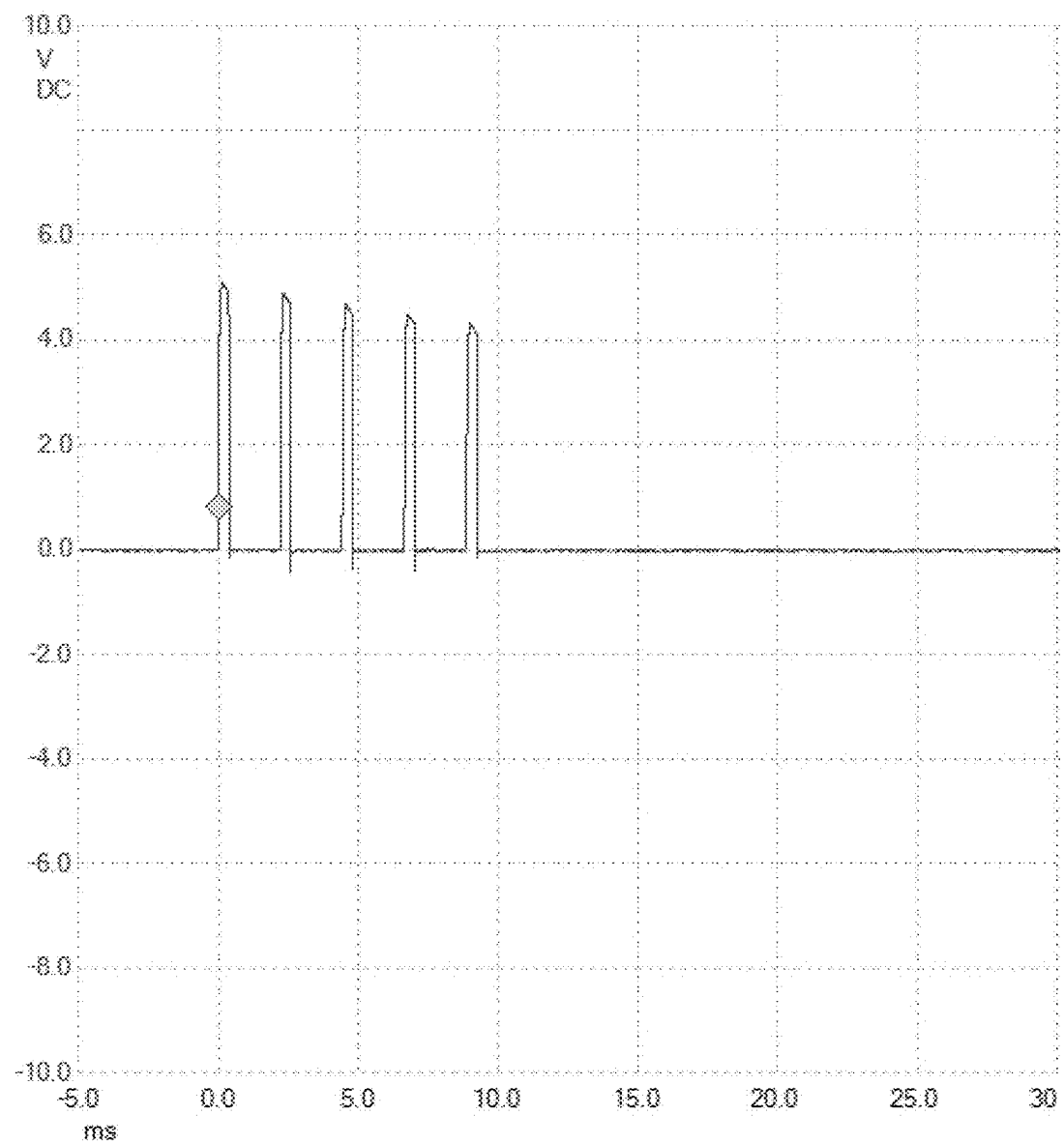
FIG. 10 illustrates a graph depicting a voltage drop of an electrical cutting element over a period of time, according to an embodiment of the invention.

FIG. 10 shows data from an anterior capsulotomy performed within the eye of a living rabbit using a multi-pulse strategy, according to one embodiment. The horizontal axis represents time (5 milliseconds per division). Five pulses of electrical current were generated. For each pulse, the current was on for 335 microseconds, and then off for 2,000 microseconds. The peak current decreased with each pulse because the capacitor was discharging during the process. The resistance of the electrical cutting element was 0.275 ohms. The average current for the 5 peaks was 46.2 amps, and the average power was 587 watts. The entire operation was over in less than 1/100 of a second. In some embodiments, shorter pulse durations are used, generating much higher power to achieve a steeper thermal gradient (e.g., greater than 50 C per micrometer) in the tissue (e.g., duration less than 10 microseconds, or even less than 1 microsecond, and instantaneous power greater than 1 kilowatt).

Figure 11A:
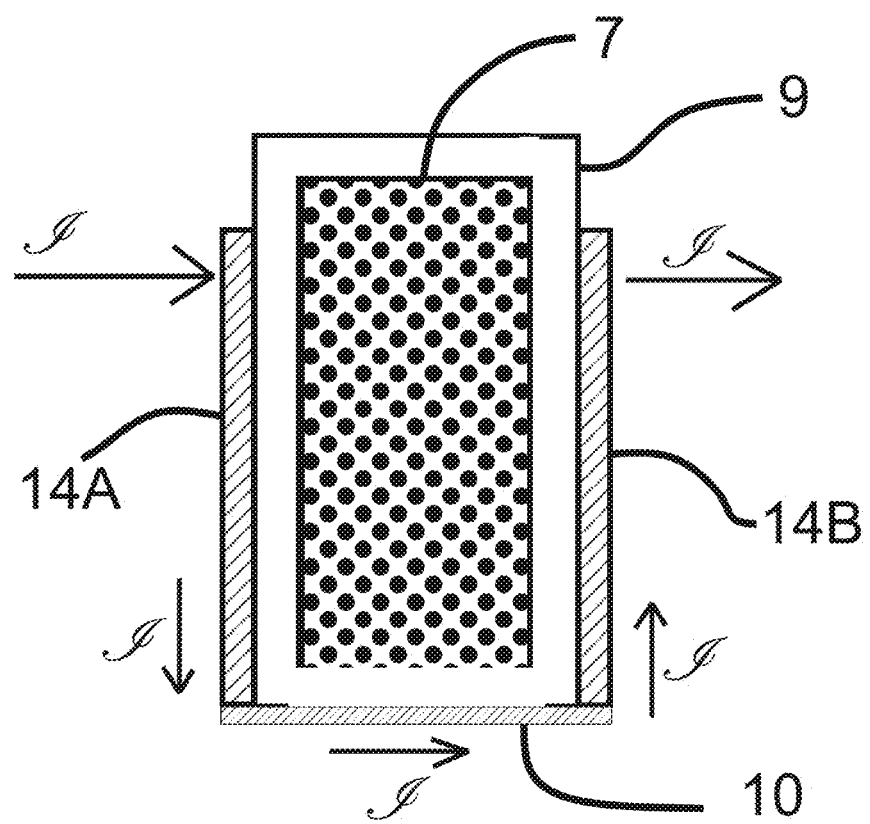
FIG. 11A illustrates a schematic cross-sectional view of an electrical cutting element including a low thickness heating element, according to an embodiment of the invention.

FIG. 11A shows a schematic cross sectional view of an electrical cutting element construction for the low thickness heating element strategy introduced by FIG. 5, according to one embodiment. A mechanical support (7) is separated by an insulating layer (9) from sidewall conductors 14A, 14B, and low thickness heating element 10. In an embodiment, the mechanical support is composed of superelastic nitinol. The arrows labeled "I" show the direction of the current flow.

Figure 12:
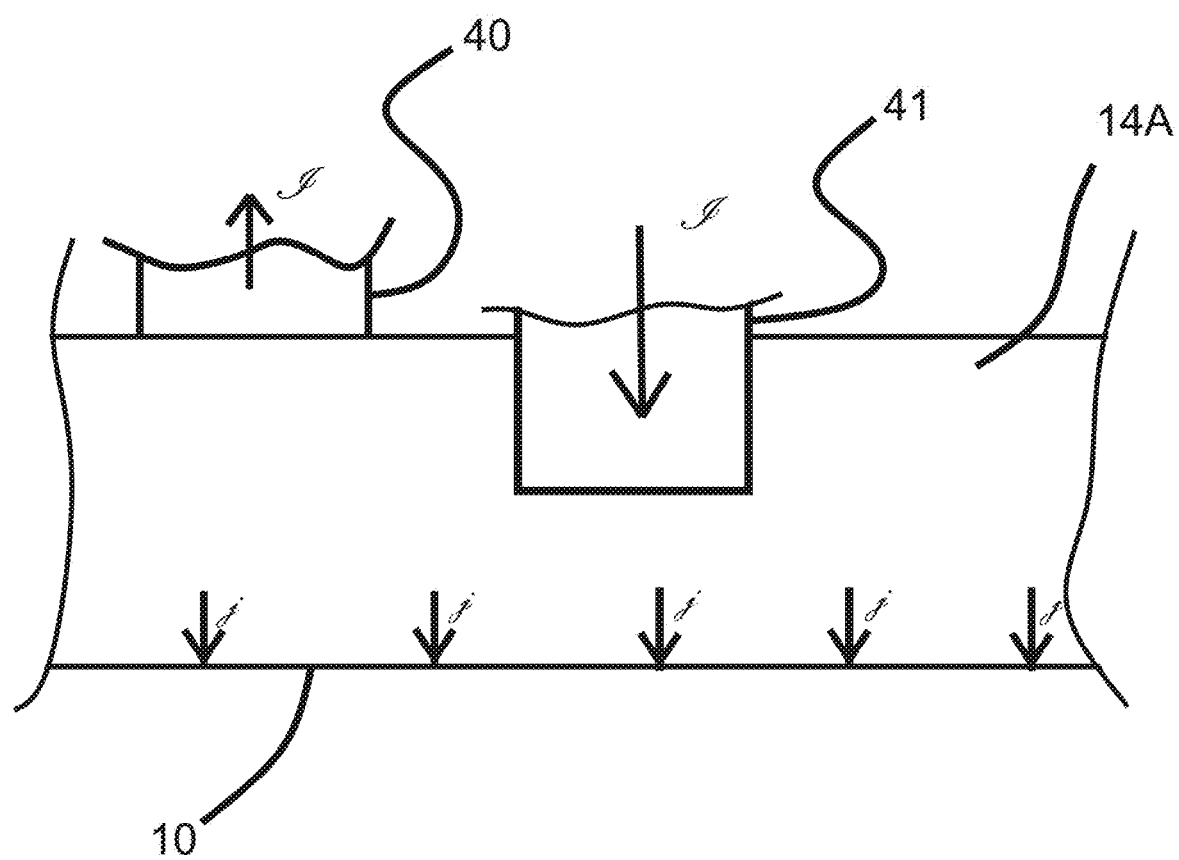
FIG. 12 illustrates a schematic side view of an electrical cutting element including an input lead, according to an embodiment of the invention.

FIG. 12 shows a schematic side view with a current carrying input lead (41) bringing the total current (I) to side wall conductor 14A, according to one embodiment. The scalar field of electric potential has permeated the conductors at a significant fraction of the speed of light, thus the current distribution shown is established at the beginning of the pulse, prior to any significant energy dissipation. The small arrows (j) show the uniform current distribution that enters the low thickness heating element 10. After leaving the low thickness heating element, the current enters sidewall conductor 14B (not shown) and leaves the electrical cutting element through exit lead 40. Uniform current density is achieved through the low thickness heating element. In an embodiment, the low thickness element is incorporated 360 degrees into a circular electrical cutting element, and the resistance of the side wall conductors 14A and 14B (higher thickness relative to the heating element 10) are minimized while the resistance of the low thickness heating element 10 is maximized. Thus, the temperature increase is constant all the way around the ring.

Figure 11B:
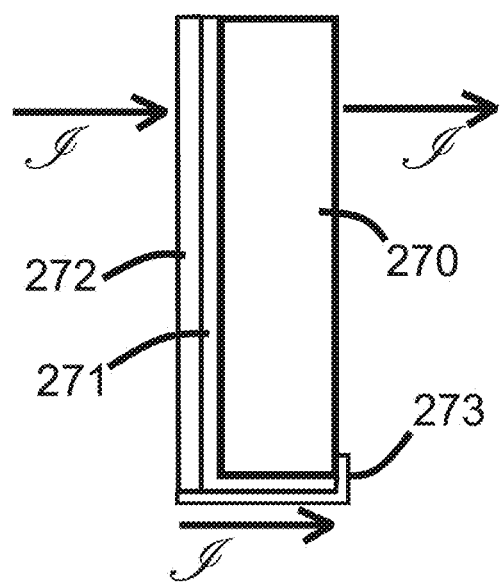
FIG. 11B illustrates a schematic cross-sectional view of a low thickness heating element of an electrical cutting element.

FIGS. 11B-F show schematic cross sectional views of several embodiments of low thickness heating elements. In FIG. 11B, the current (I) enters a high conductance sidewall (272) (e.g., 2 micron thick gold) and flows radially through the annular low thickness heating element (273), then through the mechanical support element (270). The mechanical support element has a sufficiently high conductance sidewall due to its relatively large cross sectional area even though it is made of a material (e.g., nitinol, stainless steel, etc) with higher resistivity than gold. An insulating layer (271) prevents any short circuit from (272) to (270).

Figure 11C:
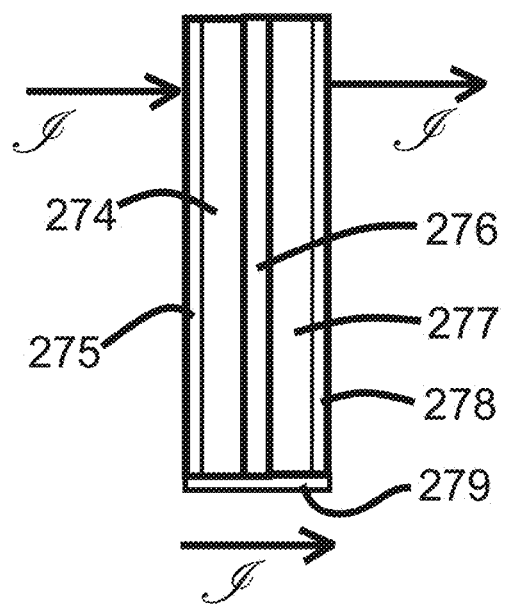
FIG. 11C illustrates a schematic cross-sectional view of a low thickness heating element of an electrical cutting element.

FIG. 11C shows an embodiment in which the current (I) flows into a low resistivity (e.g., gold, etc.) sidewall (275), which is electrically connected to a mechanical support element (274 for example, nitinol or stainless steel). Some of the current flows through the mechanical support element (274), then radially through a low thickness heating element (279), and then out through another mechanical support element (277)/high conductivity sidewall (278) combination. An insulator (276) prevents current from bypassing the low thickness heating element (279).

Figure 11D:
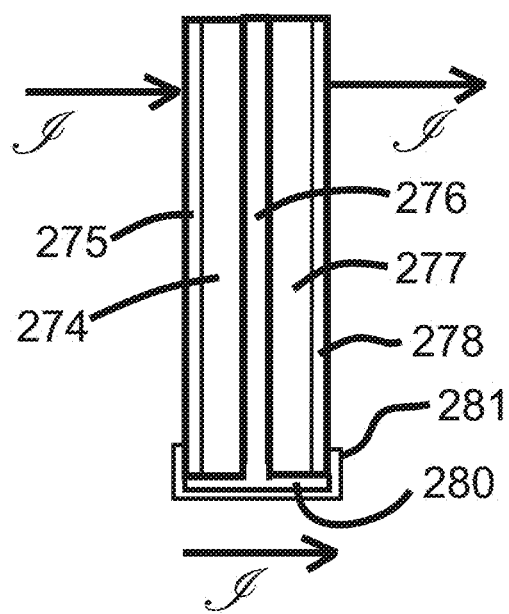
FIG. 11D illustrates a schematic cross-sectional view of a low thickness heating element of an electrical cutting element.

FIG. 11D shows an embodiment similar to that of FIG. 11C, except that a greater portion of the bottom edge of the sidewalls is covered by insulator (280) so that an increased width of the low thickness heating element (281) is heated.

Figure 11E:
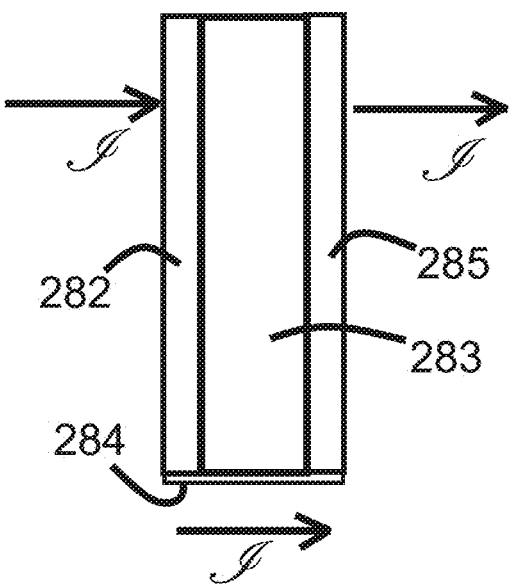
FIG. 11E illustrates a schematic cross-sectional view of a low thickness heating element of an electrical cutting element.
Figure 11:
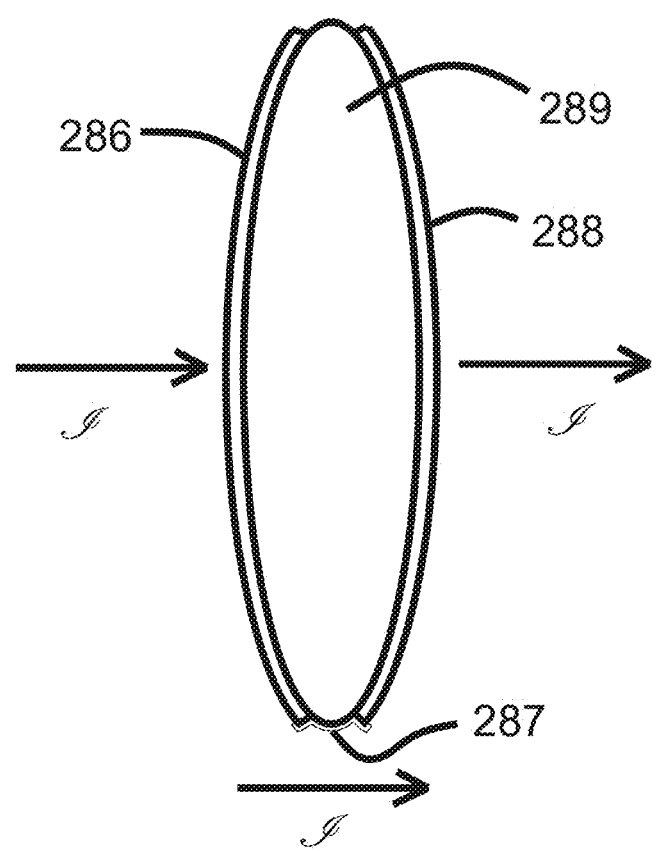
FIG. 11F illustrates a low thickness heating element of an electrical cutting element, and a rounded portion of a support structure.

FIG. 11E shows an embodiment in which the mechanical support element is an insulator such as a polymer (e.g., kapton), glass (e.g., chemically strengthened glass), or ceramic, such that the high conductance sidewalls (282, and 285) and the low thickness heating element (282) can be directly deposited onto the insulator.

FIG. 11F shows an embodiment similar to that of 11E except that the insulating mechanical support element (289) is rounded (e.g., elliptical) in the cross section instead of rectangular. This reduces the stress at the edges when the ring is compressed to go through the small corneal incision.

Figure 13:
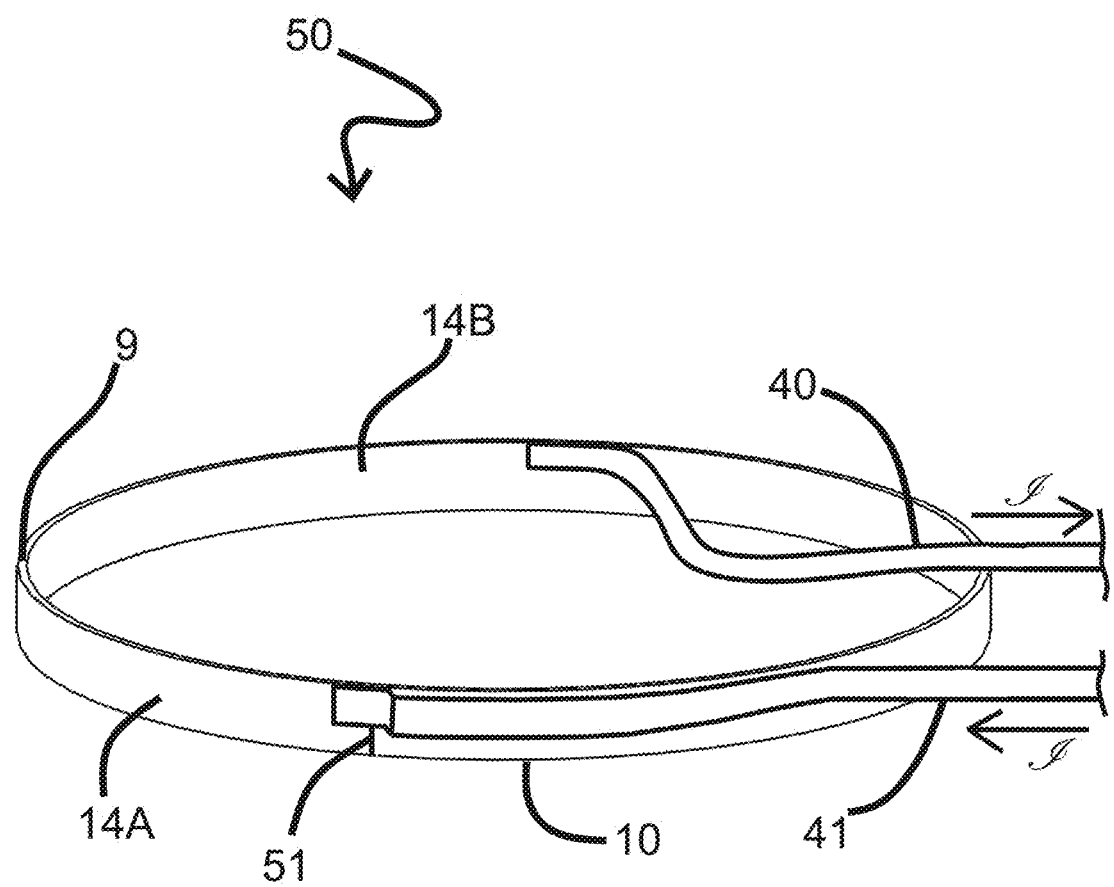
FIG. 13 illustrates a schematic perspective overview of a low thickness heating element electrical cutting element, according to an embodiment of the invention.

FIG. 13 shows a schematic perspective overview of a low thickness heating element electrical cutting element (50) having a circular ring shape, according to one embodiment. In an embodiment, if the fabrication started from planar sheet material, a joint (51) where the two ends meet forms a ring held together by the attachment of input lead 41. An output lead 40 is attached 180 degrees from lead 41, and a lead 40 is attached to ID (inner diameter) sidewall conductor 14B, while lead 41 is attached to the OD (outer diameter) sidewall conductor 14A. Arrows (I) show the reversible direction of current flow. At the beginning of the pulse, the electrical potentials are established around the ring, and in the region near the low thickness heating element the electrons travel: (1) vertically down the OD sidewalls, (2) radially, towards the center of the ring, through the low thickness heating element on the bottom edge, (3) vertically up the ID sidewalls. Higher up the side walls, away from the low thickness heating element, a circumferential component of the current flows into, or out of, the leads. In an embodiment, if the electrical cutting element is cut from tubing (of the appropriate diameter, e.g., 5.5 mm OD), or molded as a ring instead of from flat stock, the seam (51) is eliminated.

Figure 14A:
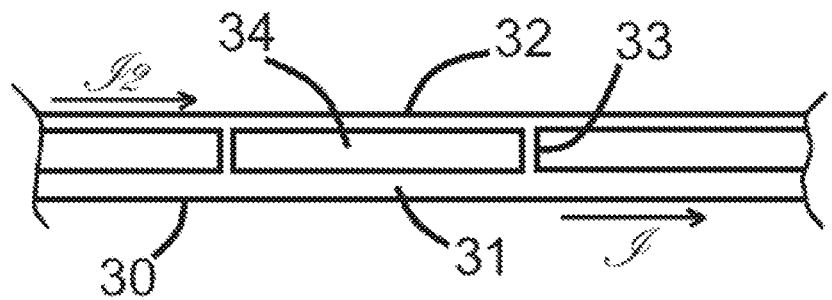
FIG. 14A illustrates a schematic partial side view of an electrical cutting element design, according to an embodiment of the invention.
Figure 14B:
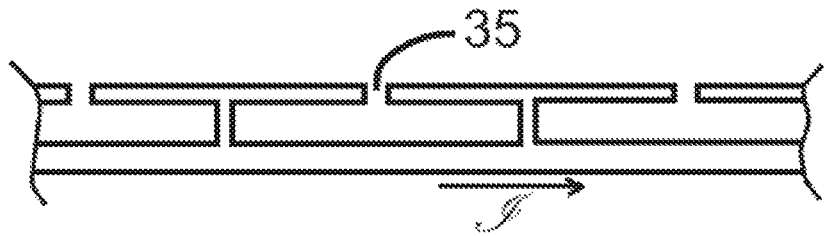
FIG. 14B illustrates a schematic partial side view of an electrical cutting element design, according to an embodiment of the invention.
Figure 14C:
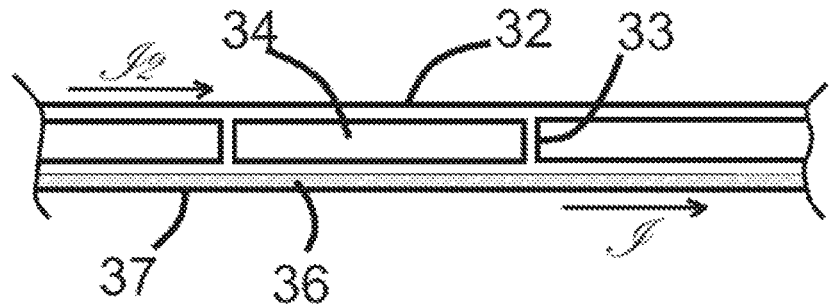
FIG. 14C illustrates a schematic partial side view of an electrical cutting element design, according to an embodiment of the invention.

FIGS. 14A-14C show partial side views of embodiments of several electrical cutting element designs. In FIG. 14A the heating element (31) and mechanical support (32, 33) are part of the same piece of metal, thus the current density is the same for both during a pulse (indicated by arrows (I) and (I2), and both elements are heated. The design of FIG. 14B solves this problem by putting gaps (35) in the mechanical support to eliminate any closed circuits. This is an example of the electrical cutting element geometry mentioned for FIG. 6. This can be used for the strategy of unpatterned gold plating (e.g., the nitinol, stainless steel, or other, mechanical support is plated everywhere with the high conductive metal such as gold). Or it can be used for unplated electrical cutting elements (e.g., plain nitinol, stainless steel, etc.).

In FIG. 14C a layer of patterned gold (deposited for example by plating or sputtering) 36 and 37, carries a higher current density than the mechanical support (as described by FIG. 3) to reduce current component (I2). In an embodiment, if an insulating layer lies between the mechanical support and patterned gold (as in FIG. 4), I2 becomes zero. In this case, only the heating element dissipates power, though heat can still conduct to the mechanical support. To minimize this effect, thermal conduction spaces 34 can be made as big as possible, and connecting beams (33) can be built to be as slender as possible.

Figure 15:
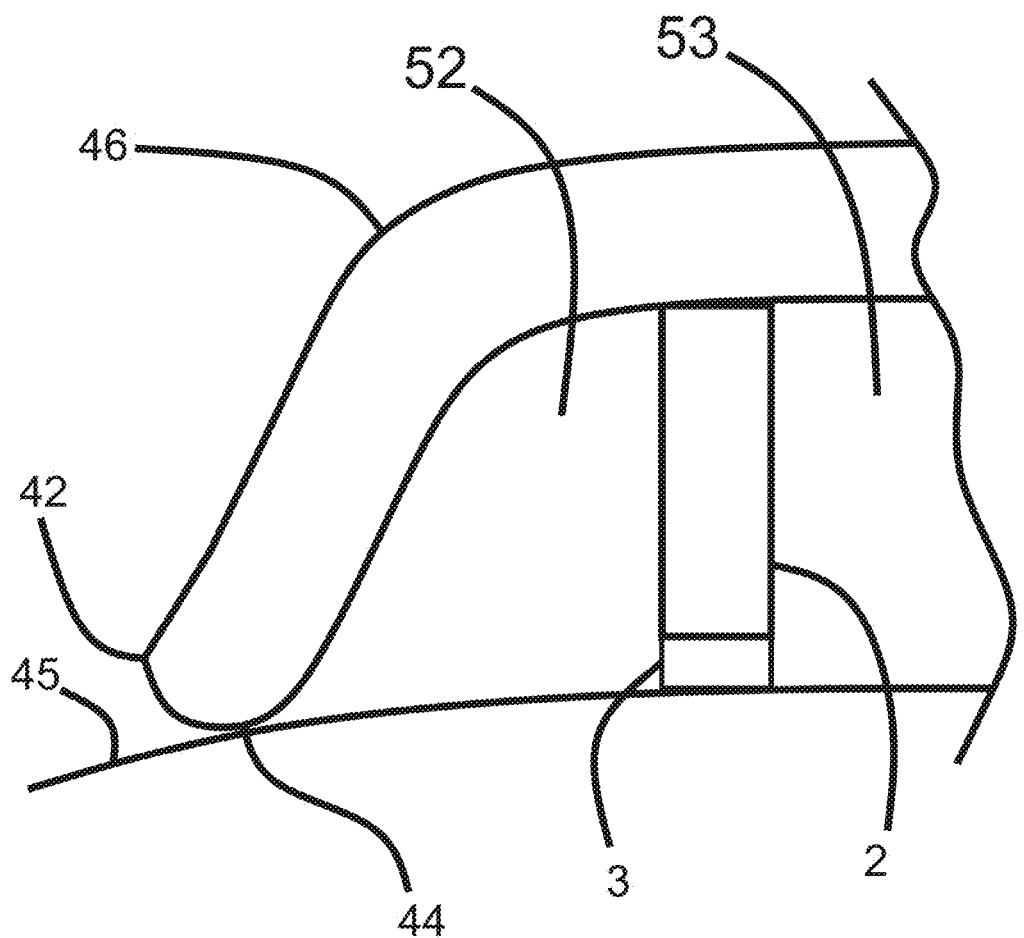
FIG. 15 illustrates a schematic cross-sectional partial side view of an electrical cutting element in contact with a membrane, according to an embodiment of the invention.

FIG. 15 schematically shows, in partial detail side view cross section, a method to establish mechanical contact between the electrical cutting element heating element (3) and the surface (45) of the tissue to be cut, according to one embodiment. An elastomeric (e.g., silicone) structure (in this embodiment, a suction cup (46)) is located such that when fluid is withdrawn from spaces 52 and/or 53, the decreased pressure will apply a force that urges the suction cup and the tissue surface to deflect towards each other. Since the electrical cutting element is in the middle, it is squeezed between them and makes a forcible contact against the tissue. In an embodiment, the suction cup creates a fluid-tight leak-proof seal with the surface of the tissue at a peripheral lip (44). In a further embodiment, if the suction cup is molded, the mold that produces the suction cup has a parting line at an elevated location (such as at 42), such that any molding flash will be away from the sealing surface.

Figure 16:
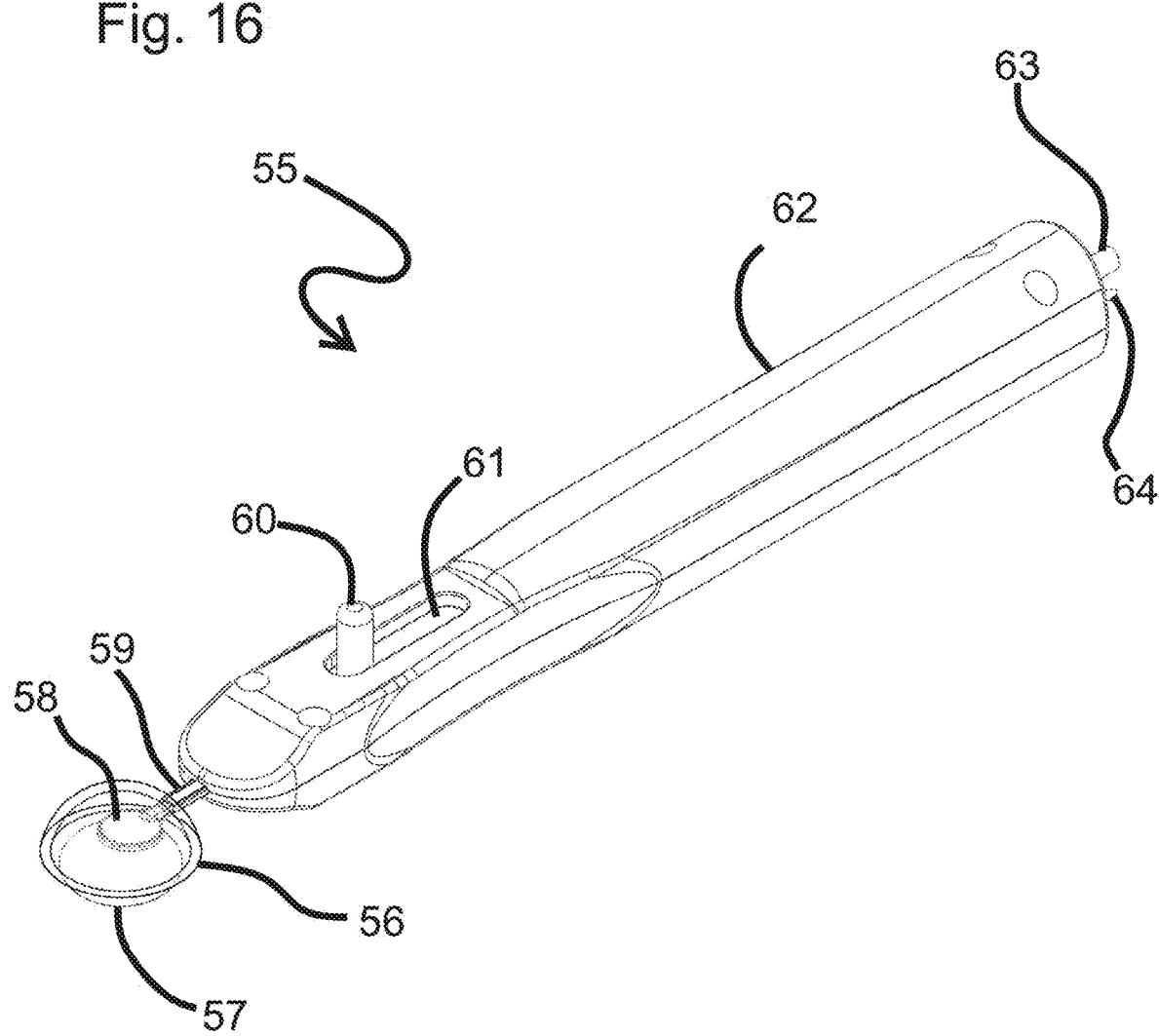
FIG. 16 illustrates a surgical device for performing a capsulotomy, including a support structure and a suction cup, according to an embodiment of the invention.
Figure 17:
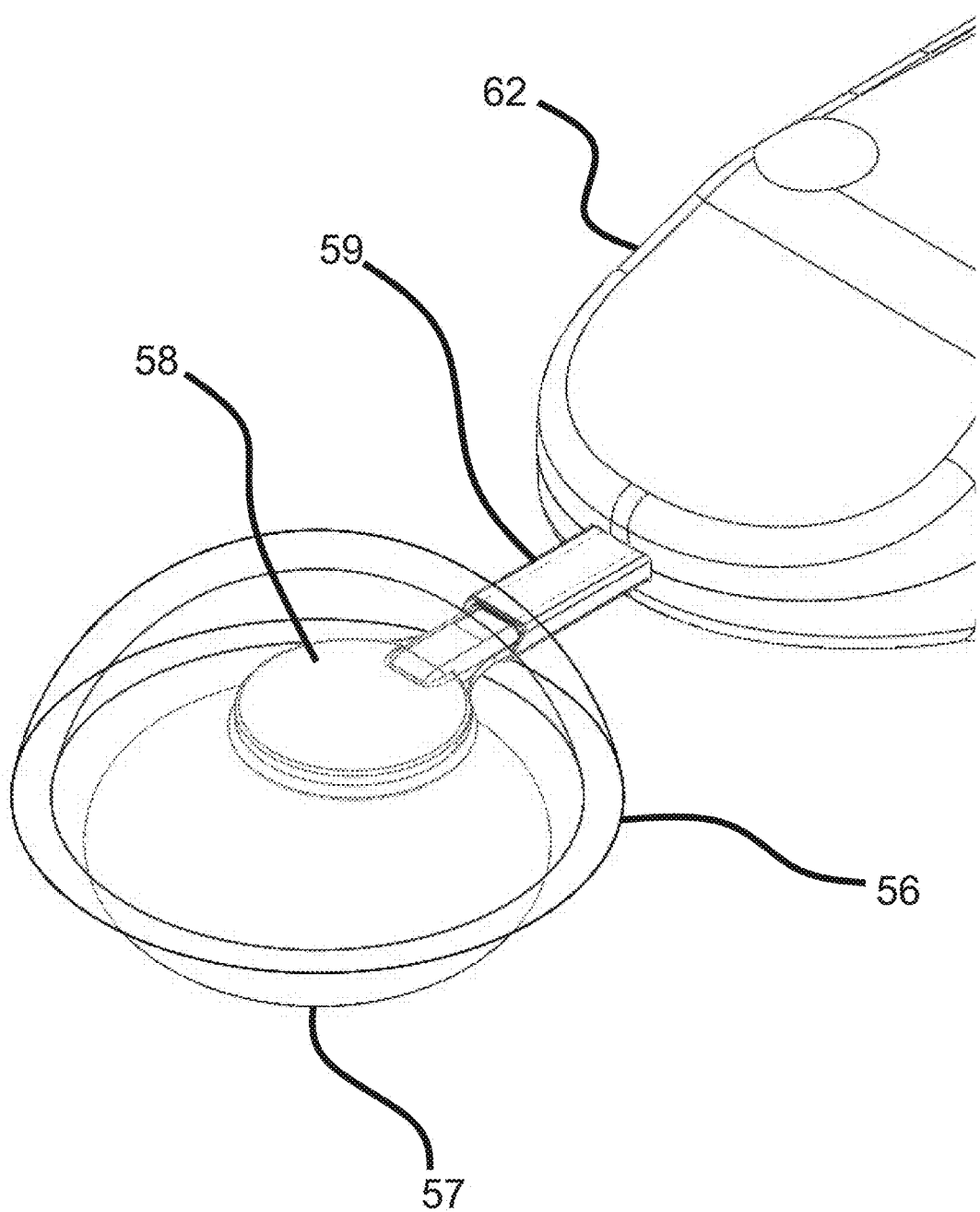
FIG. 17 illustrates a close-up view of a suction cup of a surgical device for performing a capsulotomy, according to an embodiment of the invention.

FIG. 16 shows an overview of an embodiment of the device (55). The handle (62) or hand piece may be held in the hand of a user such as a surgeon, according to one embodiment. At the proximal end of the handle are tubing for suction (63) and wiring for electrical supply (64). At the distal end of the handle are a suction cup (58) and an inserter (59). As shown, the tip of the inserter has been introduced through the cornea (56), and the knob (60) has been slid forward (distally) in slot (61) to advance the suction cup (which had been compressed within the inserter) out of the inserter and into the anterior chamber of the eye, so it can be placed against the lens (57). FIG. 17 shows a close up view of the cornea (56), lens (57), suction cup (58) and inserter (59), according to one embodiment.

Figure 18:
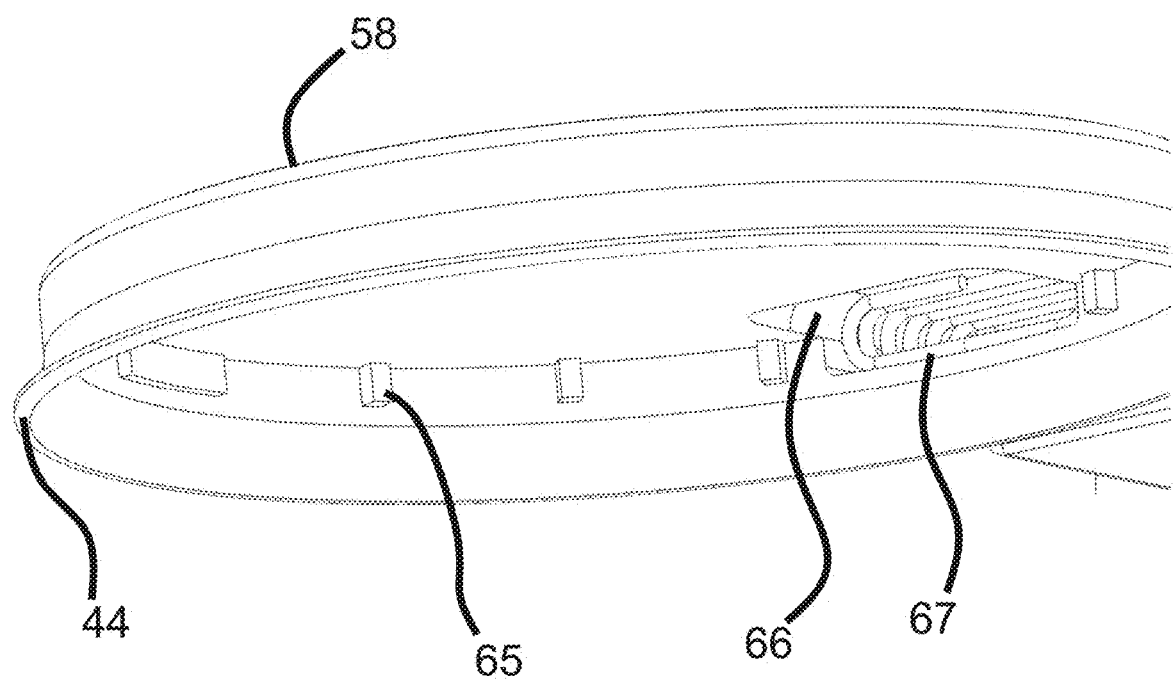
FIG. 18 illustrates a perspective view of a suction cup of a surgical device for performing a capsulotomy, according to an embodiment of the invention.

FIG. 18 shows a perspective view of the suction cup from below (electrical cutting element not shown), according to one embodiment. The elastomeric suction cup (58) has a smooth sealing surface (44), and optional standoffs (65) to help position the electrical cutting element. A lumen (66) provides a fluidic pathway for suction, and for the introduction of fluid into the suction cup as needed (e.g., to release the suction after cutting the membrane). To ensure that the lumen does not collapse under suction, an optional spring (67) is placed within the lumen. In an embodiment, the spring is a stainless steel rectangular coil spring of 75 micron diameter wire that prevents lumen collapse, but still allows for stretching and bending flexibility.

Figure 19:
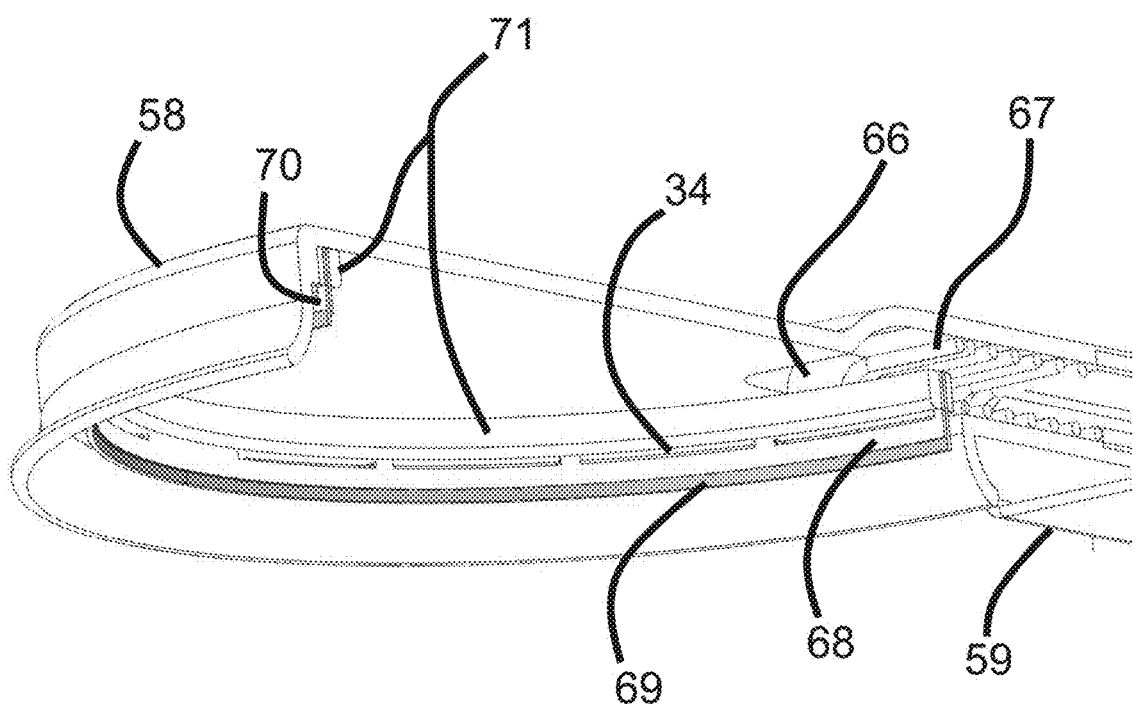
FIG. 19 illustrates a perspective view of a suction cup and electrical cutting element of a surgical device for performing a capsulotomy, according to an embodiment of the invention.

FIG. 19 shows a perspective view of the suction cup and electrical cutting element from below, according to one embodiment. In an embodiment, the electrical cutting element (70) is made of stainless steel (or nitinol), and has a patterned gold heating element (69). The ID side of the electrical cutting element contains an optional backer ring (68) made of superelastic nitinol that adds outwardly directed radial restoring forces to help the thin stainless steel (or nitinol) electrical cutting element achieve the desired circular geometry after deployment out of the inserter (59) into the anterior chamber of the eye. Slots (34) in both the backer ring and the electrical cutting element assist anchoring to the suction cup by potting compound (71) (e.g., silicone).

Figure 20:
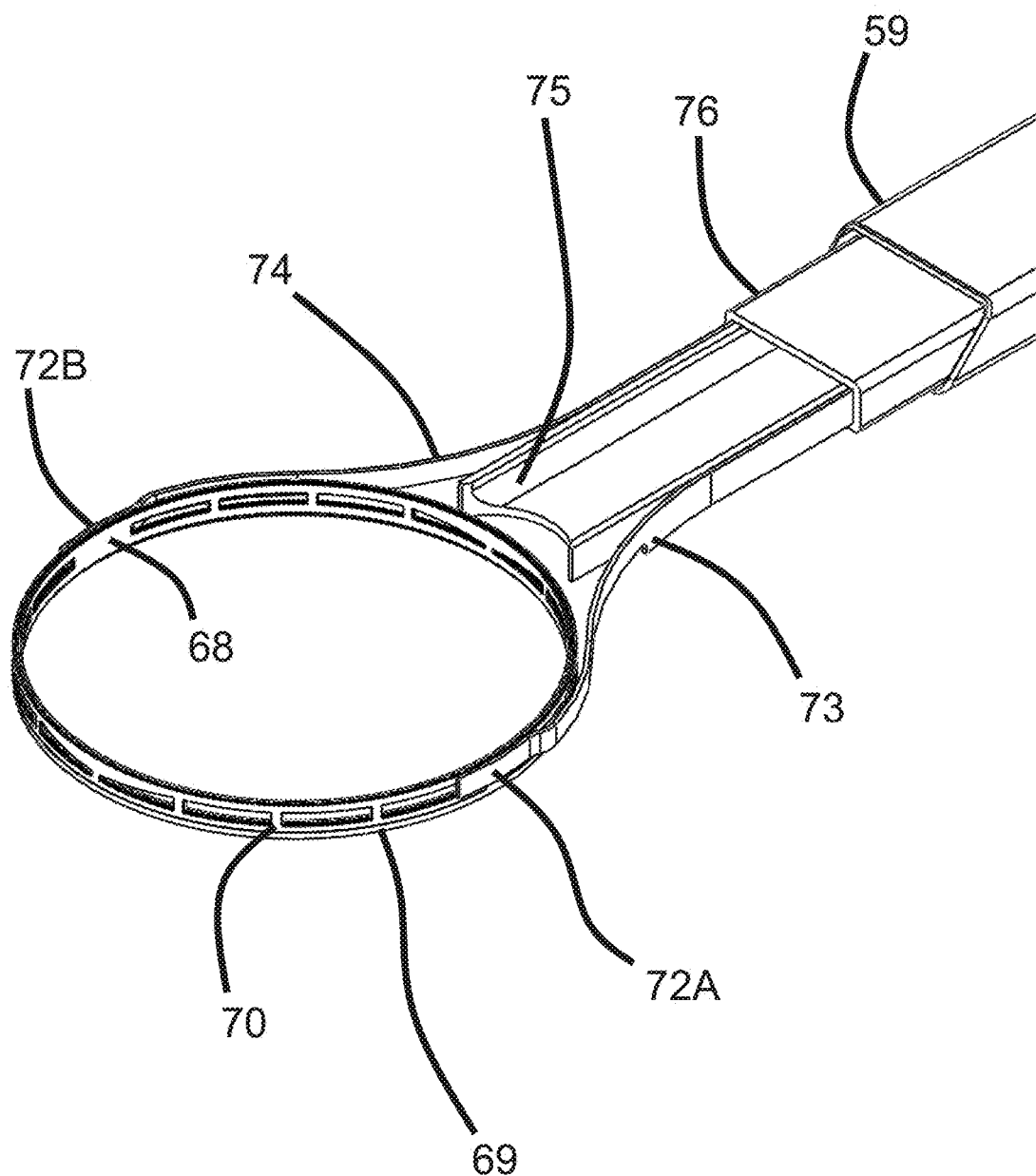
FIG. 20 illustrates an electrical cutting element of a surgical device for performing a capsulotomy, according to an embodiment of the invention.

FIG. 20 shows the electrical cutting element structure of FIG. 19 in its deployed state (but with the obscuring suction cup removed), according to one embodiment. In this embodiment a nitinol backer ring (68) exerts an outward radial force on the stainless steel electrical cutting element (70) to maintain a circular shape. The patterned gold heating element (69) contacts the tissue to be cut. The patterned gold on the electrical cutting element (68) is connected (e.g., by gold-gold diffusion bonding) to gold plated arms (73 and 74) at locations 72A and 72B which are on opposite sides (180 degrees apart) of the ring. Arms 73 and 74 may be made of stainless steel or nitinol, and then gold plated to provide sufficient current carrying capacity. Support beam (75) allows space for fluidic flow, and heat shrink tubing (76) holds the arms (73, 74) to the support beam (75). The components (along with the suction cup) can be pulled into the inserter (59) prior to passing through the corneal incision for deployment within the anterior chamber of the eye.

Figure 21:
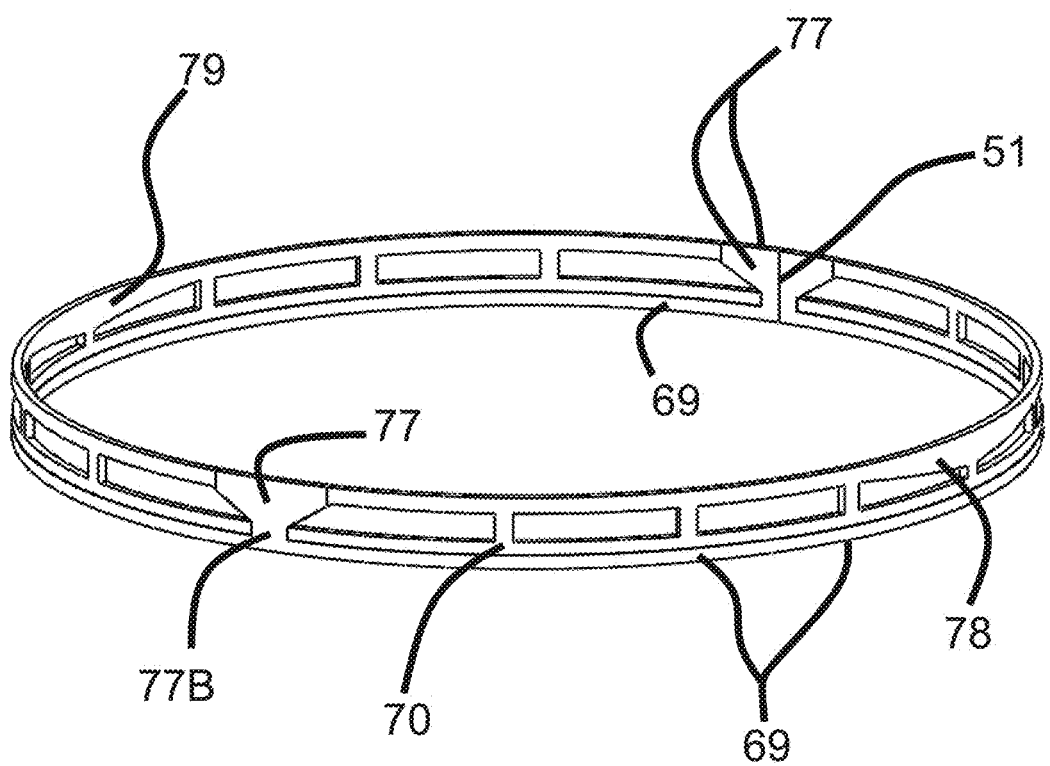
FIG. 21 illustrates an electrical cutting element, according to an embodiment of the invention.

FIG. 21 shows an electrical cutting element construction having a mechanical support (70) (made for example of stainless steel or nitinol), and a patterned heating element (69) (e.g., plated gold), according to one embodiment. The heating element is located on a bottom layer of the bottom edge of the structure (where it will press against the tissue to be cut) and may extend onto both the ID and OD sidewalls (as shown in this figure). The patterned heating element material includes bond areas (77) where the electrical leads are to be attached. As shown, the bond area metal is located on both the ID and OD sidewalls and on the top edge (which will typically be potted in to the suction cup). The connecting gold layer (77B) between the bond area 77 and the electrical cutting element heater 69 is narrow (as few degrees of arc on the circumference as possible, but with enough cross sectional area to carry the current without getting too hot). In an embodiment, the gold layer is thicker than the bond area 77 and the electrical cutting element heater 69, to avoid creating a cold spot during electrical discharge. In a further embodiment, a seam (51) is created when the flat stock the part is made from is wrapped to form a ring, and it can be eliminated by fabrication from tubing, rings, or deposition of the material layers on a cylindrical mandrel (which may be pre-coated with a sacrificial layer for easy removal of the finished parts). In a further embodiment, increasing cross sections (78, 79) are located at the most distal and most proximal locations in use that undergo the greatest strain when the ring is compressed prior to insertion through the corneal incision. This geometry increases the stiffness at the most distal and most proximal locations to reduce the local strain and to prevent kinking.

Figure 22:
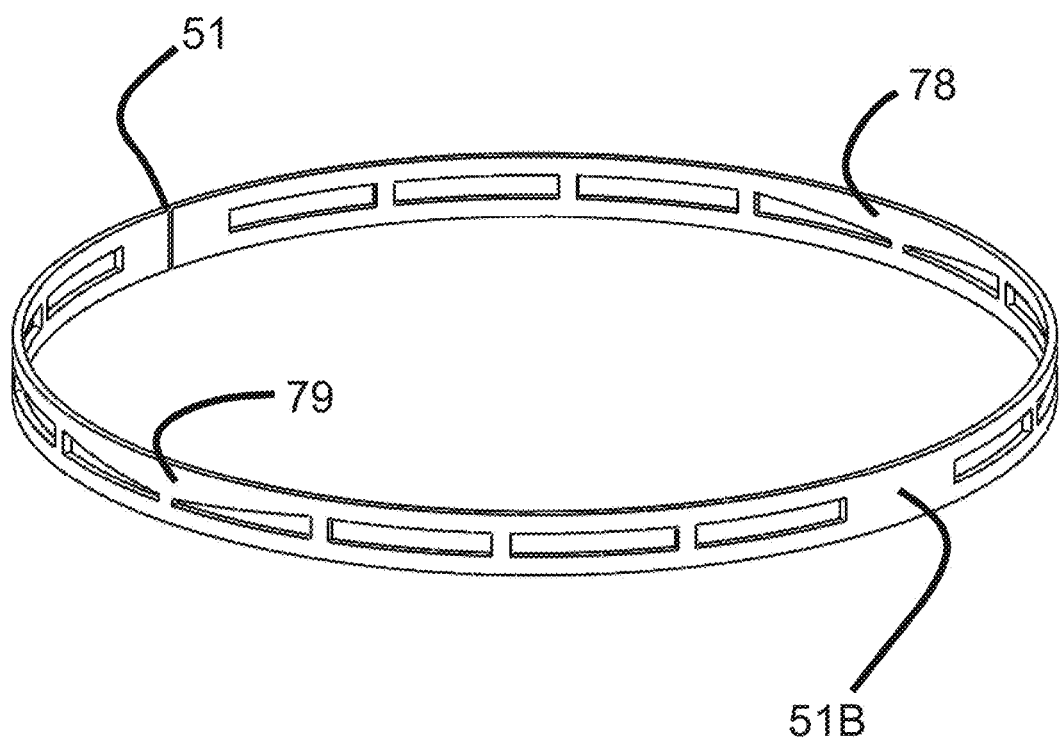
FIG. 22 illustrates a ring of an electrical cutting element, according to an embodiment of the invention.

FIG. 22 shows a backer ring (typically made of super elastic nitinol), according to one embodiment. It is configured to be placed on the ID side of a thin electrical cutting element ring. The ring can be made of stainless steel, kapton, or other elastic material. The ring allows for an extra outwardly directed radial force to be applied to ensure the restoration of circular shape (or other shape) of the electrical cutting element after it is deployed within the anterior chamber of the eye (this is because the electrical cutting element ring may have too low a stiffness, either because the material's Young's modus is low, and/or because the ring wall has to be very thin to avoid plastic strain or fracture, e.g., in the case of chemically strengthened glass). In an embodiment, backer rings made from flat stock have a seam (51). In another embodiment, for symmetry purposes, area 51B matches the geometry of the part 180 degrees opposite it even though there is no seam there. The backer ring may also have strain reducing geometries, such as (78, 79) as noted previously for the electrical cutting element. There should not be any electrical current flow between the electrical cutting element and the backer ring. In an embodiment, such an electrical current flow is prevented by having a layer, or discrete bumps, of electrically insulating material between the electrical cutting element and backer ring). In a further embodiment, a backer ring is not needed for an electrical cutting element that is made with nitinol of sufficient wall thickness (e.g., about 25 to 50 microns).

Electrical Cutting Element Design

The electrical cutting element is a ring (FIG. 13) having an OD (outer diameter) (e.g., 5.5 mm), an ID (inner diameter) (e.g., 5.392 mm), and a height (e.g., 0.4 mm). A lead (41) conducts electrical current to the OD conductor (14A). The current path travels from the entire circumference of the OD conductor to the low thickness heating element (10) at a bottom edge layer of the ring, and then to the entire circumference of the ID conductor (14B), and out through a second lead (40) which is connected to the ID conductor. The current stays constant through each circuit element since they are in series, but the current density is caused to be sufficiently high to cause a significant temperature rise (during a short pulse), only in the low thickness heating element. In an embodiment, the OD and ID conductors are gold and 0.002 mm thick. The low thickness heating element is tantalum and 0.00001 mm (100 angstroms) thick. In this case the current density is 0.002/0.00001=200 times greater in the low thickness heating element than in the sidewall conductors. The resistivity of tantalum is 6 times greater than that of gold, and the melting point of tantalum is 3017 C vs. 1064 C for gold. In an embodiment, it is desirable to have much of a voltage drop as possible, such that the circuit falls across only the low thickness heating element where energy dissipation is useful, and not across the leads or sidewall conductors. In a further embodiment, the resistance of each sidewall conductor is 0.3 milliohm, and the resistance of the low thickness heating element is 3.8 milliohms. Since the resistance of the low thickness heating element is 13 times greater than the resistance of the sidewall conductor, the power dissipated by the heater is 13 times greater, and since the area of the heater is 8 times less, the surface power density (watts/per square micron that is being conducted to the contacting tissue) at the low thickness heating element is 104 times greater than at the sidewalls.

Other materials that may be used for the low thickness heating element include platinum, gold, iridium, rhenium, Ni, Ag, and/or any of their alloys (including alloys with elements that could not be used alone, like Al). These are chemically inert in comparison to Ta, but since the rate of oxidation is diffusion limited, even a low thickness element of Ta will survive for the short pulse durations that are needed. Other materials that may be used for the low thickness heating element include tantalum/aluminum alloy, conductive metal nitrides (tantalum nitride, titanium nitride, etc), conductive metal oxides, metal oxy-nitrides, or carbides. The range of thickness for a feasible low thickness heating element is from about 10 angstroms to about 200 angstroms.

In use, some experimentation is needed to determine the voltage and timing of the pulse (or pulses) to be applied to a particular electrical cutting element design for use on a particular tissue type. The current produces heat in the low thickness heating element, and conduction takes heat away. If the current is too high and heat is generated faster than it can be conducted away the electrical cutting element will melt if the pulse duration is long enough. To maximize the conduction of heat into the tissue to be cut, a force such as suction or chemical surface adhesion ensures physical contact between the heater and the tissue. Using a high melting material as the electrical cutting element provides some margin for operation in the event of variable thermal conductivity to the tissue. As soon as vaporization occurs, the thermal conductivity to the tissue drops significantly, and the electrical current must be turned off (or greatly decreased) just prior to this event to prevent melting. In one embodiment, the embedded controller in the hand piece can monitor the temperature of the electrical cutting element by virtue of its increase in resistance as temperature rises, such that current can be reduced as needed to avoid excess temperature). In another embodiment, the determination of operational parameter space begins with the shortest possible pulse that the circuitry can produce (e.g., 1 microsecond) and increases pulse current until a cut is produced (e.g., to a depth of 10 microns, or one cell layer). If no cutting can be achieved, the pulse duration is increased. In a further embodiment, multiple pulses are executed to determine the minimum time (e.g., 1 millisecond) between pulses needed for cooling off. Using this algorithm, the optimum parameter setting can be systematically found for any application (e.g., for a program of 5 pulses to cut through a 50 micron thick membrane).

Since the low thickness heating element is located on the bottom edge of the electrical cutting element only, the sidewalls of the electrical cutting element do not overheat. Thus, a chemical coating on the ID sidewall of the electrical cutting element may persist after the electrical discharge cuts the capsule. A coating that adheres to type IV collagen may hold onto the excised membrane for removal from the eye. One example sequence of events with a collagen adhesive coating on the bottom edge and ID sidewall includes: (1) on initial contact of any location on the bottom edge to the capsule membrane, an adhesive contact area is initiated, and the membrane will then be subjected to the adhesion force that pull it to the bottom edge until the entire circumference is in contact (e.g., 360 degree contact), and (2) the ID coating proceeds to pull the membrane into contact with the ID surface of the electrical cutting element ring, thereby stretching the membrane further until the force from tensile stress balances the force from adhesion. The OD is not coated with too strong an adhesive because it is not desirable to stick to the remaining capsular bag when the device is removed from the eye. The tensile stress from this adhesion process may be small, in which case a suction cup may still needed to assist, or it may be strong enough that a suction cup is not needed.

In the case where naturally occurring internal pressure provides enough tensile stress in the membrane, it is not necessary to add further stress, but simply adhesion for uniform contact. The ID adhesion can be maintained for membrane removal (without suction cup). Collagen may be obtained from natural or synthetic sources to produce the adhesive coating. As the electrical discharge severs the membrane, tensile stress pulls the OD edge of the membrane away from the electrical cutting element, and fluid flows out from the lens (depending on amount of pre-existing internal fluid pressure) through the circular gap.

Fabrication

In one embodiment, a flat sheet of nitinol having an appropriate thickness (e.g., 25 to 50 microns, depending on the application) is used to manufacture an electrical cutting element, such as that used in the embodiments described throughout. A layer of tantalum can be applied to both sides (e.g., by evaporation or sputtering, about 1000 angstroms thick). A layer of tantalum oxide ($Ta_2O_5$) can be produced on both sides (e.g., by depositing more Ta and anodizing it, or by sputtering $Ta_2O_5$ directly) to give an insulating layer. Next, another layer of Ta can be deposited on both sides as an adhesion layer. A layer of tungsten can then be deposited as an anti diffusion layer (this is optional, but may be of interest for applications where prolonged high temperature will be experienced). A layer of gold can be deposited (e.g., typically about 2 microns thick) by evaporation, or sputtering, or plating (on a seed layer). Subsequently, the sheet may be cut (e.g., by laser/water jet) into shapes needed for the particular design. The cut pieces are placed in a fixture that orients the cutting edge towards the sputtering target (or evaporation source). A layer of $Ta_2O_5$ can be deposited (e.g., by evaporation or sputtering) to provide electrical insulation. The pieces are moved up in the fixture to expose about 10 to 100 microns of the sidewalls, and the low thickness heating element is deposited (e.g., by sputtering 100 angstroms of Ta). The electrical cutting elements are removed from the fixture and placed in a shape setting fixture which holds them in the desired ring shape while they are put in a furnace at the shape setting temperature (typically about 500 C) for about 10 minutes (exact time to be determined by testing) and then rapidly quenched in cold water. The electrical cutting elements will now return to their ring shape after undergoing strains of up to about 4 percent. Gold plated leads can be attached by gold to gold diffusion bonding. The lead that spans the gap in the ring holds it together.

FIG. 11B shows the case in which the nitinol is used as one of the electrical cutting elements to carry current to the low thickness heating element, according to one embodiment. In this case, only one side of the nitinol sheet needs to be coated with an insulated layer, and sidewall conducting layer.

In one embodiment, the steps for fabricating electrical cutting elements starting with a planar sheet of polyimide (PI, e.g., kapton) include: an adhesion layer (e.g., Cr) is deposited on each side, then gold is deposited (e.g., 2 microns thick) on both sides. The shapes are cut out and oriented in a fixture with the cutting edge toward the sputtering target. A low thickness heating element is deposited. The parts are removed from the fixture and put into another fixture for attaching the arms (e.g., by gold to gold diffusion bonding).

Current Control for the Low Thickness Heating Element

In some embodiments, the resistance of the low thickness heating element is low due to the short length and relatively wide width of the element. Thus, a small change of voltage will produce a large change in current. This variability in fabrication may require differently applied voltages to produce the needed power for heating different devices containing different electrical cutting elements. Therefore, different devices may be tested after being installed in the hand piece (which can include the support structure), and characterized to determine the required voltage. Circuit elements providing resistance include the leads, thick conductors on the device, and the low thickness heating element itself.

Each device may be characterized by applying a series of short (e.g., a few microseconds) pulses starting at a very low voltage and increasing in small increments to a final voltage below the operational voltage (such that no damage is done to the low thickness heating element). The current is measured for each pulse, and as the voltage increases, the current increases, and the low thickness heating element increases in temperature. In an embodiment, no other circuit element experiences a significant temperature change, thus the resistance change accompanying a higher current is likely due to the low thickness heating element. An analysis of the data may allow the controller to calculate the needed voltage and current for a given device (any combination of applied voltage, current, and/or pulse duration can be used as the controlled parameter(s)). In one embodiment, the device includes a reusable hand piece, thus this testing may all be done with the disposable unit plugged into the hand piece before the suction cup is compressed. In a further embodiment, the testing is performed in around 1-2 seconds.

Figures 23A, 23B:
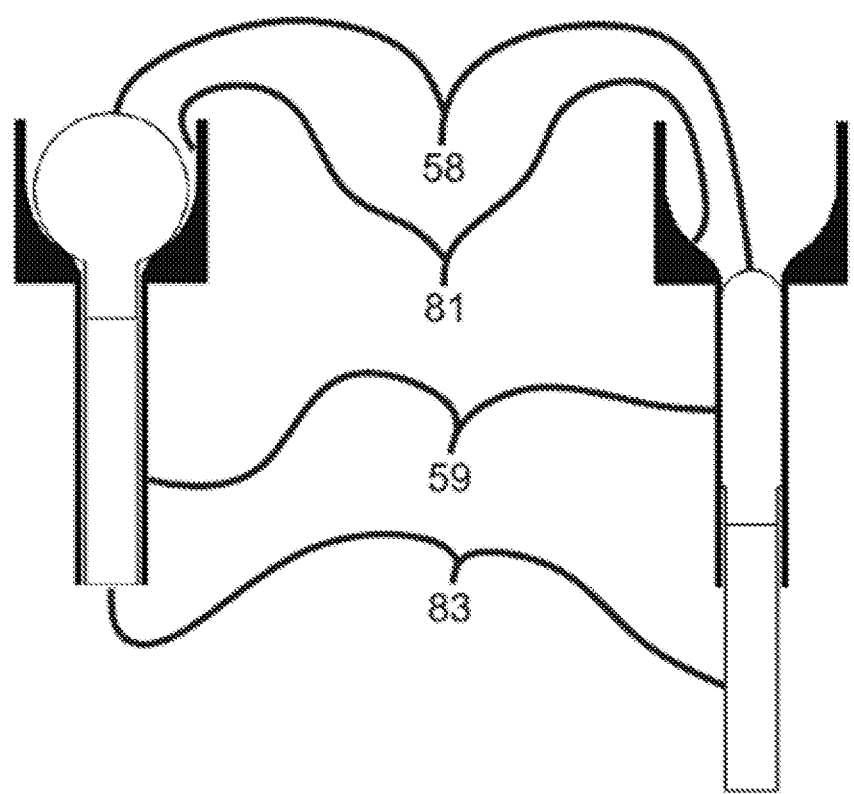
FIG. 23A illustrates a surgical device for performing a capsulotomy, according to an embodiment of the invention.
FIG. 23B illustrates a surgical device for performing a capsulotomy including an inserter, according to an embodiment of the invention.

FIGS. 23A-D show a schematic cross sectional view of the steps of compressing the suction cup/electrical cutting element assembly (58) so that it can be inserted through the corneal incision and into the anterior chamber of the eye, according to one embodiment. FIG. 23A shows the device as packaged, and received by the user. In an embodiment, the electrical cutting element and suction cup are in an as-manufactured stress-free state, and are located within a compression chamber having a roof and a floor that prevent deflection out-of-plane in the plus or minus z direction, and side walls (81) that are calculated to provide the minimum force for the compression step which occurs as the suction cup is pulled into the inserter (59). In a further embodiment, the internal surfaces of the compression chamber are treated to provide the lowest possible coefficient of friction against the silicone suction cup (for example, a fluorocarbon surface such as Teflon) to minimize the dragging force, and to increase the efficiency of operation without requiring the addition of a liquid lubricant.

Figures 23C, 23D:
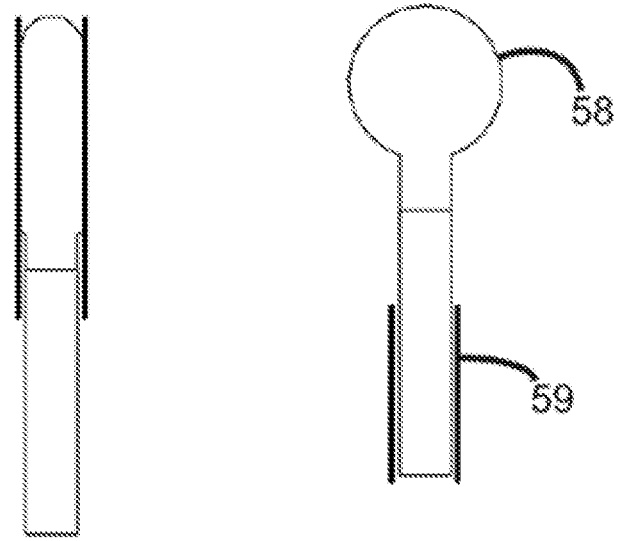
FIG. 23C illustrates a surgical device for performing a capsulotomy including an inserter, according to an embodiment of the invention.
FIG. 23D illustrates a surgical device for performing a capsulotomy including a suction cup, according to an embodiment of the invention.

FIG. 23B shows the device after it has been pulled into the inserter (59), according to one embodiment. In FIG. 23C, the compression chamber has been removed so that the unencumbered tip of the inserter can be inserted into the corneal incision, according to one embodiment. In FIG. 23D, the suction cup has been pushed out of the inserter as it would be when deployed within the anterior chamber of the eye, according to one embodiment. In one embodiment, the device is stored uncompressed because some materials in the device (e.g., the suction cup or potting material) may take a set, or may be too slow to recover their shape after deployment. In an embodiment, if the materials used in the device do not include this limitation, the device may be assembled already compressed in the inserter and ready for deployment. Thus, a user such as a surgeon does not have to spend time performing the compression step.

Mechanism to Provide Suction to Suction Cup

A variety of methods may be used to provide suction to the suction cup, including connecting the suction cup via tubing to powered vacuum pumps located away from the hand piece. In an embodiment, a miniature vacuum pump can be built into the hand piece to accomplish the same function. Additional embodiments include mechanisms such as user-performed, manually activated suction by deforming an expandable and/or collapsible suction bag/bladder/bellows that may be located in the hand piece or attached to the separate suction cup/electrical cutting element assembly that plugs into the hand piece. The suction bag/bladder/bellows is attached and coupled to mechanical levers and linkages. In use, a user may manually push, pull, squeeze, or slide buttons, sliders, or switches to operate these mechanical levers and linkages.

FIGS. 24-47 show embodiments of the device including a suction device located within the hand piece. These embodiments eliminate the suction tube that would otherwise be about 6 feet long reaching to a console. Examples illustrate the suction device riding on the sliding mechanism that the suction cup is also mounted on.

FIGS. 24A-B show methods of producing suction within the hand piece. FIG. 24A is a schematic cross sectional side view of a hand piece at the step in which the suction cup (58) has been compressed and is now located within the inserter (59), according to one embodiment. The compression chamber has been removed in this embodiment, and the tip of the inserter may enter the anterior chamber of the eye through the corneal incision. A single U-shaped knob (111) straddling a tube (97) provides two functions by sliding parallel to tube (97) towards the proximal direction to compress, or in the distal direction to deploy, the suction cup, and move perpendicular to the tube (97) to provide suction (or out-flow when released, allowing the elastomeric component of the bellows (112) to contract).

In FIG. 24A, a knob (111) has been slid back to the proximal end of a guiding slot (110), according to one embodiment. In FIG. 24B, the knob (111) has been slid to the distal end of slot (110) and pushed perpendicularly to the tube to rotate a bellows rigid support wall (115) which expands a bellows (112) to create suction to the suction cup through a port (114). Constraining guides (not shown) in the handle (131) may prevent transverse (i.e., perpendicular to the tube) motion of knob (111), except when it is in the distal-most position with the suction cup deployed. The elastic strain energy of the bellows (and its more rigid supports) may automatically return it to the deflated low volume state as a user releases the knob (111). In an embodiment, an electrical cable (98) is also attached to and travels with the slidable unit.

FIGS. 25-47 show embodiments for strategies of the disposable suction cup/electrical cutting element/suction bellows unit of the invention. FIGS. 25-27 schematically show basic concepts, while FIGS. 28-47 show detailed representations of actual engineered designs. FIG. 25A shows a schematic cross sectional view of an embodiment of a disposable unit (130) having a compression chamber (120), a latch (122), a latch release lever (121), a suction cup (58), a compressing ramp (81), an inserter (123 seen in cross section), latching sockets (128), vacuum indicator (126), upper bellows (or bladder) rigid support (125), lower bellows (bladder) rigid support (124), tapered insertion end (129). In one embodiment, the disposable unit is removed from a sterile package and plugged into the distal end of the reusable hand piece. The guiding contours of the hand piece mechanically find the tapered latches (122) and the tapered tip (129) of the suction system. As the insertion progresses, compliant electrical connectors in the hand piece make electrical contact to the electrical leads (not shown) of the disposable unit, latches in the hand piece securely grip the inserter (123), and a slidable knob engages latching sockets (128).

FIG. 25B shows a schematic side view of the suction cup/bellows unit in a low volume state, according to one embodiment. FIG. 25C shows a side view with the bellows expanded, according to one embodiment. Fluidic communication between the suction cup and the bellows may occur through port (127). In one embodiment, the bellows are expanded in an as-packaged, stress-free state of the device. In a further embodiment, as the unit is plugged into the hand piece, the mating contours of the hand piece compress the bellows to force clean packaged air out through the lumen (131) and suction cup to ensure that there is no blockage. If there is a blockage, then the pressure in the bellows may increase, and the vacuum indicator (126), a circular patch of the elastomeric bellows that is free to deflect under applied pressure, will bulge outwards. This bulge may be detected by a sensor, which may generate a reject alarm. The sensor may be an optical, electronic, or mechanical sensor, which is part of the reusable hand piece.

FIG. 25C shows a vacuum indicator bulging inwards as it is when the suction cup sealing surface (44) has sealed against the lens capsule with the bellows in the compressed state and the bellows has been expanded, according to one embodiment. In an embodiment, the magnitude of the deflection of the circular patch of membrane must exceed a predetermined threshold to indicate adequate suction before the electronics enable completion of the operation. Also, the rate of change of the deflection may be monitored for a prescribed length of time (e.g., 2 seconds) to check for excessive leakage. In a further embodiment, if the rate of decrease of suction is below a predetermined limit, then the leak rate will be considered acceptable and the completion of the operation will be enabled. An audible ready signal may sound to let the user know that the discharge may now occur. In one embodiment, the dead volume of the system in its deflated state is low to minimize the amount of air initially in the system that reduces the maximum suction that can be applied.

In an embodiment, the elastomeric suction cup/bellows (bladder) is molded as one piece, with the proximal tip to be sealed after removal from the mold. In another embodiment, the suction cup and bellows are molded separately as two independent components. In some embodiments, rigid walls are required to expand or compress the bellows, including the top wall (125) which has a hole in it to create the vacuum indicator (126), and the lower wall (124) which is rotatable about the proximal hinge (129).

Figures 26A, 26B, 26C:
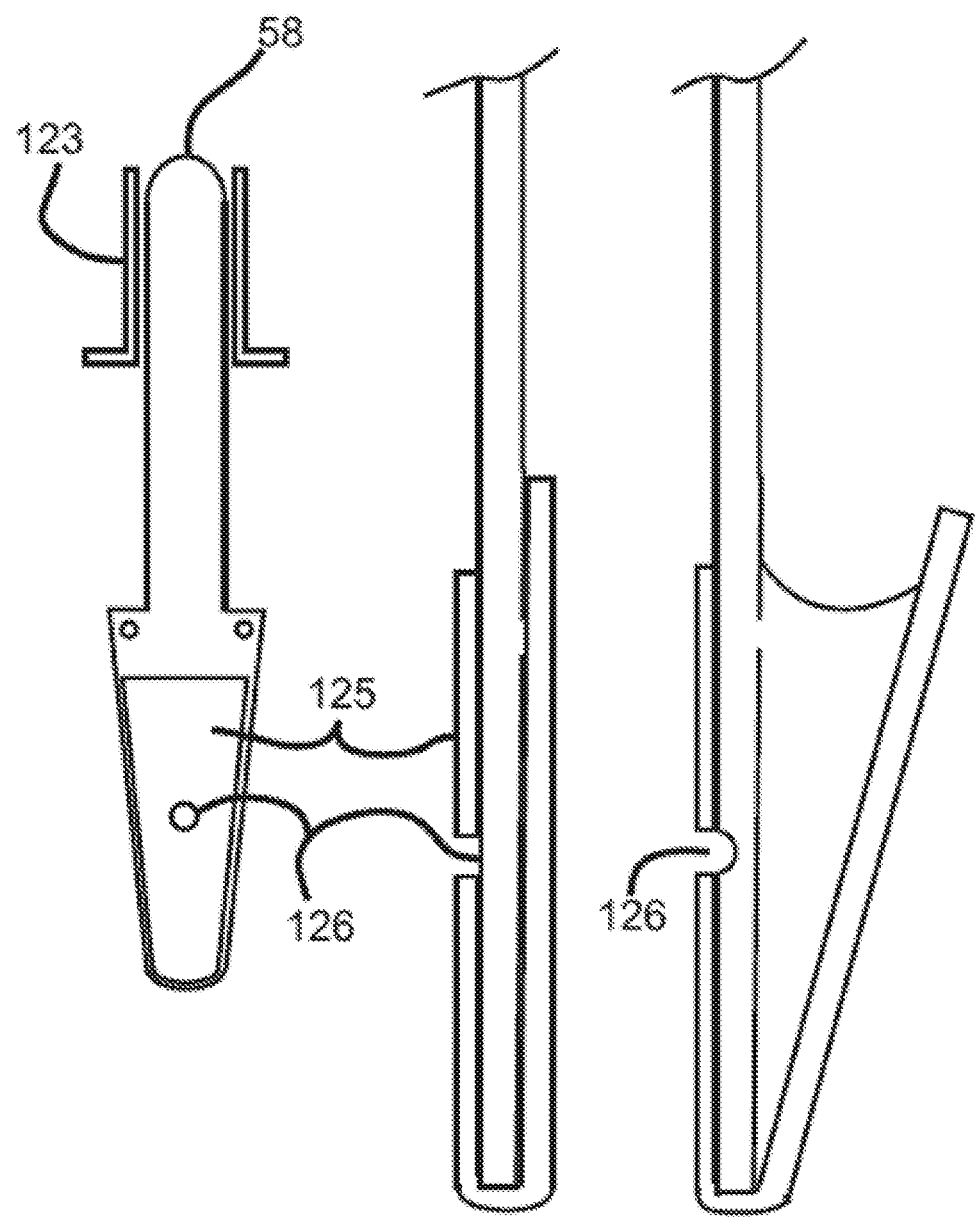
FIG. 26A illustrates a surgical device for performing a capsulotomy, according to an embodiment of the invention.
FIG. 26B illustrates a close-up side view of a bellows of a surgical device for performing a capsulotomy, according to an embodiment of the invention.
FIG. 26C illustrates a close-up side view of a bellows of a surgical device for performing a capsulotomy, according to an embodiment of the invention.
Figure 27:
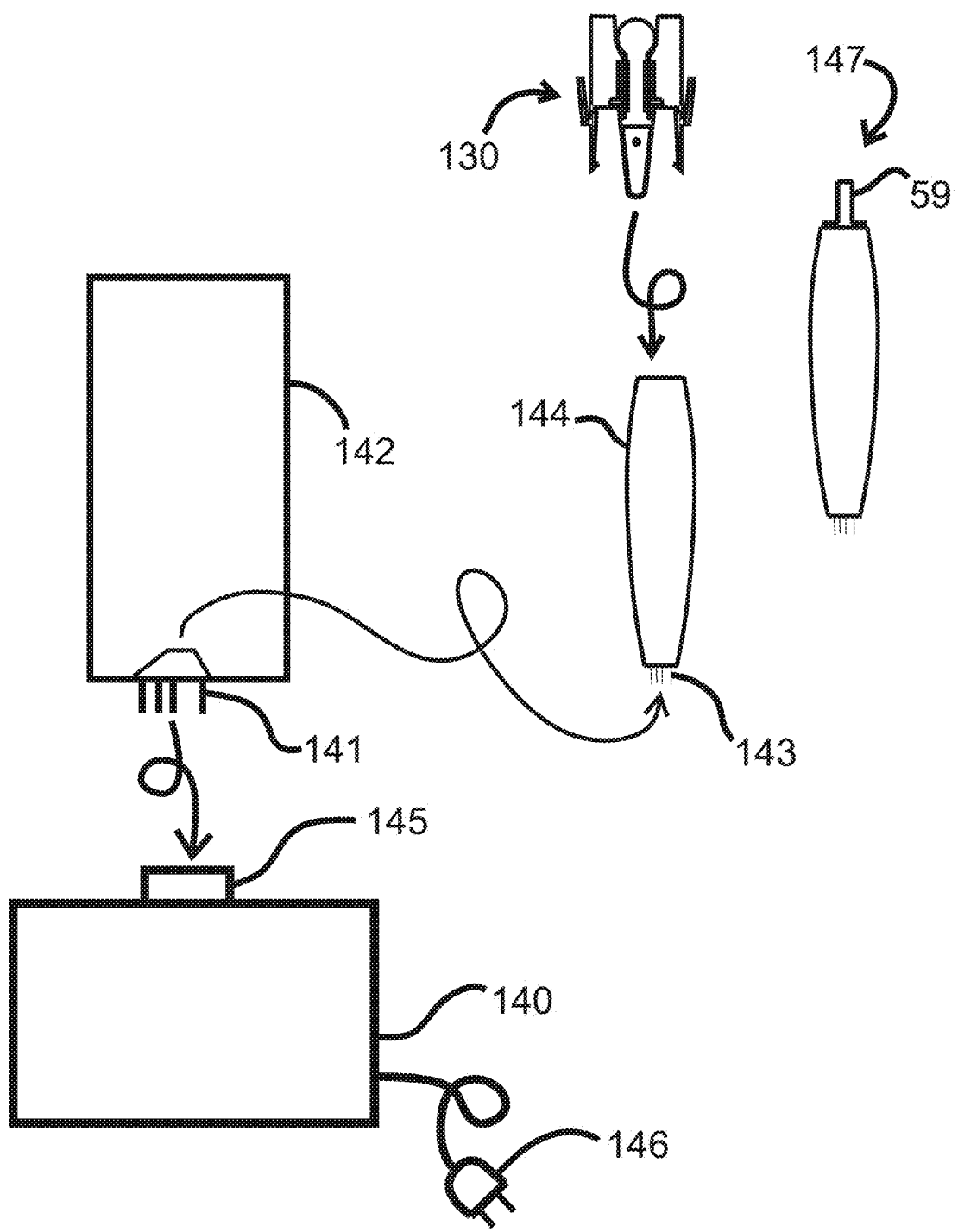
FIG. 27 illustrates a surgical device for performing a capsulotomy including a support structure and a docking station, according to an embodiment of the invention.

FIG. 26A shows an embodiment of the unit after the suction cup (58) has been compressed, pulled into the inserter (123), and the compression chamber removed (by pressing release levers 121 to move latches 122 out of the sockets (254 see FIG. 39) in the handle that were anchoring them, and pulling it away).

FIGS. 26B and 26C show side view close ups of embodiments of the bellows action. In FIG. 26B, the bellows is compressed by insertion into the hand piece, and the flat condition of the vacuum indicator (126) shows that the air flowed out, so the lumen is not blocked and the operation can proceed, according to one embodiment. In FIG. 26C, the sealing surface (44) (see FIG. 25B) of the suction cup (58) is sealed against the surface of the lens capsule, and as the bellows expands, suction is successfully created as shown by the inward bulge of the vacuum indicator (126).

In one embodiment, a reusable hand piece and reusable cable (which is also sterilizable) are used. When the device is used in an operating room, for example, the cable (typically about 6 feet long) may bridge the space from the sterile field where the sterile instruments (including the hand piece and disposable suction cup unit) are organized, to the nonsterile environment where the console is located. Therefore, an in embodiment, one end of the cable is plugged into the hand piece and the other end is plugged into the console which provides power, and some, or all, of the electronic control functions to the hand piece.

In an embodiment, the hand piece is designed for use as a free standing unit without the encumbrance of wires or tubing going to a console. FIG. 27 shows a hand piece (144), a docking station (140), a sterile enclosure (142) with electrical feed through (141, so the whole docking station does not have to be sterile) and the disposable unit (130) which may be packaged in a sterile package, according to one embodiment. In an embodiment, the hand piece may be plugged into an electrical feed through in a sterile enclosure which in turn is plugged into an electrical connector (145) of a docking station, when the hand piece is not in use. In another embodiment, a simple sterilizing bag may contain the hand piece, and then after sterilization, electrical pins 143 of the hand piece can puncture the bag and poke through as needed to plug into the electrical connector (145) of the docking station. If the docking station must be in a non-sterile area, then a cable may be used to connect the pins (141) to the connector (145). In another embodiment, all docking functions are completed prior to sterilization, such that the hand piece can be sterilized in a closed sterilization bag, and can remain in the bag until needed.

In some embodiments, the functions performed by the docking station include pre-charging the high voltage capacitor (which provides the current for the tissue cutting discharges), pre-charging a low voltage super capacitor (which provides power for the electronic circuitry in the hand piece), uploading data from the embedded microcontroller in the hand piece, or downloading data or new programs to the embedded microcontroller or its firmware. The docking station may have a plug (146) for a wall outlet, and can connect to the local computer through a wired or wireless network. After each use, the reusable hand piece may be plugged into the enclosure (142) which allows the sterilizing agent to penetrate its walls to sterilize the hand piece and the enclosure. The hand piece may contain wireless communication capabilities (e.g., blue tooth) to communicate with a foot pedal (e.g., to trigger a discharge) or with the docking station, or with another computer. In some embodiments, the hand piece may include status indicators (e.g., light emitting diodes), and an audio device to generate audible signals (e.g., ready to fire, or alarm if device is not usable). In other embodiments, a battery may be used instead of a super capacitor to power the electronic controls of the hand piece. One ready-to-use configuration (147) shows the suction cup pulled into the inserter, the compression chamber removed, and the tip of the inserter available to enter the eye.

In one embodiment, a list of components for inclusion in the hand piece include: (1) high voltage capacitor (e.g., 50 to 100 V for electrical cutting element discharge), (2) super capacitor (e.g., 3 volt 20 farad, to power electronics), or a battery (e.g., AAA or AA), (3) control circuitry (microcontroller etc), (4) status indicators (leds) (5) audio beeper (6) latching interlocks to prevent out of sequence operations, and (7) suction pressure detector.

In one embodiment, the hand piece is connected to a console by a two conductor cable (note that it may have more than two conductors), which may have a very low thickness because the average current is small. In an embodiment, a thin cable is desirable because it has a low stiffness and low weight to minimize interference with any effort from a user in manipulating the hand piece. The cable may be permanently attached to the hand piece, or detachable at a connector. As described previously, the cable may span the distance from the sterile field to non-sterile surroundings (the hand piece being confined to the sterile field, and the console residing in the non-sterile realm). In one embodiment, the entire cable is initially sterile, and begins in the sterile field. However, the end pulled from the sterile field to be plugged in to the console becomes non-sterile. The cable provides electrical current to charge the high voltage capacitor (e.g., 50 to 100 volt, for cutting), and to operate the electronic circuits that control the device, and wireless communication. This may eliminate the need for a battery or super capacitor in the free standing hand piece that operates without a cable. The high voltage capacitor is preferably kept in the hand piece to shorten the leads for the electrical discharge. In an embodiment, adding a third conductor to the cable provides a dedicated line to charge the high voltage capacitor may simplify the electronics in the hand piece, although this causes an increase in the weight and stiffness of the cable.

Figure 28:
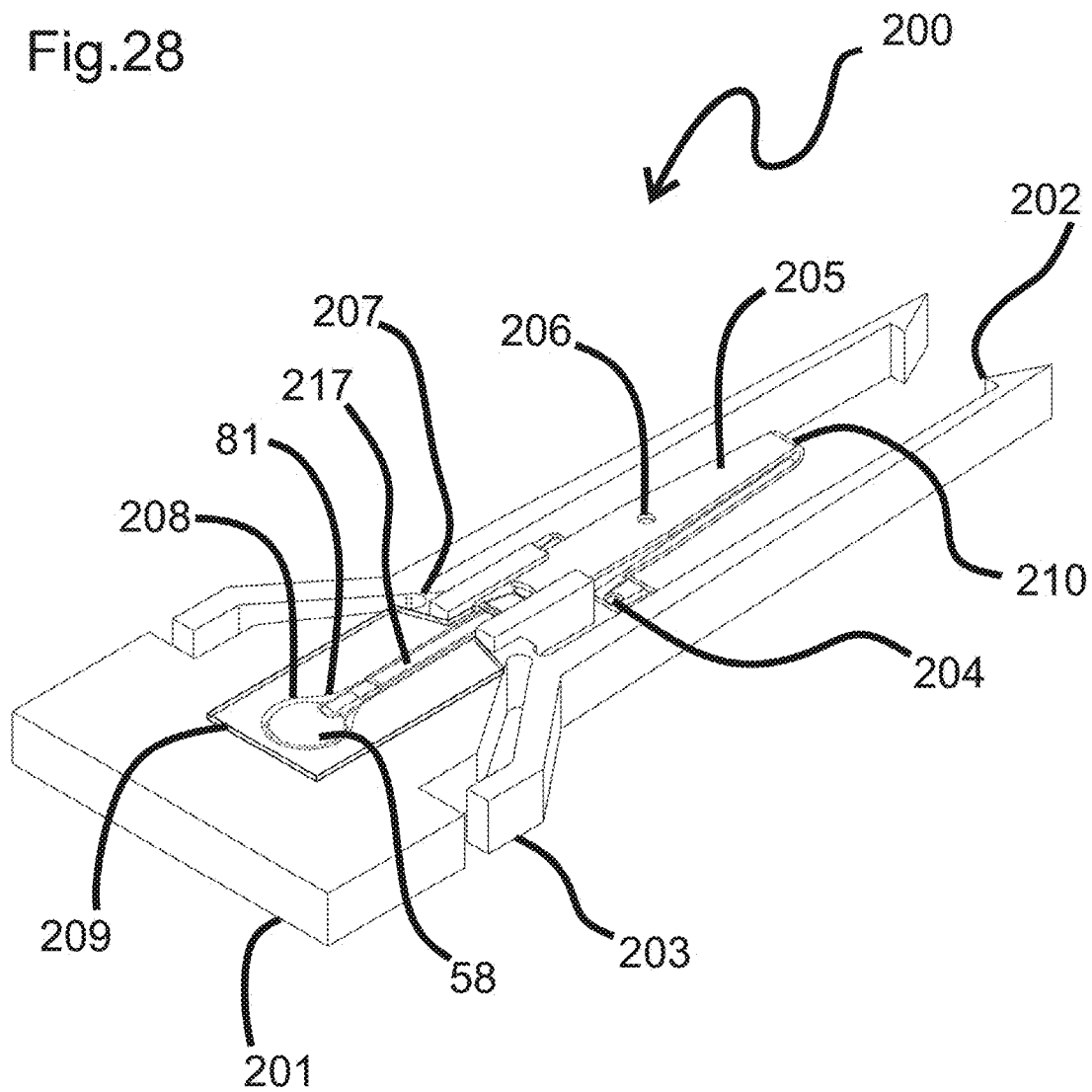
FIG. 28 illustrates a surgical device for performing a capsulotomy including a disposable unit, according to an embodiment of the invention.

FIGS. 28-47 show embodiments of a disposable unit, a reusable hand piece, and a reusable cable. FIG. 28 shows the disposable unit (200) as received by the user, according to one embodiment. The suction cup (58) is in its stress free state in the compression chamber (208) of the compressor (201). In an embodiment, when a user slides the disposable unit into the hand piece, latches (202) will lock on to the hand piece, and the tapered end (210) of the suction bellows substantially rigid (but sufficiently flexible) support will enter the guiding features internal to the hand piece. A hinge (207) allows in-plane rotation of a latch (202) while preventing out-of-plane movement. After the suction cup has been pulled into the inserter (217), release levers (203) will be pressed to unlatch the latches (202) so that the compressor can be taken away. A transparent roof (209) over the compression chamber, and the floor of the compression chamber (visible in FIG. 29) prevent out-of-plane deflection of the suction cup during compression.

Figure 29:
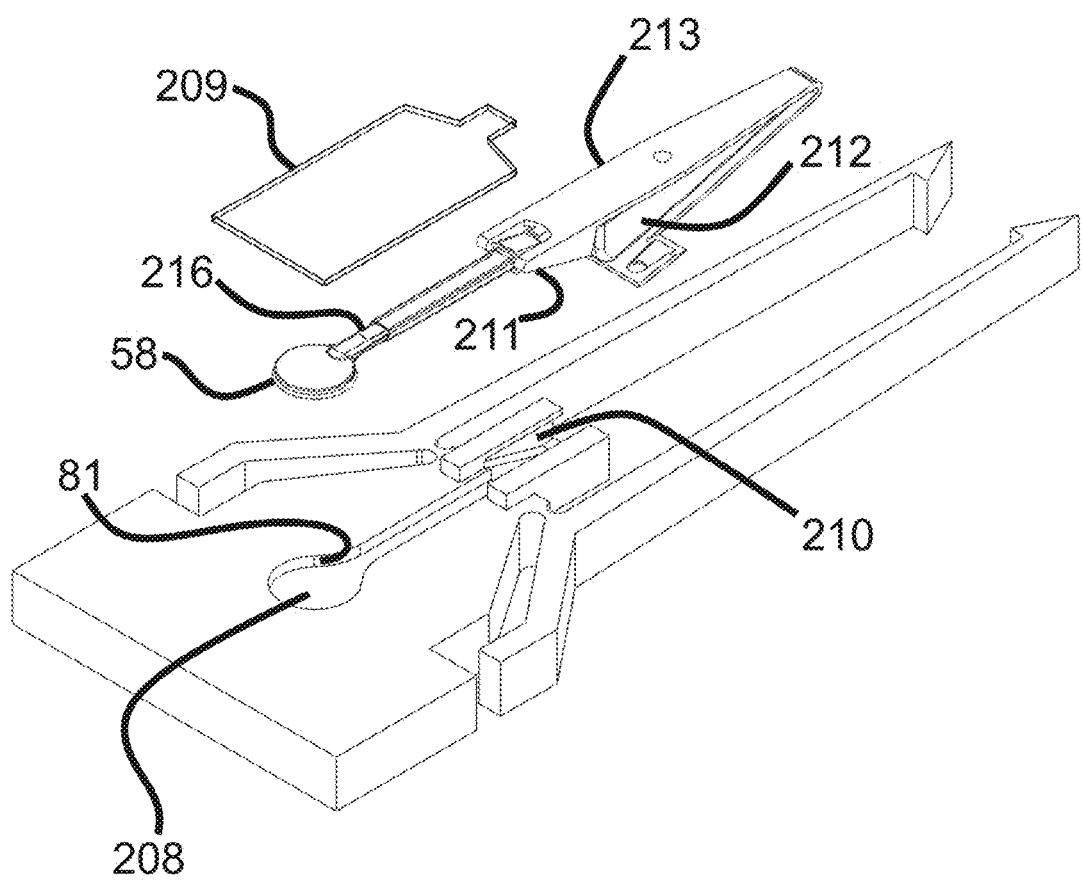
FIG. 29 illustrates an exploded view of a surgical device for performing a capsulotomy including a disposable unit, according to an embodiment of the invention.

FIG. 29 shows an exploded view of the disposable unit, according to one embodiment. In an embodiment, the suction bladder (212) has an initial volume of clean packaged air, as received. The passive guides inside the handle compress the bladder when it is inserted to provide a means to verify that the lumen to the suction cup is not plugged. As received, wedge (211) may be latched into a socket (210) to hold the compressor to the suction cup/suction bladder unit. It is a detent that can passively release when pulled apart with a small but deliberate force. In a further embodiment, when a user inserts the disposable unit into the hand piece, an inserter latch (222, FIG. 35) secures the inserter (217) so that it will not move relative to the handle during the operation.

Sequence of Operation

In one embodiment, once the suction cup/electrical cutting element assembly has been attached to the hand piece, the sequence of operation is as follows: a user slides a knob (218) on the hand piece within constraining slot (219), and the feet of the knob slide up the ramp (226) (see FIG. 31) on the incoming disposable unit and lock into sockets (240). After the disposable unit is completely installed into the handle, the user can slide the knob (218) to the proximal end of slot (219), causing the suction cup (58) to be compressed by the converging sidewalls (81) of the compression chamber, and drawn into the inserter (217) (see FIG. 33). The next step is to press the levers (203) towards each other to release latches (202) from the handle and pull the compressor away from the handle leaving the disposable suction cup system installed in the hand piece. These steps may be used if the suction cup is provided to the user in an expanded shape (i.e., deployed). Alternatively, the suction cup can be pre-loaded into the inserter for the user. In this case, device compression and sliding into the inserter may be performed prior to the packaging of the device, so that the user does not have to perform the steps described above.

In an embodiment, the tip of the inserter is inserted through a corneal incision into the anterior chamber of the eye. After the inserter tip has been pushed through the corneal incision, the knob (218) can be slid in the distal direction to deploy the suction cup in the eye. A user of the device can center the suction cup on the optic axis of the lens and bring the sealing surface (44) into contact with the lens capsule. A knob (218) can then be pushed down to expand the suction bladder (212) and to create a suction force that causes the suction cup to press the electrical cutting element (e.g., 250 in FIG. 30) against the capsular membrane. The electrical discharge may then occur to cut the membrane, after which the suction cup may be pulled back into the inserter by sliding knob (218) back again in the proximal direction. No compressor is needed because perfect packing in the inserter is no longer important. The device can now be removed from the eye.

Figure 30:
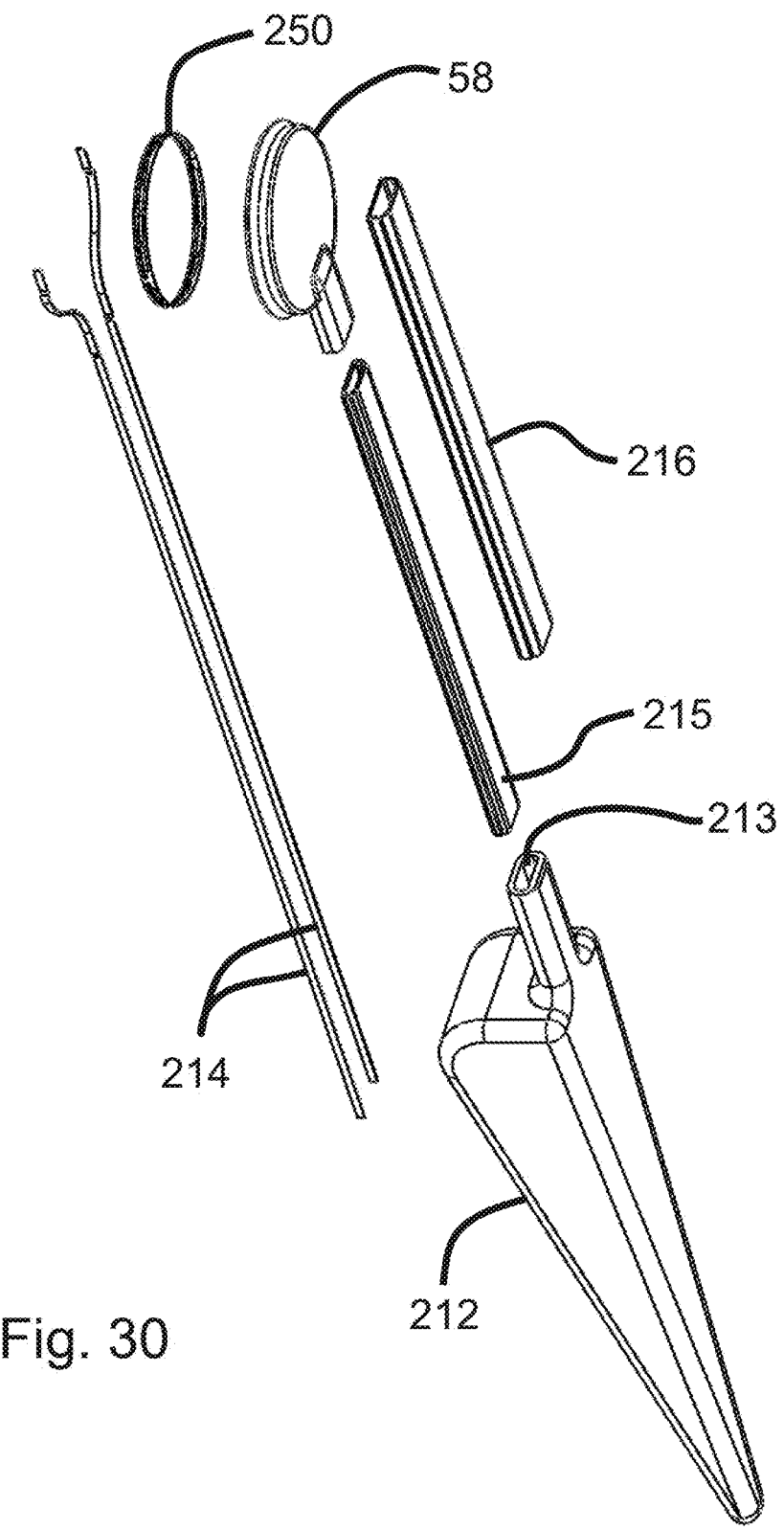
FIG. 30 illustrates an exploded diagram of a portion of a surgical device for performing a capsulotomy including a suction cup and an electrical cutting element, according to an embodiment of the invention.

FIG. 30 shows the components that comprise the suction system, according to one embodiment: suction cup (58), rigid tube (215), heat shrink tubing (216), suction bladder (212), and electrical cutting element leads (214), and electrical cutting element (250). For this construction, the neck of the suction cup can slide over the outside surface of the distal end of the rigid tube. The neck (213) of the suction bladder can slide over the outer surface of the proximal end of the rigid tube. The distal ends of the leads (214, which make the electrical connections to electrical cutting element 250) can penetrate the side wall of the suction cup and be sealed by potting material (e.g., silicone) so no leakage develops. Finally the heat shrink tubing (216) may be shrunk by heating, and clamp the other components (which are inside it) securely in place.

Figure 31:
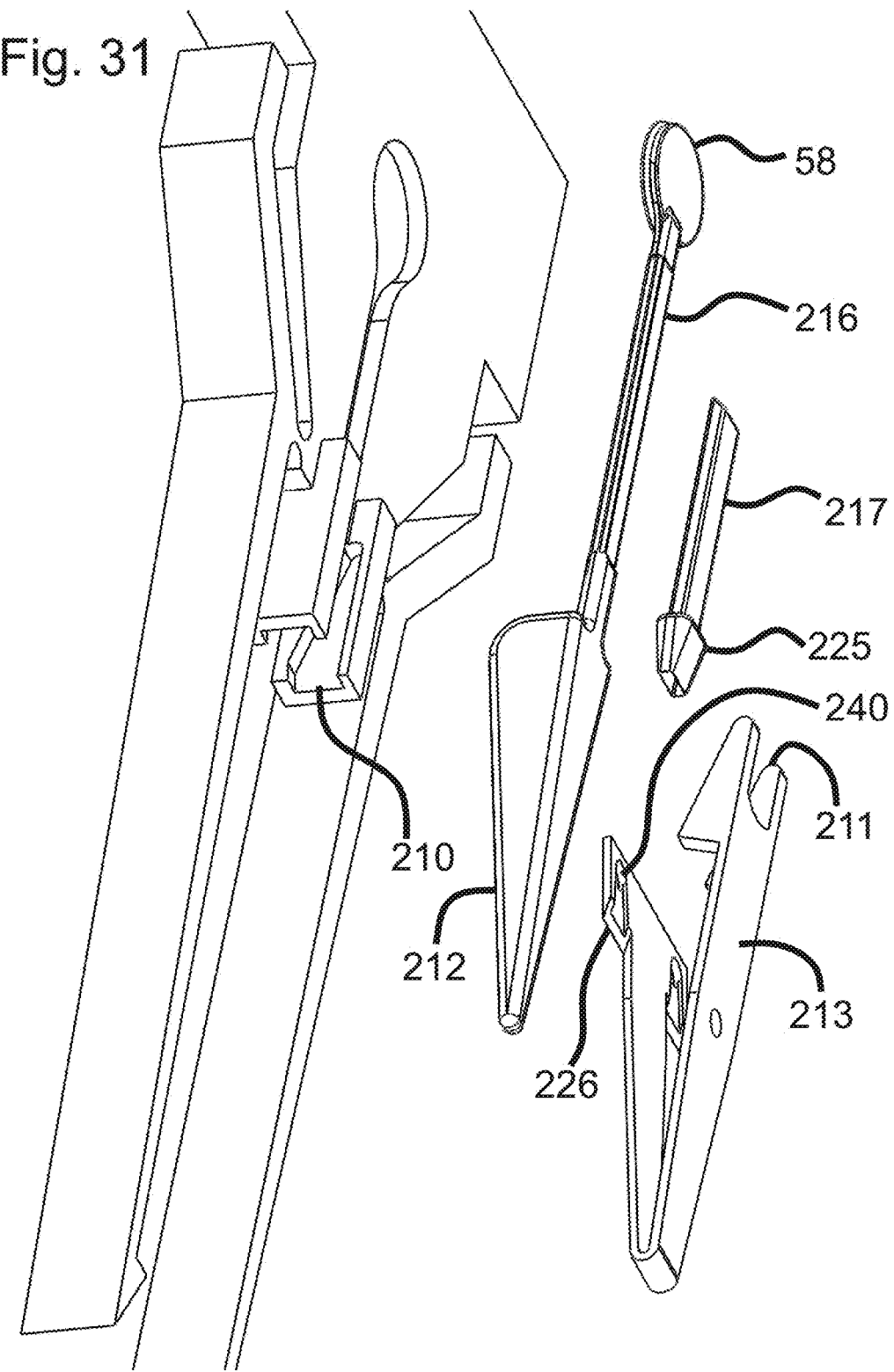
FIG. 31 illustrates an exploded diagram of a portion of a surgical device for performing a capsulotomy including a suction cup and an electrical cutting element, according to an embodiment of the invention.

FIG. 31 shows a partially exploded view in which the components in FIG. 30 have been assembled, but the inserter (217), rigid walls (213), and compressor (210) are shown separately, according to one embodiment. When fully assembled, the top and bottom walls of the suction bladder are bonded (e.g., by silicone adhesive) to the corresponding rigid wall of (213), and heat shrink tubing (216) lies inside the lumen of the inserter (217). The tapered structure (225) of the proximal end of the inserter (217) is secured by the inserter latches (222) of the handle. FIG. 31 also illustrates sockets (210), wedges (211) that reversibly engage the sockets, and ramps (226) that mechanically find the feet of the knob (218) to guide them to lock into sockets (240).

Figure 32:
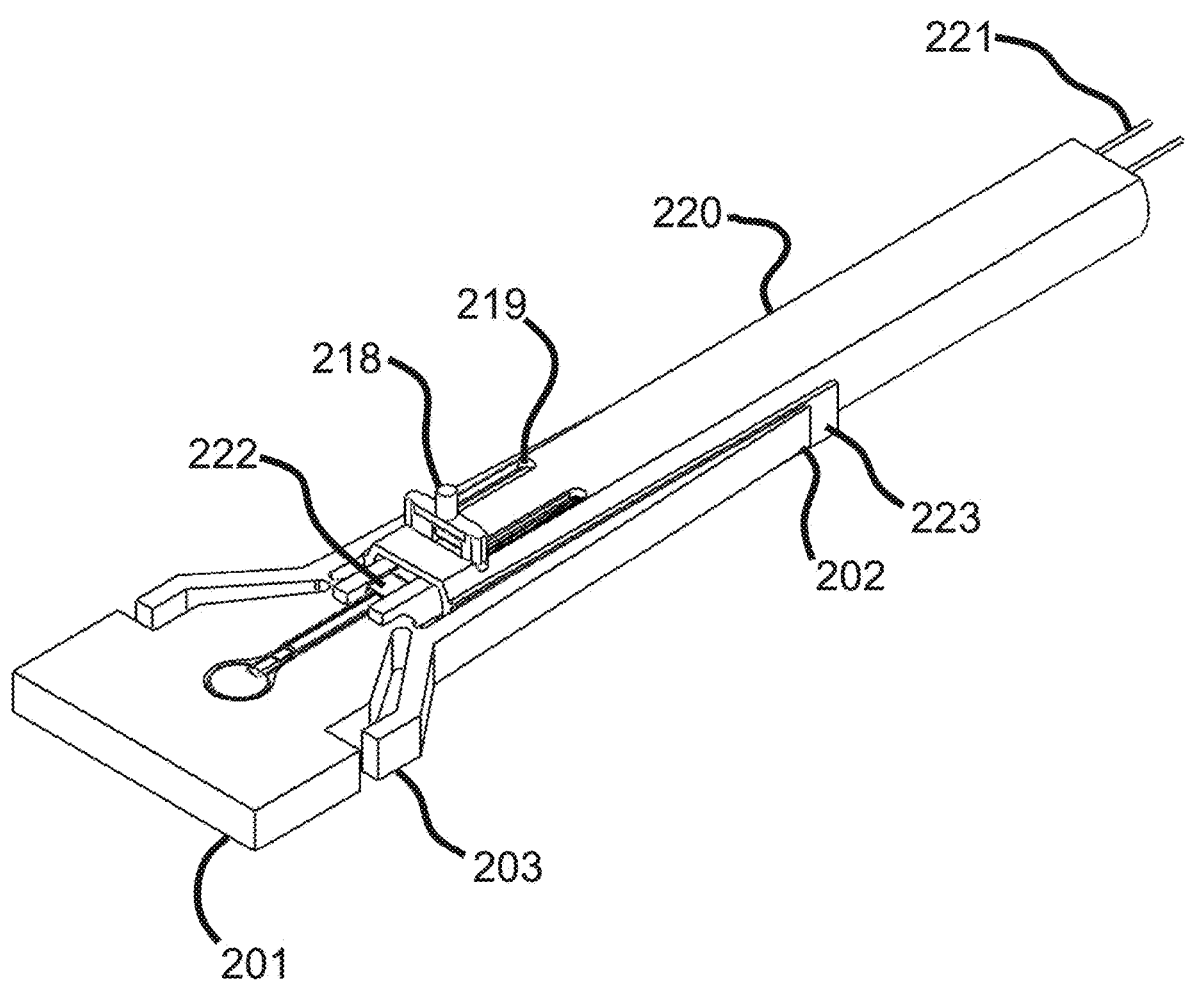
FIG. 32 illustrates a perspective top view of a disposable unit and support structure of a surgical device for performing a capsulotomy, according to an embodiment of the invention.
Figure 33:
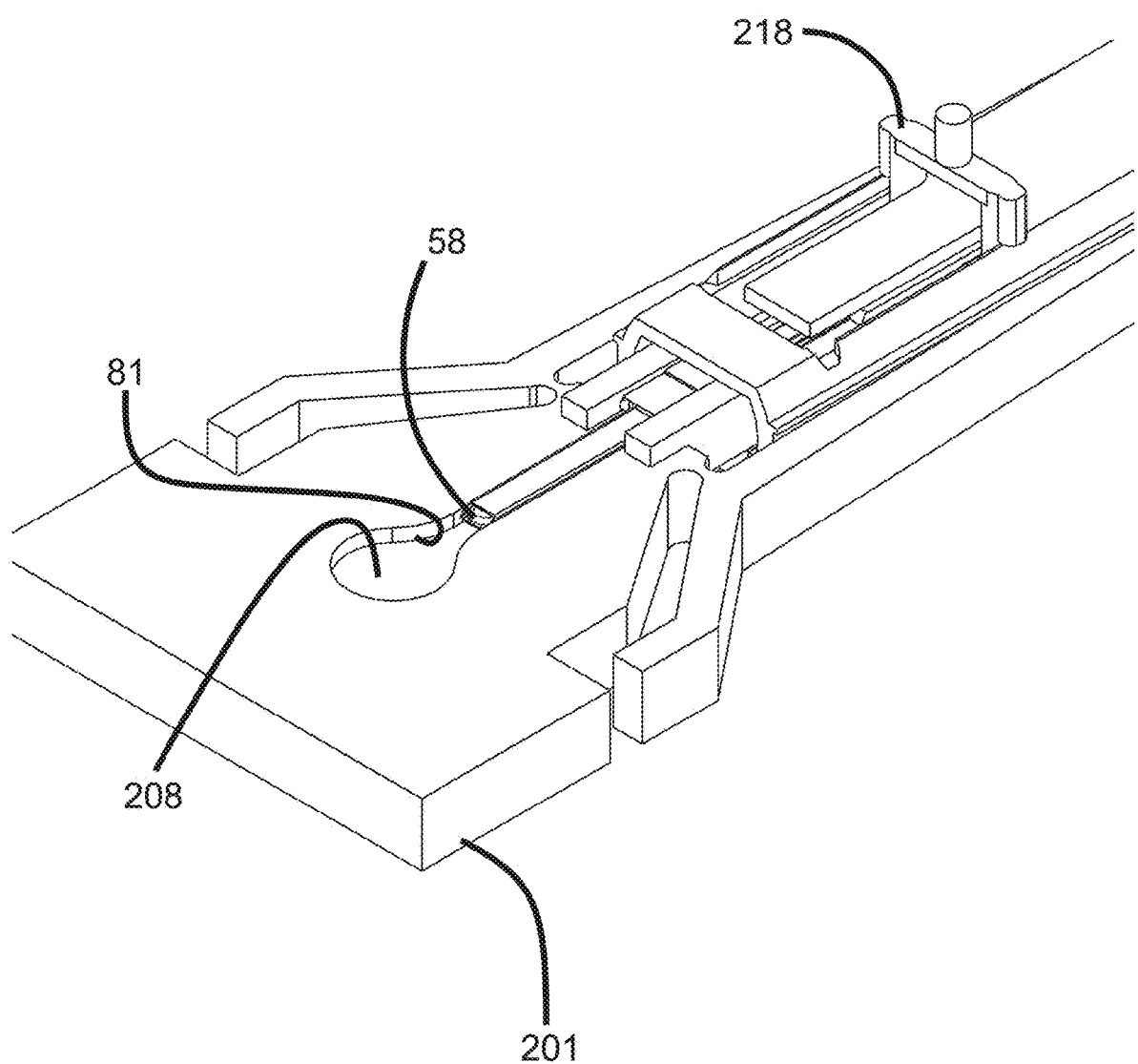
FIG. 33 illustrates a close-up perspective top view of a disposable unit and support structure of a surgical device for performing a capsulotomy, according to an embodiment of the invention.

FIG. 32 shows a perspective top view of the disposable unit latched on to the reusable hand piece, according to one embodiment. The reusable cable (not shown) may plug into the electrical connectors (221) at the proximal end of the hand piece. FIG. 33 shows a close up view of the disposable unit, according to one embodiment. In this embodiment, the suction cup has been compressed and pulled into the inserter (the distal end of the compressed suction cup (58) can be seen within the lumen at the tip of the inserter), and the knob (218) has been slid proximally.

Figure 34:
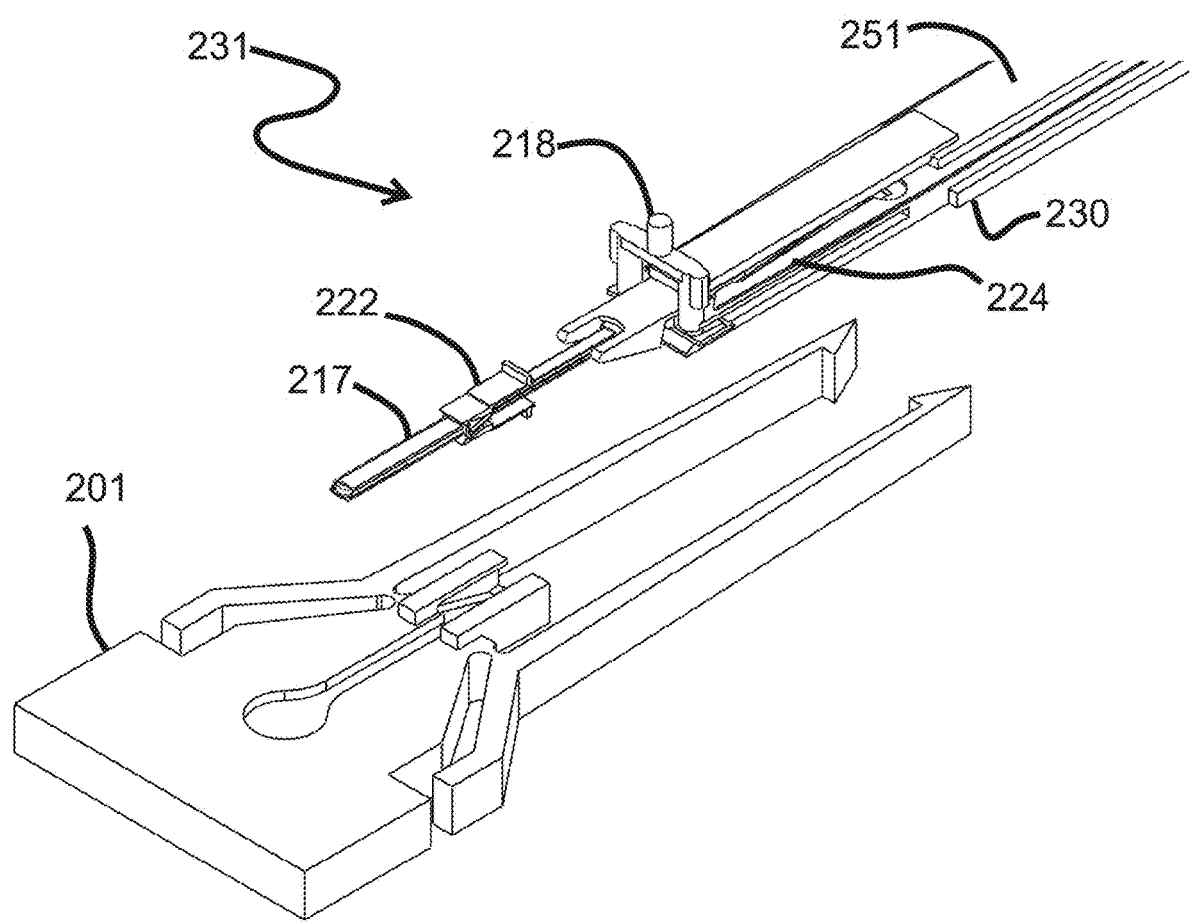
FIG. 34 illustrates a close-up perspective top view of a disposable unit and support structure of a surgical device for performing a capsulotomy, in which a compressor has been removed from the support structure, according to an embodiment of the invention.

In FIG. 34, the compressor (201) has been removed from the reusable hand piece, according to one embodiment. The handle is not shown so that the internal components are visible. In an embodiment, the hand piece is comprised of a sliding unit (231) and fixed unit. The fixed unit is made up of the handle (220) (not shown), the inserter latches (222), and the disposable inserter (217). The sliding unit includes a block (251) having ribs (230), which engage grooves on the ID of the handle to allow sliding without rotation. The sliding unit also includes compliant electrical contacts (224) to engage the electrical leads (214 in FIG. 30) on the disposable unit, and a knob (218) that is cantilevered from the block to allow vertical motion. The space between these components may form a cavity to receive and compress the disposable suction bladder.

Figure 35:
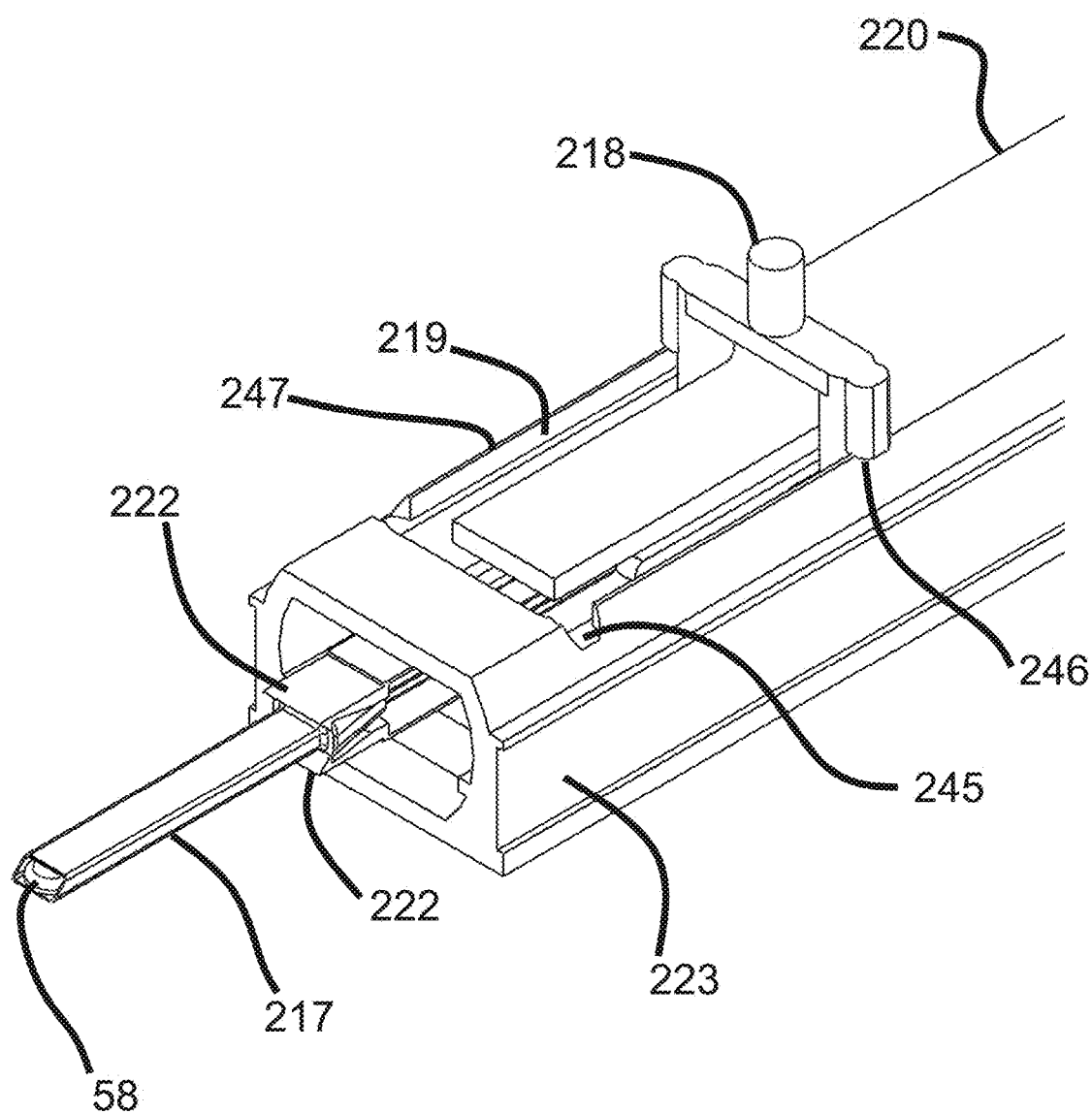
FIG. 35 illustrates a close-up view of a support structure of a surgical device for performing a capsulotomy, according to an embodiment of the invention.

FIG. 35 shows a close-up of the hand piece ready to insert the tip into the eye, according to one embodiment. In this embodiment, the distal end of the compressed suction cup (58) can be seen within the lumen of the inserter (217), and the knob (218) is at its most proximal position. The guides (223) for engaging the latches of the compressor can be seen since the compressor has been removed from the handle (220). Cutouts (245) in the handle allow knob standoffs (246) to go down when pushed to create suction only when the knob is at its distal-most position, since the suction cup should be deployed before suction should be applied. In a further embodiment, the standoffs at all other positions slide against rails (247), such that the knob (218) cannot be pushed down. The inserter latches (222) are cantilevered from the handle (220) and do not move with the sliding unit.

Figure 36:
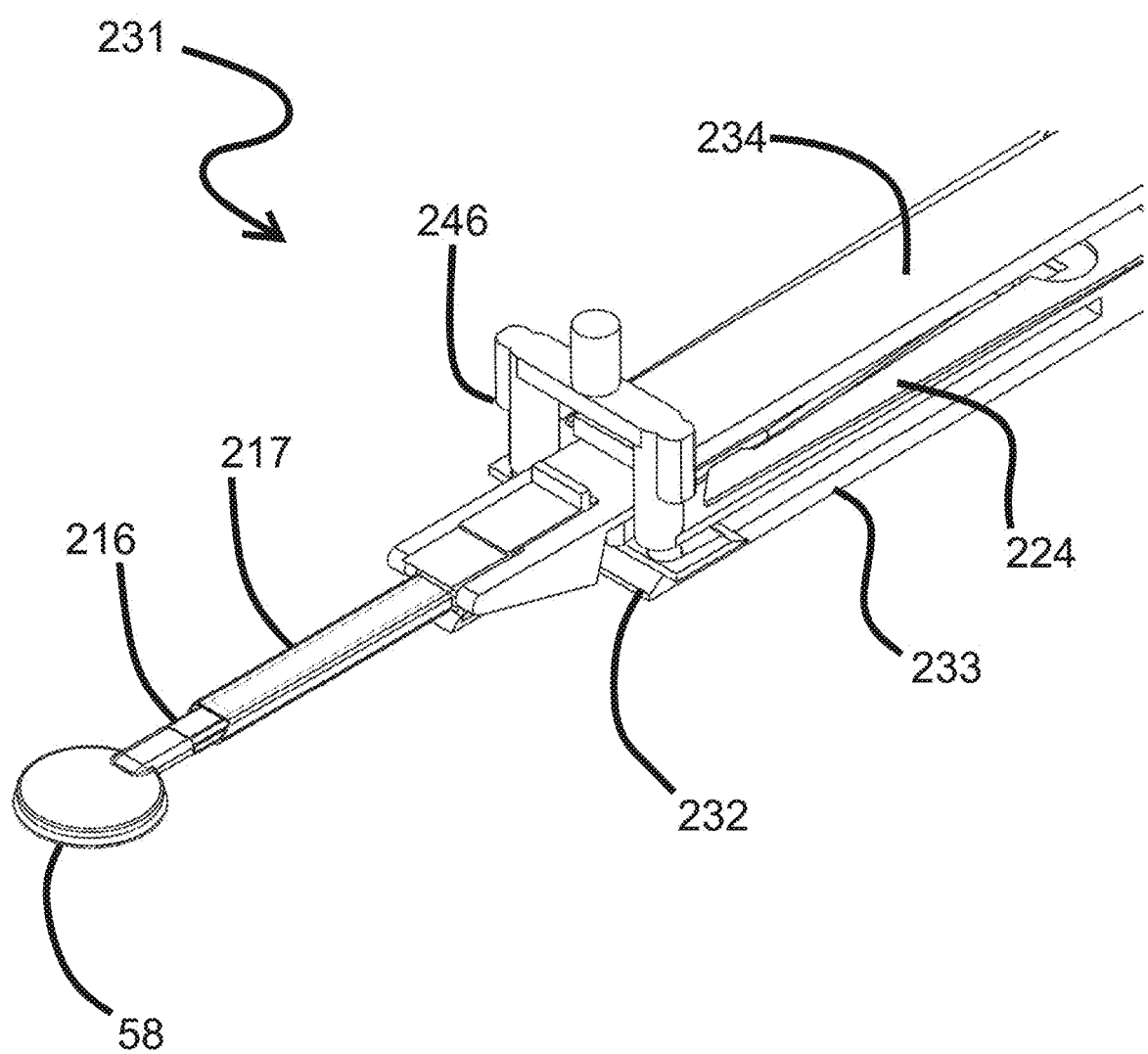
FIG. 36 illustrates a suction unit of a surgical device for performing a capsulotomy, according to an embodiment of the invention.

FIG. 36 shows the suction bladder unit inserted into the sliding unit and compressed by the sliding unit, according to one embodiment. The insertion motion is mechanically guided on the disposable side by the tapered end (210) of the suction bladder wall assembly and by the tapered ramp (226), and on the hand piece side by the tapered ramp (232) and the compressing cavity defined by the roof (234) and floor (233), which are both cantilevered from the sliding block (251). In an embodiment, the floor (233) is not extremely rigid, and can be deflected downwards by a user pushing down on knob (218) to create suction, and then provide spring back force to create outflow when the knob is released.

Figure 37A:
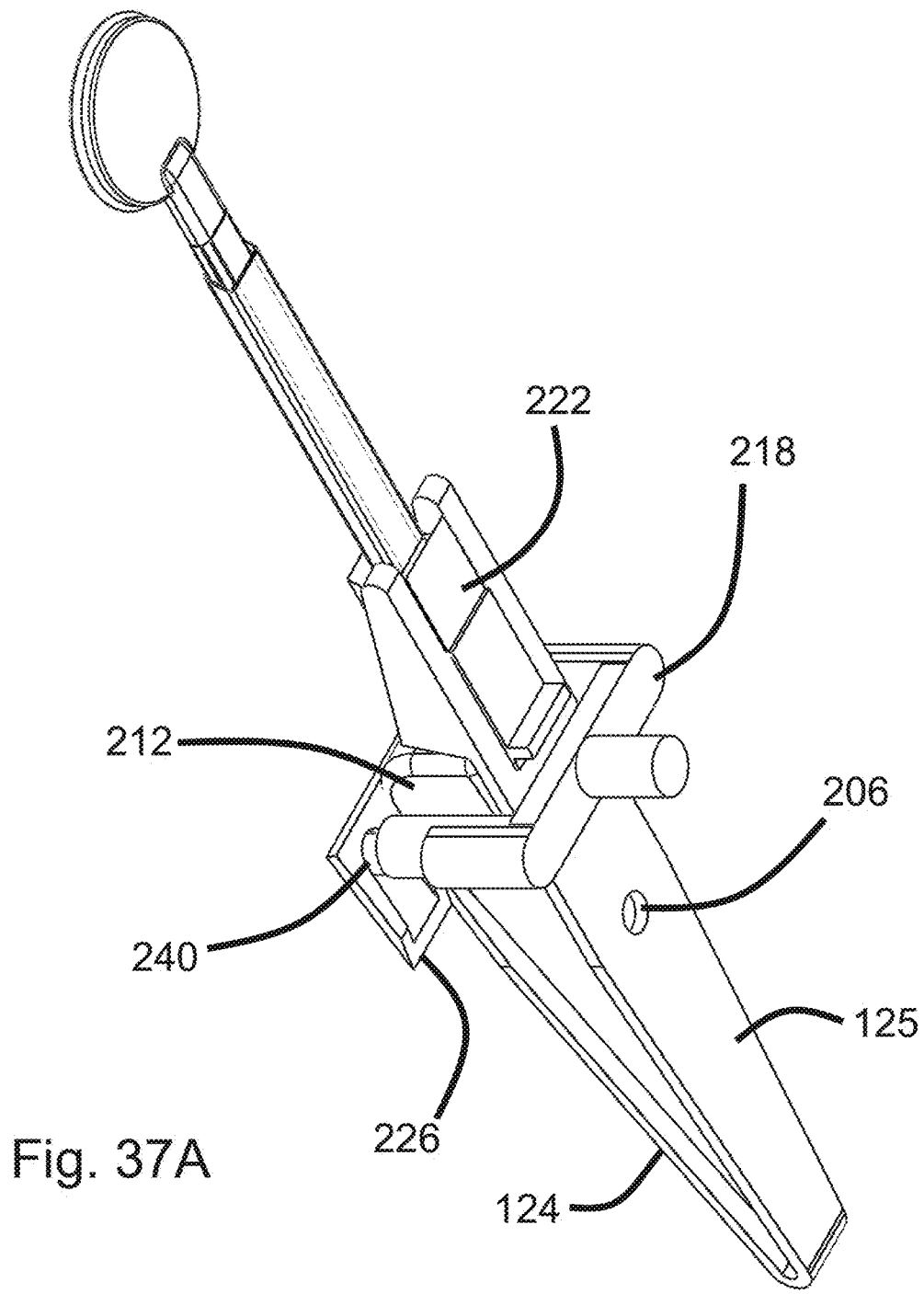
FIG. 37A illustrates a suction unit of a surgical device for performing a capsulotomy, according to an embodiment of the invention.
Figure 37B:
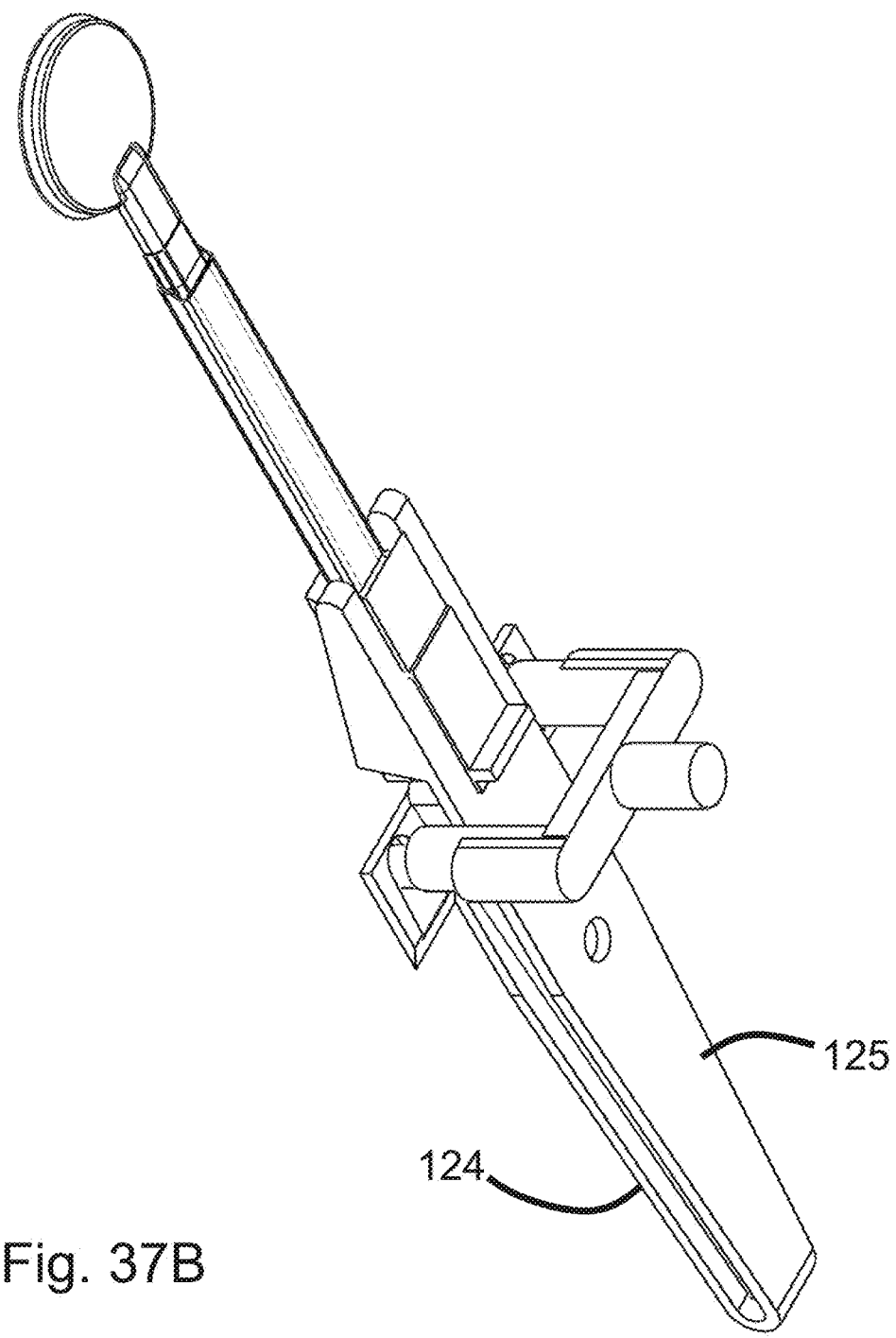
FIG. 37B illustrates a suction unit of a surgical device for performing a capsulotomy, according to an embodiment of the invention.
Figure 37C:
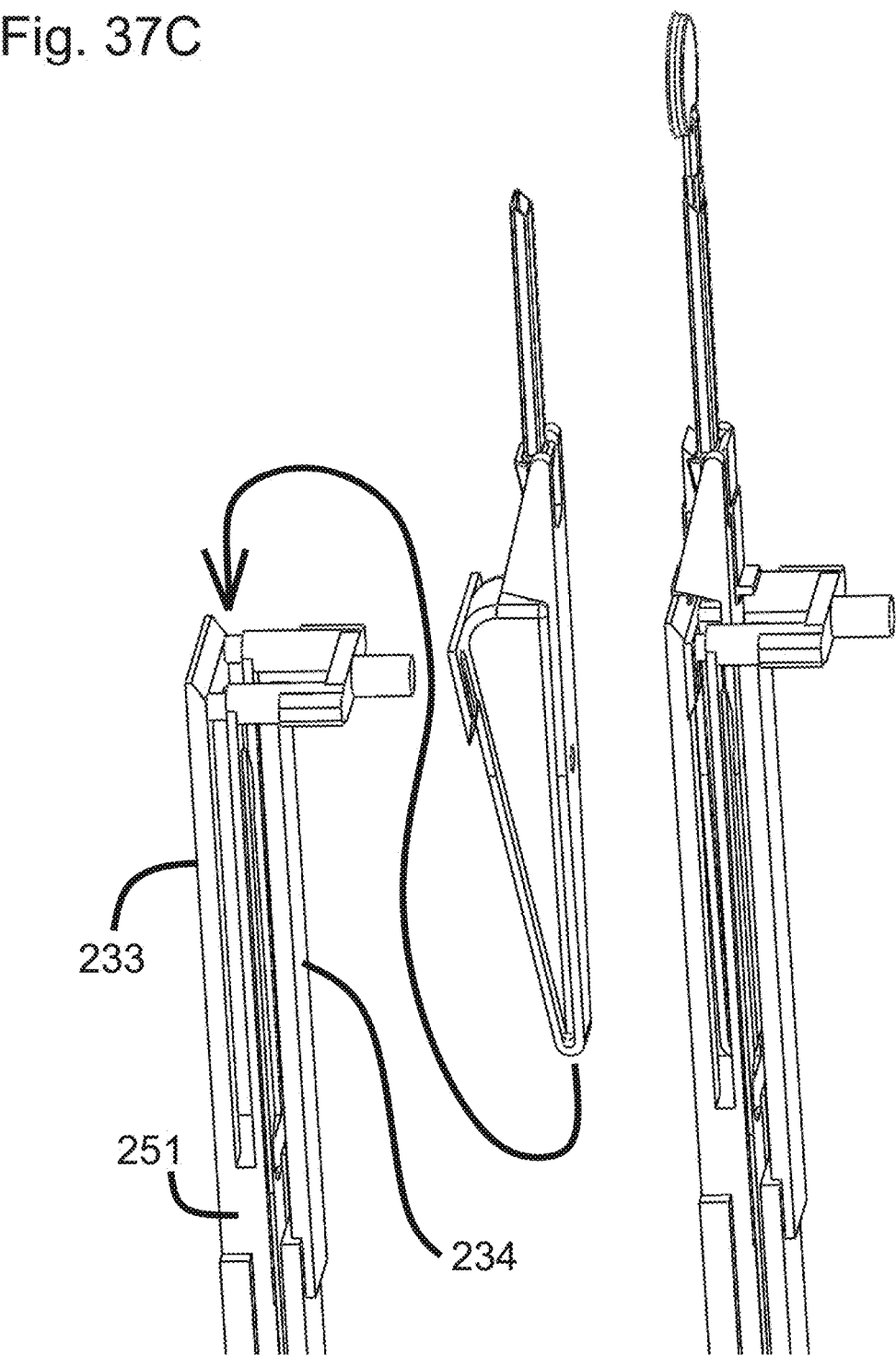
FIG. 37C illustrates a portion of a surgical device for performing a capsulotomy, according to an embodiment of the invention.

FIG. 37A shows how the knob (218) engages the sockets (240), according to one embodiment. In this embodiment, the knob is pushed down, and the suction bladder (212) is expanded to produce suction. In FIG. 37B, the knob has been released and the suction bladder is compressed again to its low volume state, according to one embodiment. FIG. 37C shows that the cavity formed by floor (233) and roof (234) which are cantilevered off block (251) compresses the suction bladder when the disposable unit is inserted into the hand piece, according to one embodiment. In a further embodiment, a sensor monitors the deflection at (206) and may be mounted on the roof (234).

Figure 37D:
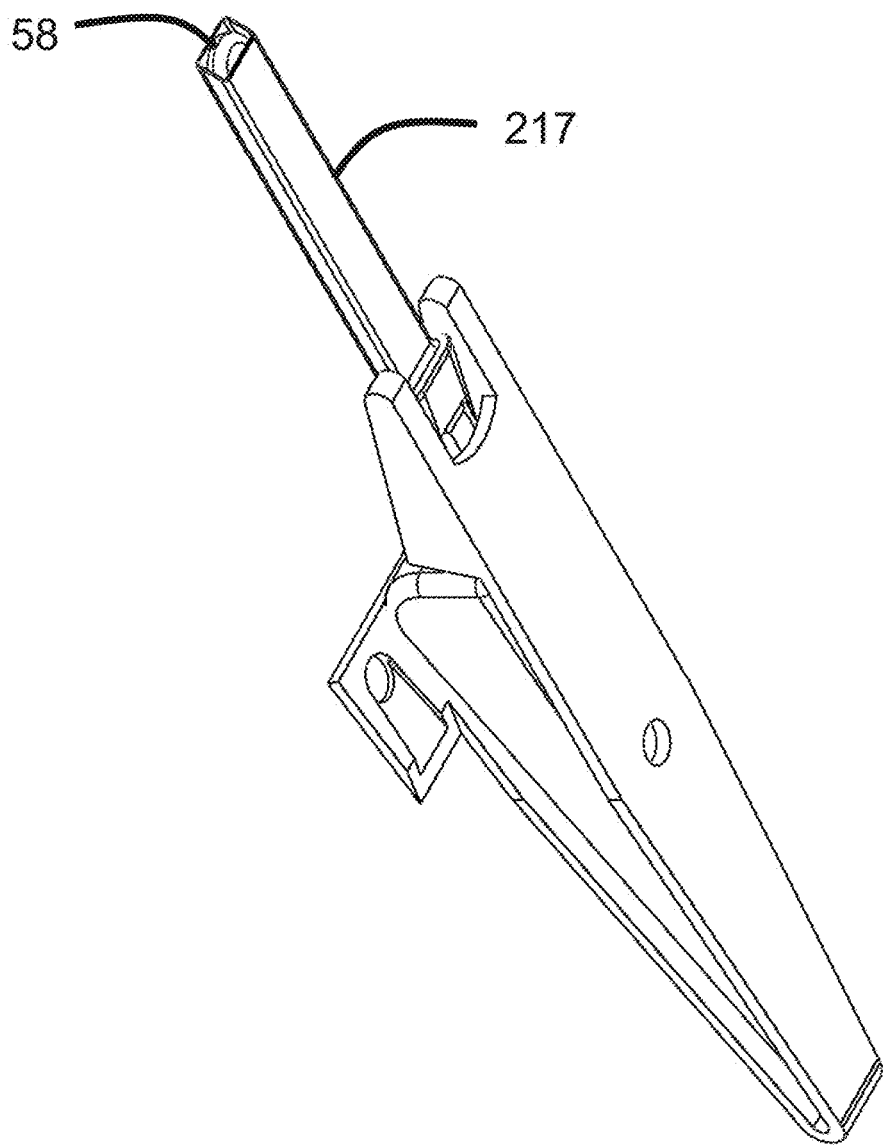
FIG. 37D illustrates a portion of a surgical device for performing a capsulotomy, according to an embodiment of the invention.
Figure 38:
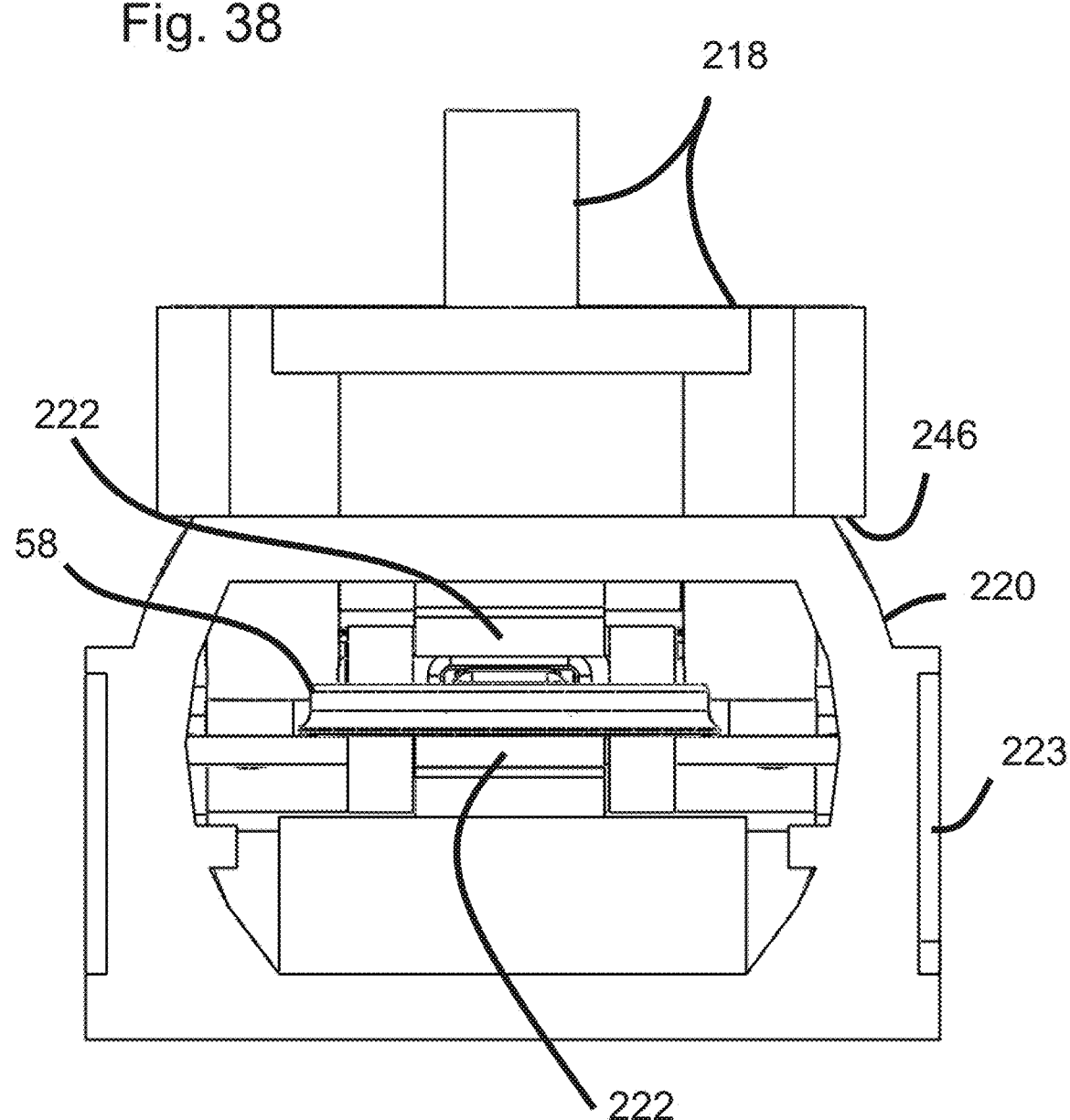
FIG. 38 illustrates a front view of a suction cup mounted to a support structure of a surgical device for performing a capsulotomy, according to an embodiment of the invention.
Figure 39:
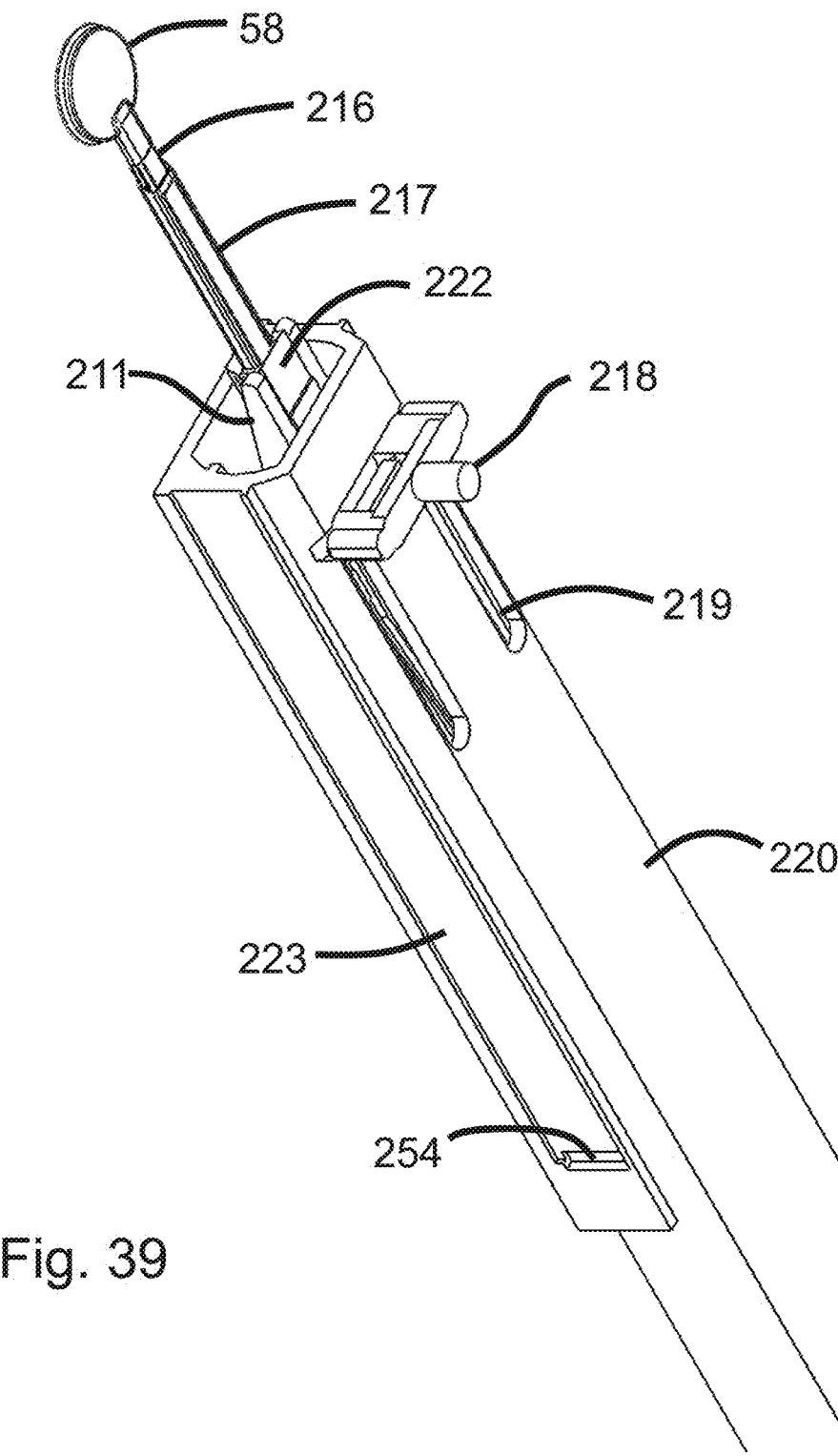
FIG. 39 illustrates a side perspective view of a suction cup mounted to a support structure of a surgical device for performing a capsulotomy, according to an embodiment of the invention.
Figure 40:
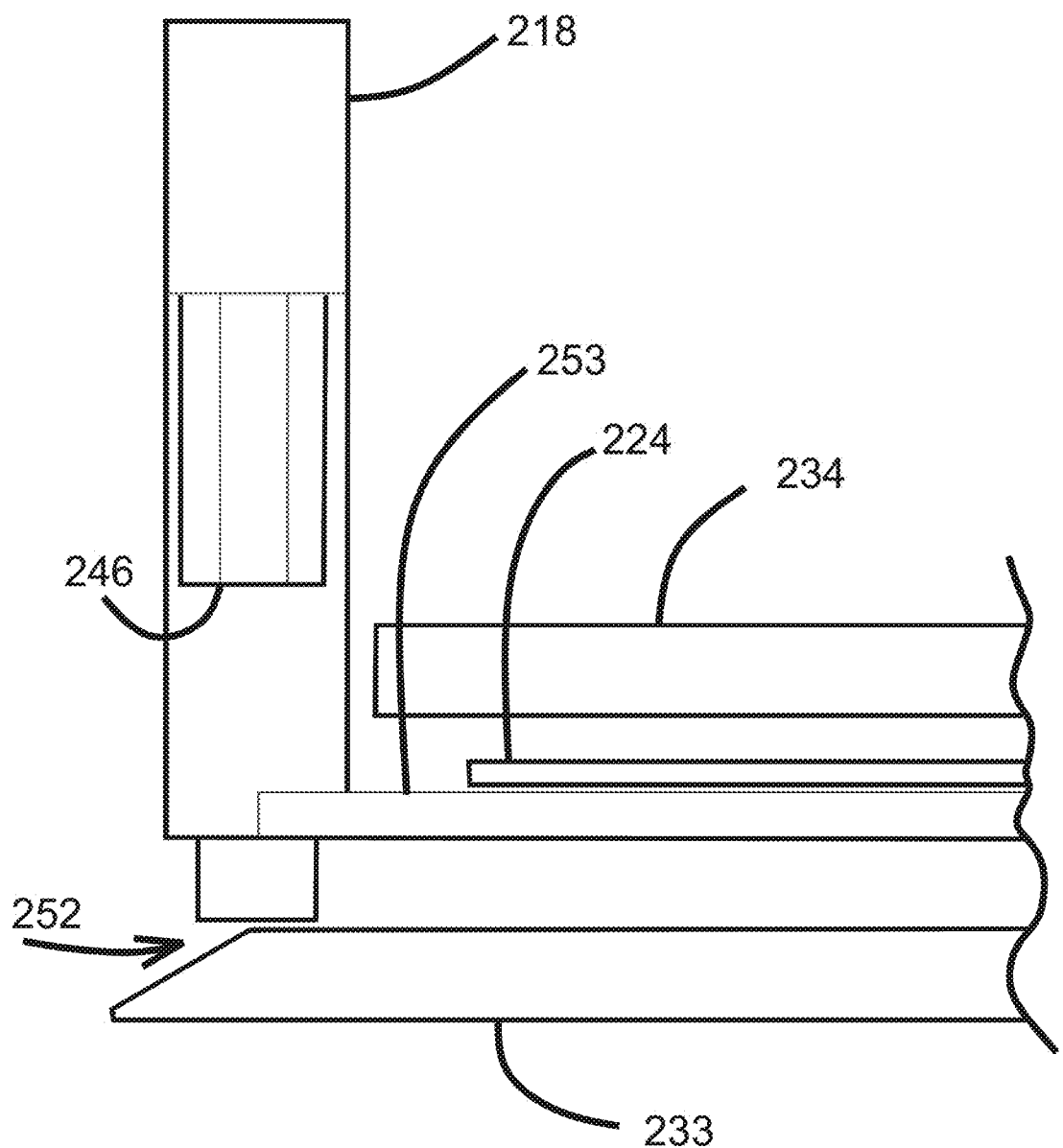
FIG. 40 illustrates a side view of a portion of a surgical device for performing a capsulotomy including a knob and cantilever, according to an embodiment of the invention.

FIG. 37D shows a configuration of the device shipped and stored with the suction cup (58) already in the inserter (217), according to one embodiment. In this embodiment, no compressor is needed. The user may simply take the unit out of its sterile package, plugs it into the hand piece, and begin using the device. FIG. 38 shows a front view of the deployed suction cup mounted in the hand piece, according to one embodiment. FIG. 39 shows a side perspective view of the deployed suction cup mounted in the hand piece, according to one embodiment. FIG. 40 shows a side view of the structure comprising the knob (218) and the cantilever (253) that connects the knob to the block (251), according to one embodiment. This embodiment includes contacts (224), roof (234), floor (233), and the converging entrance (252) that guides the insertion of ramp (226 see FIG. 37) of the disposable unit.

Figure 41:
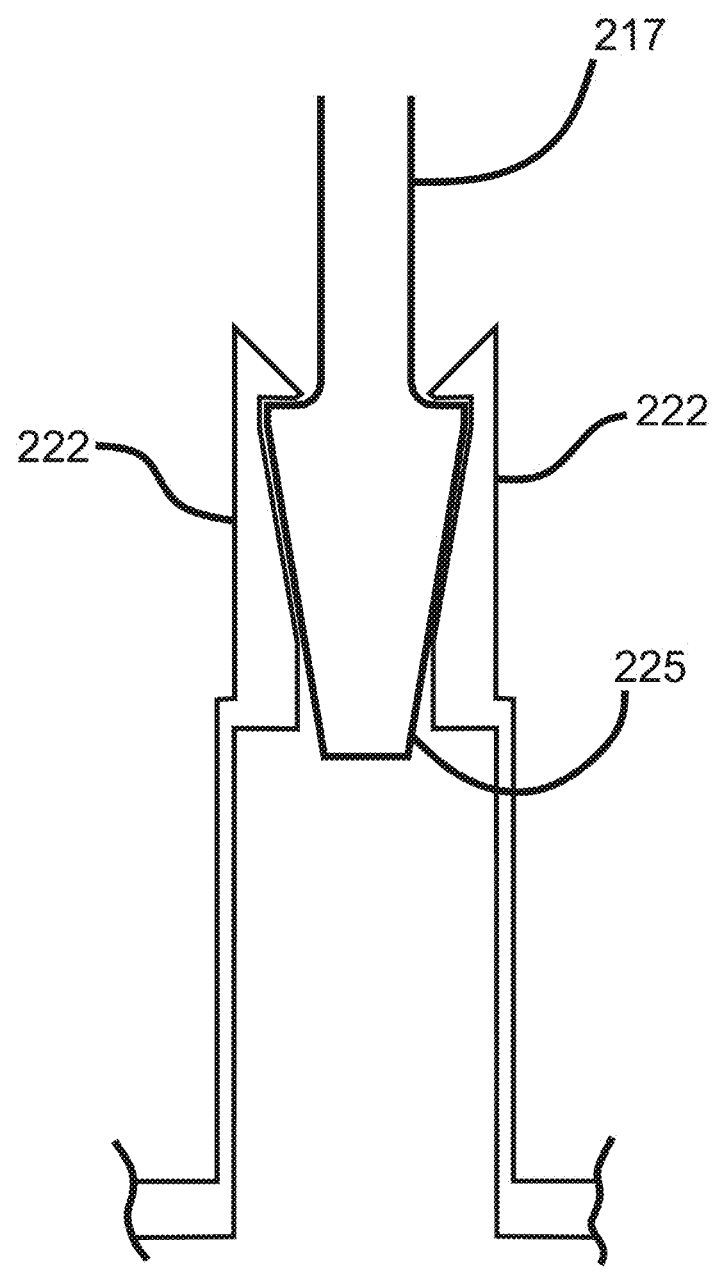
FIG. 41 illustrates a side view of a portion of a surgical device for performing a capsulotomy including a latch, according to an embodiment of the invention.
Figure 42:
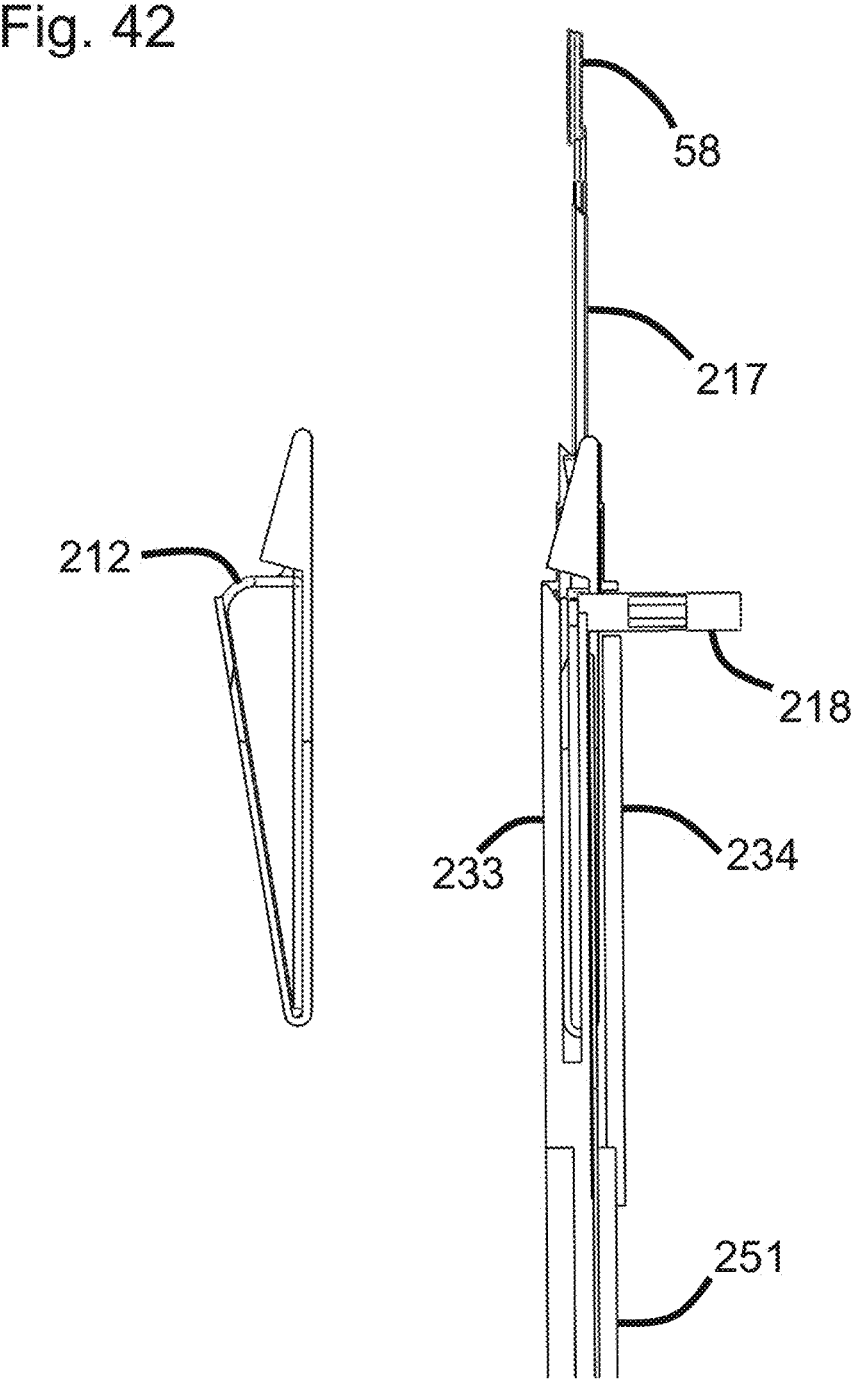
FIG. 42 illustrates a side view of a portion of a surgical device for performing a capsulotomy including a disposable bladder, according to an embodiment of the invention.
Figure 43:
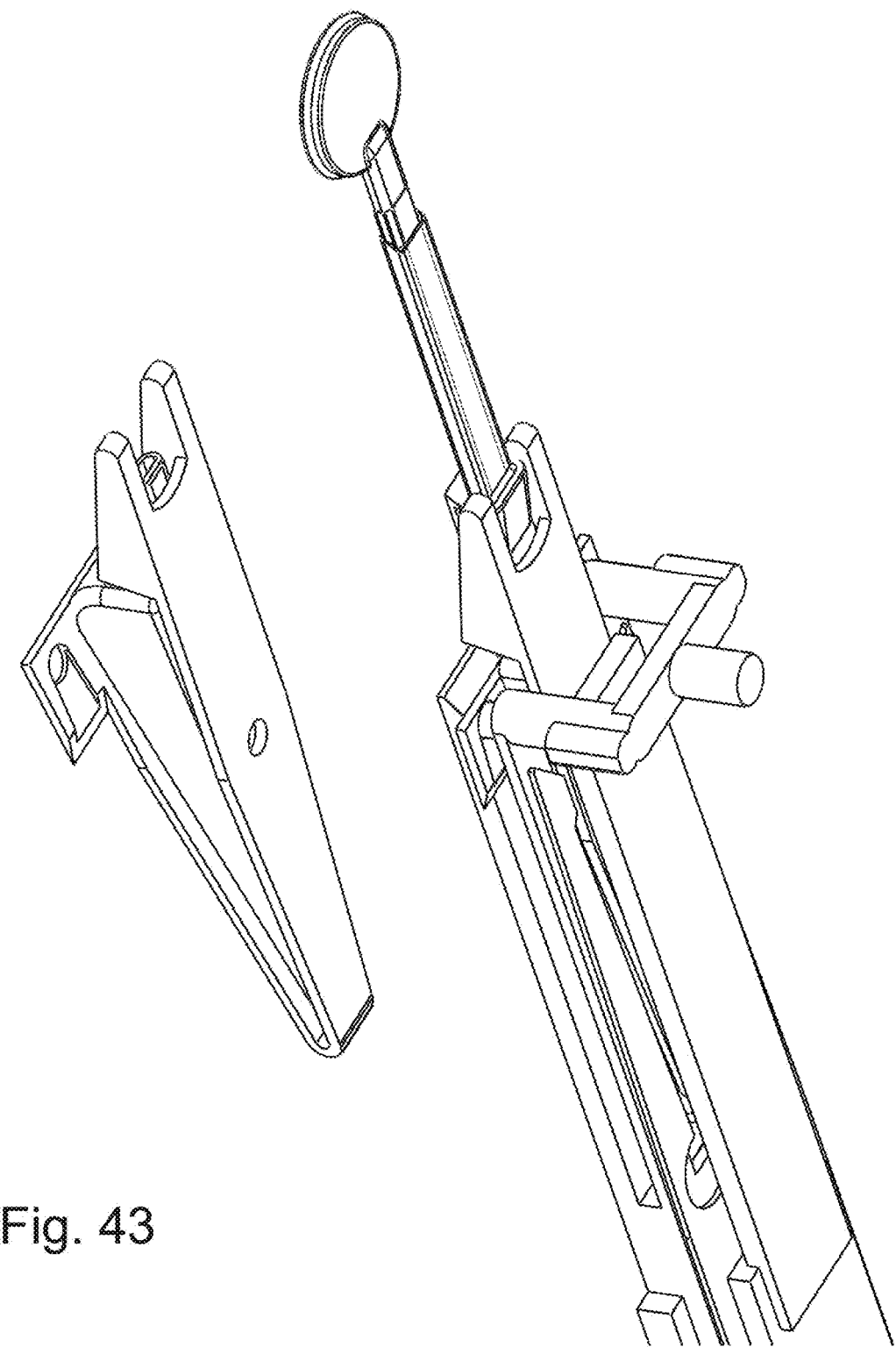
FIG. 43 illustrates an oblique perspective view of a portion of a surgical device for performing a capsulotomy including a disposable bladder, according to an embodiment of the invention.

FIG. 41 shows a side view of the inserter latching strategy, according to one embodiment. Latches (222) can be cantilevered from the handle to engage the tapered structure (225) of the disposable inserter (217) as it slides in. In an embodiment, the wedges (211 see FIG. 29) grip the inserter tightly enough to hold it during the latching step, but can slide off and back on during the subsequent steps of the device operation. FIG. 42 shows a side view with a disposable bladder (212) next to a disposable unit installed in the sliding unit with the bladder compressed, according to one embodiment. FIG. 43 shows an oblique perspective view, according to one embodiment.

Figure 44A:
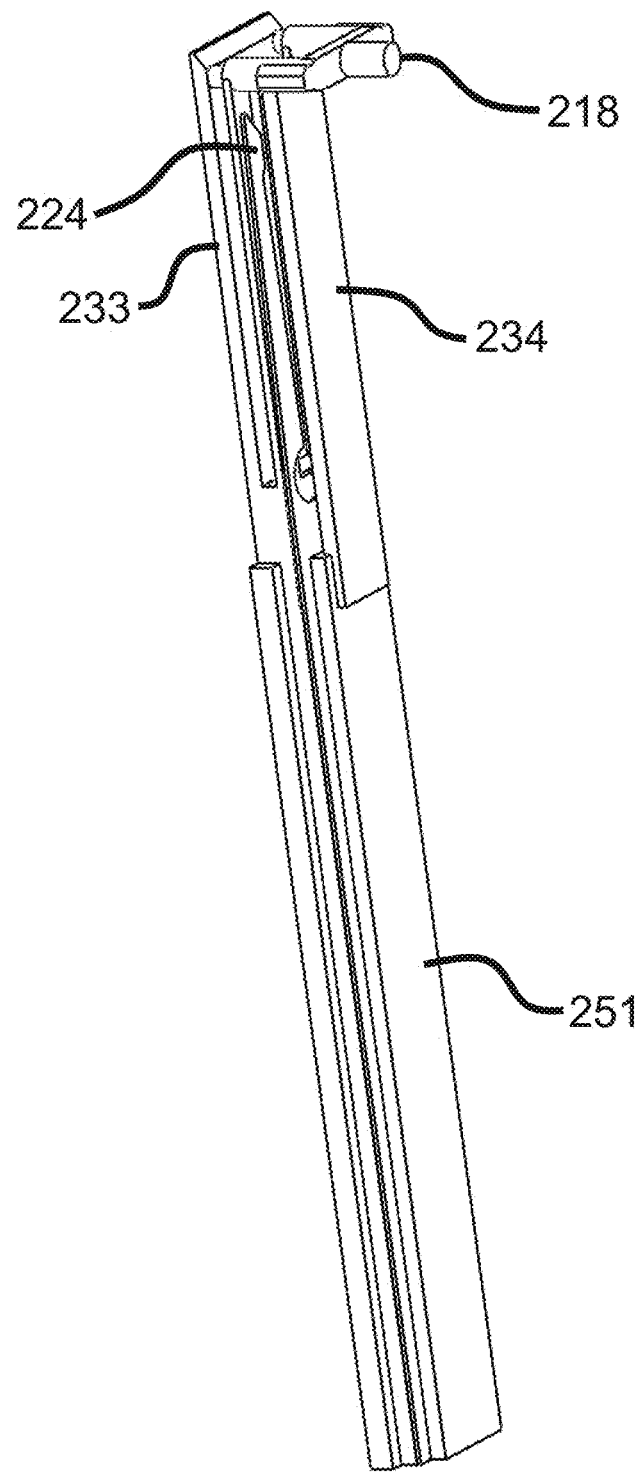
FIG. 44A illustrates a perspective overview of a sliding unit of a support structure of a surgical device for performing a capsulotomy, according to an embodiment of the invention.
Figure 44:
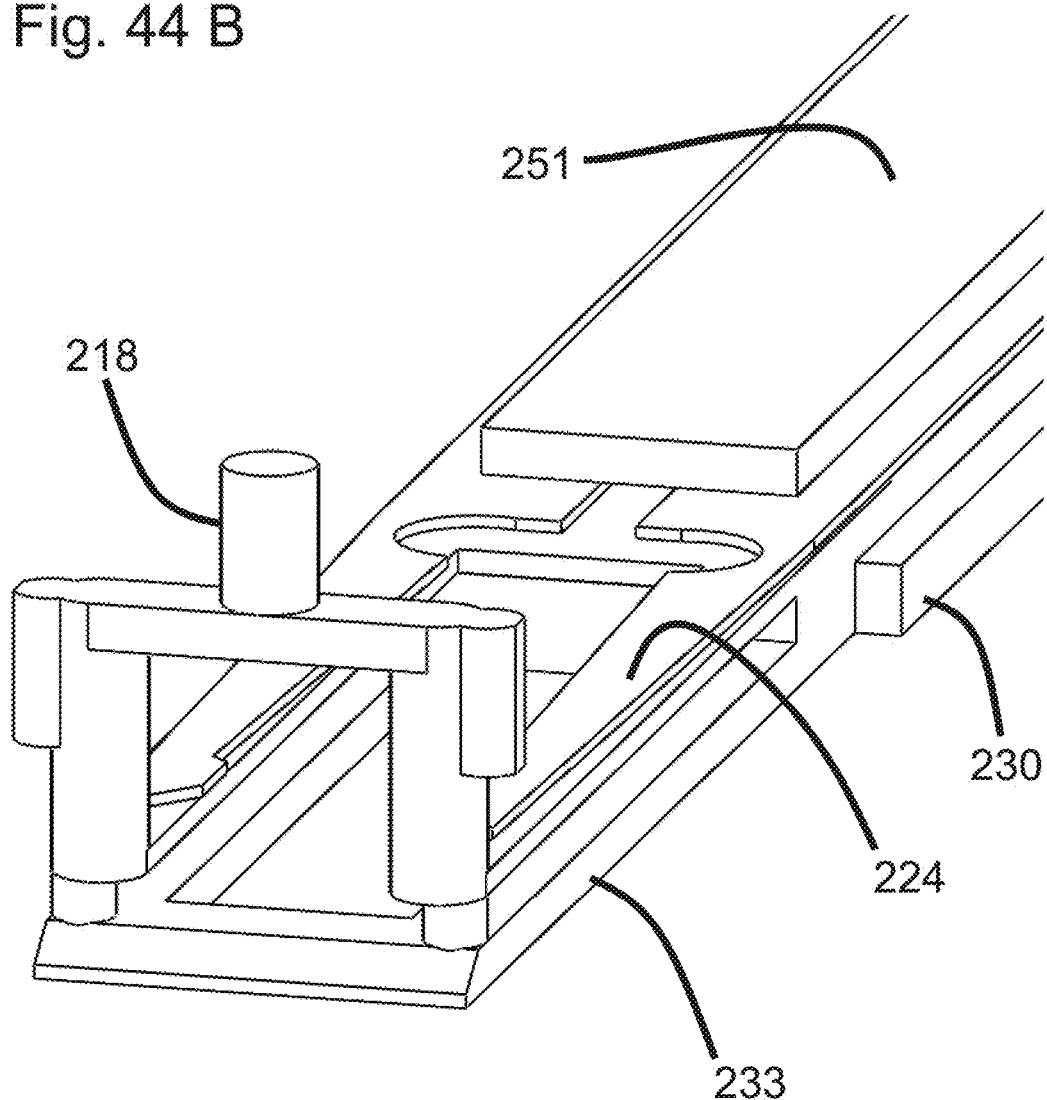
FIG. 44B illustrates a close-up view of electrical connectors of a surgical device for performing a capsulotomy, according to an embodiment of the invention.

FIG. 44A shows a perspective overview of the sliding unit of the reusable hand piece, according to one embodiment. FIG. 44B illustrates that the roof (234) has been removed to show the underlying electrical connectors (224), according to one embodiment.

Figure 45A:
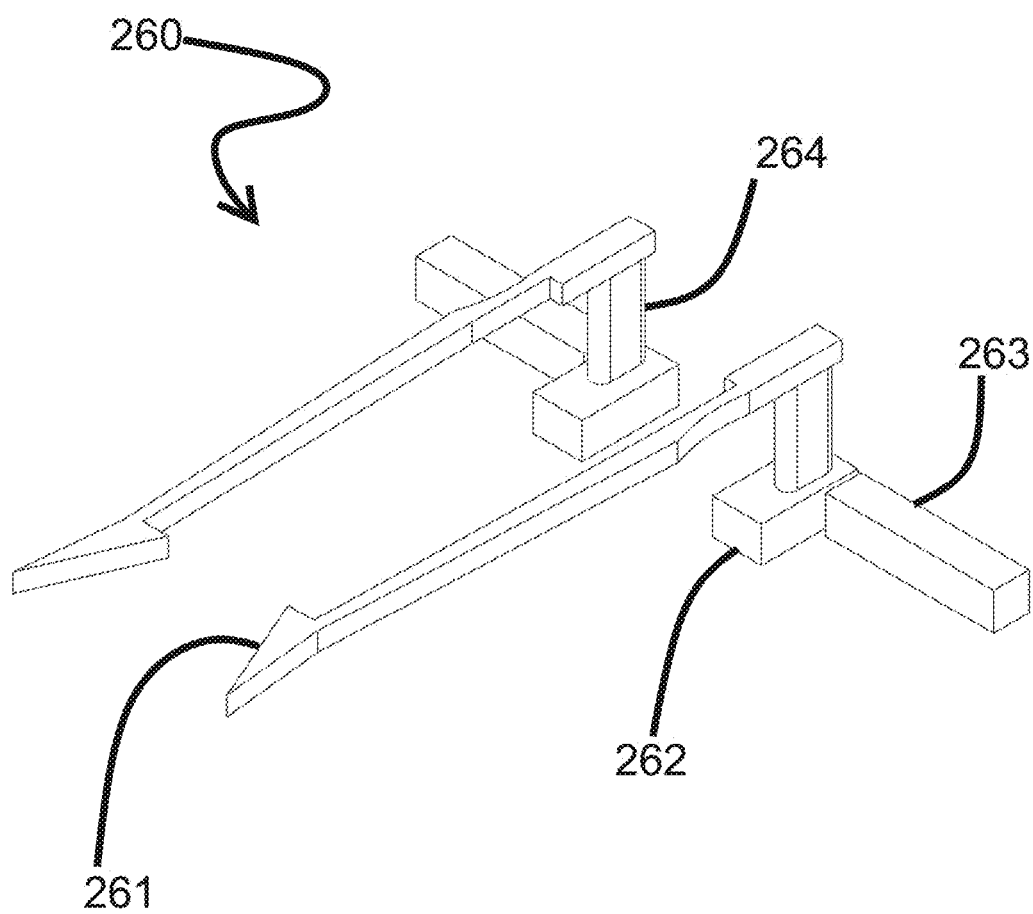
FIG. 45A illustrates a slidable latching structure of a surgical device for performing a capsulotomy, according to an embodiment of the invention.
Figure 45B:
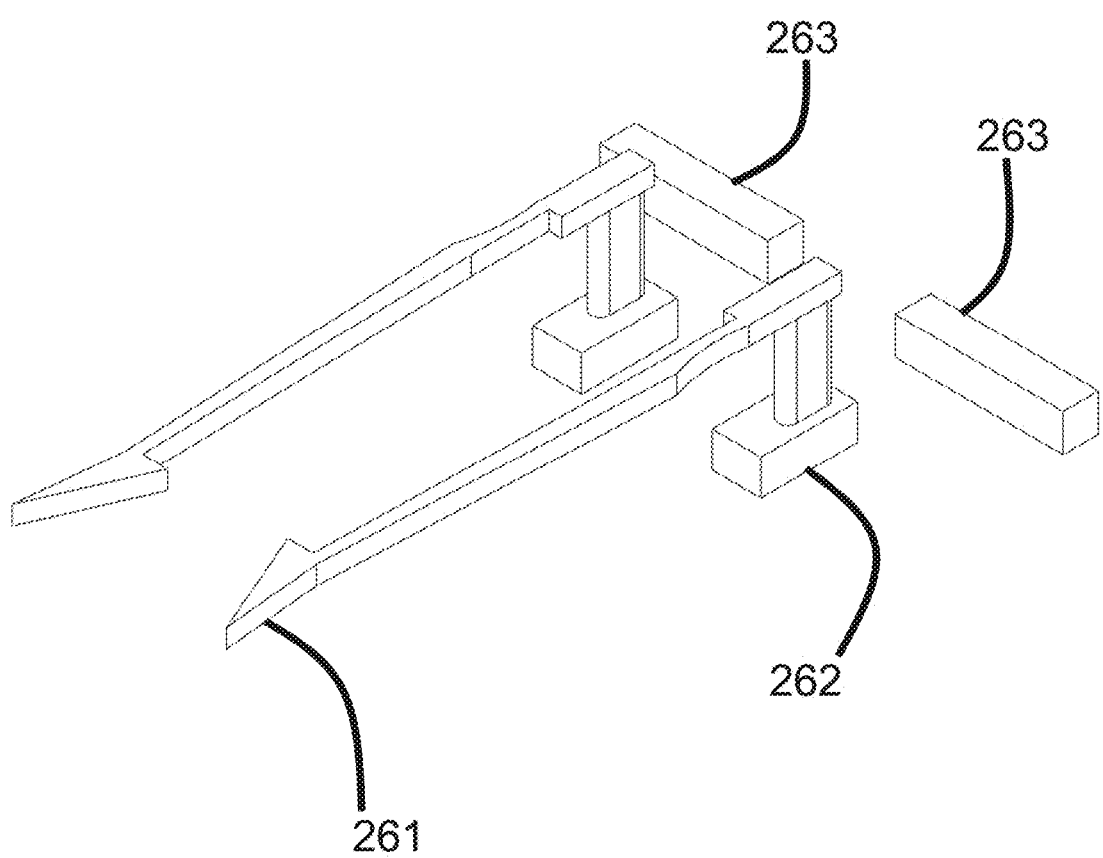
FIG. 45B illustrates a slidable latching structure of a surgical device for performing a capsulotomy, according to an embodiment of the invention.

FIGS. 45A through 47 show embodiments with latching interlocks that prevent out of sequence operation of the device. FIG. 45A shows a slidable latching structure (260) having blocks (262) that block other sliding blocks (263) from moving towards each other, according to one embodiment. Posts (264) can connect sliding blocks (262) to cantilevered latches (261) that are located above the compression chamber (201). The cantilevered latches (261) may engage the sides of the knob (218) of the reusable hand piece as the disposable unit is plugged into the hand piece. Then, when the knob is slid to its proximal position to pull the suction cup into the inserter, the blocks (262) may be pulled out of the way of sliding blocks (263) (see FIG. 45B) so that compression chamber release levers (213) can be moved to release the compression chamber from the hand piece.

Figure 46:
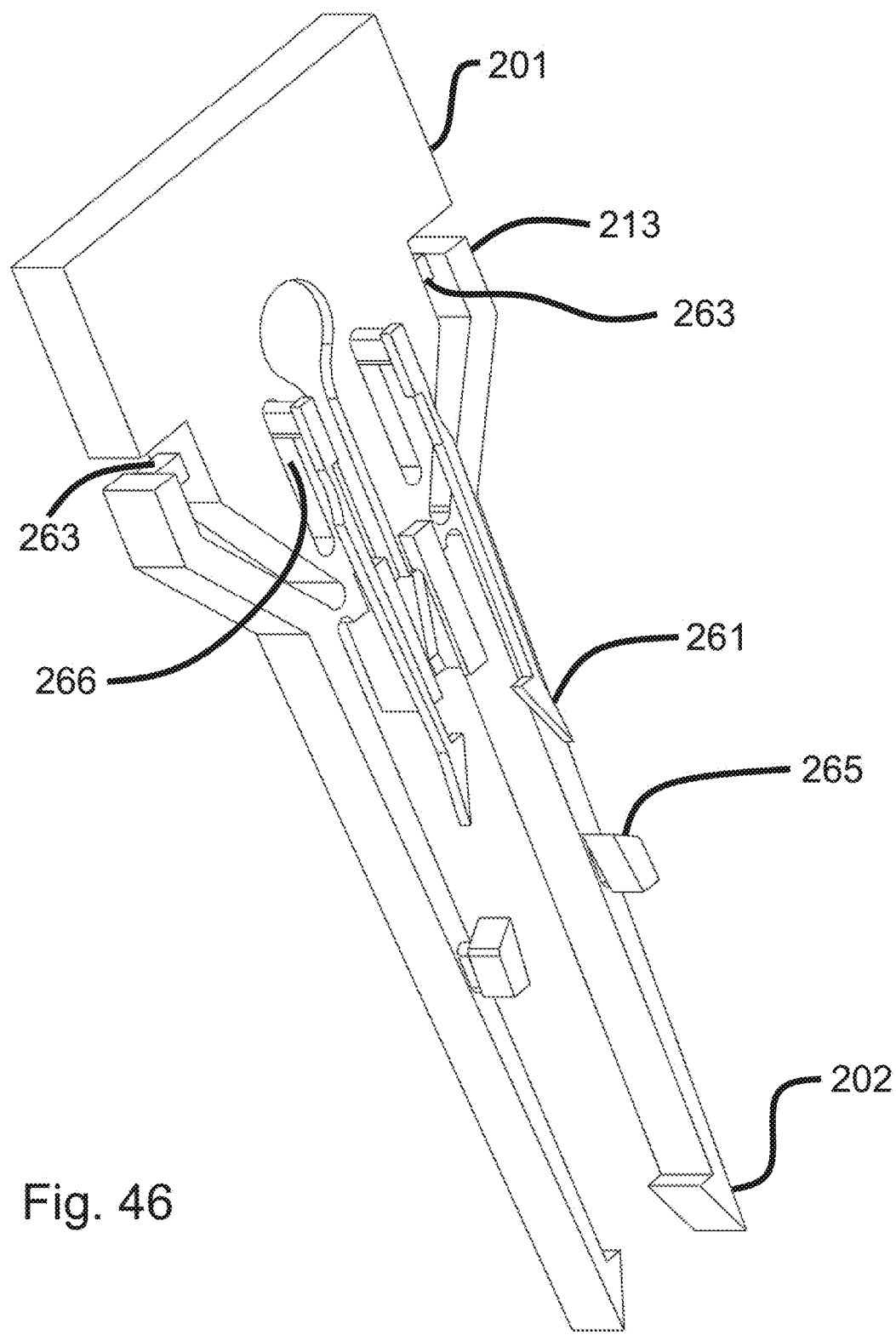
FIG. 46 illustrates a portion of a surgical device for performing a capsulotomy including a compressor, according to an embodiment of the invention.

FIG. 46 shows the compressor (201) with latches (202) that anchor it on the hand piece when the user plugs the disposable unit into the reusable hand piece, according to one embodiment. Slots (266) may retain the blocks (262 see FIGS. 45A and 45B) because the blocks (262) are too wide to fit through the slots. The blocks can slide along passageways that are within the body of the compressor.

Figure 47:
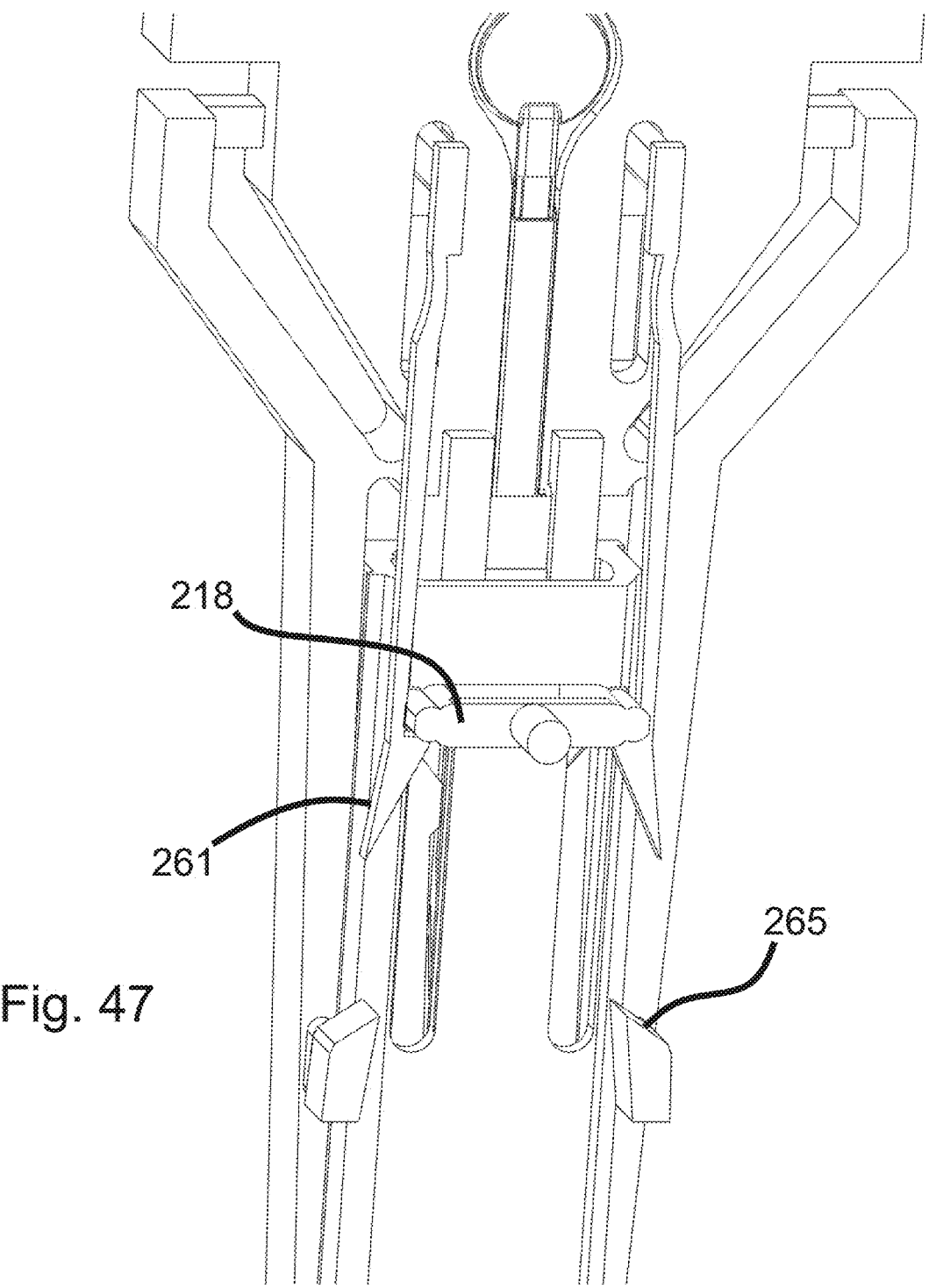
FIG. 47 illustrates a portion of a surgical device for performing a capsulotomy including a disposable unit, according to an embodiment of the invention.

FIG. 47 shows the disposable unit as it is first plugged into the reusable hand piece, according to one embodiment. In this embodiment, latches (261) have gripped the knob (218) of the hand piece. When a user slides the knob to its proximal position to pull the suction cup into the inserter, the latches (261) will also move. In a further embodiment, since the latches (261) are connected to blocks (262) they will slide out of the way of blocks (263) so they in turn can slide towards the centerline when release levers (213) are pushed. As the latches (261) reach the end of their slide towards the proximal position, they come into contact with wedges (265) so that when release levers (213) are pressed towards the centerline to make latches (202) swing away from the centerline, the wedges (265) will push the latches (261) away from the centerline. Thus, the latches (261) become disengaged from the knob (218) and have clearance to slide past the knob when the compressor is pulled away from the handle. The purpose of this interlock is to prevent the compressor from being pulled off the hand piece until after the suction cup has been pulled into the inserter.

Summary

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

All references, issued patents and patent applications cited within the body of the instant specification are hereby incorporated by reference in their entirety, for all purposes.

What is claimed is:

1. A surgical device for tissue cutting, the device comprising:
   a reversibly collapsible supporting element; and
   a reversibly collapsible cutting element attached to the supporting element, the cutting element comprising:
      an electrically conductive outer layer on an outer diameter of the supporting element, the electrically conductive outer layer having a first thickness,
      an electrically conductive inner layer on an inner diameter of the supporting element, the electrically conductive inner layer having the first thickness, and
      a bottom layer on a bottom edge of the supporting element, the bottom layer having a second thickness, wherein the first thickness is thicker than the second thickness, the bottom layer configured to conduct an electrical current between the electrically conductive outer layer and the electrically conductive inner layer;
      wherein the inner layer, the outer layer and the bottom layer comprise an insulator configured to couple to the supporting element and to insulate the inner layer, the outer layer, and the bottom layer from the supporting element; and
      wherein a first lead is coupled to the outer layer and a second lead is coupled to the inner layer such that current is configured to flow between the first lead and the second lead through the outer layer, the bottom layer, and the inner layer.

2. The surgical device of claim 1, wherein the cutting element is circular in shape.

3. The surgical device of claim 1, further comprising a suction cup attached to the supporting element.

4. The surgical device of claim 1, wherein the bottom layer has a thickness of 10-200 angstroms.

5. The surgical device of claim 1, wherein the cutting element is configured for the current to flow as (1) a single electrical current pulse, or (2) a series of electrical current pulses.

6. The surgical device of claim 1, wherein (1) the outer layer is coupled to a first lead, the first lead configured to conduct the electrical current to the outer layer and to the bottom layer, and wherein (2) the inner layer is coupled to a second lead, the inner layer configured to conduct the electrical current from the bottom layer to the second lead.

7. The surgical device of claim 1, wherein the supporting element is composed of an elastic material, and is coated with an insulating layer, and wherein the outer layer, the inner layer, and the bottom layer are coated over the insulating layer.

8. The surgical device of claim 1, wherein each of the inner and outer layers comprise a plurality of layers including a layer of a first metal and a layer of a second metal, wherein one of the plurality of layers is thinner and of a higher resistance than another of the layers.

9. The surgical device of claim 1, wherein the supporting element comprises nitinol and wherein the electrically conductive inner layer and the electrically conductive outer layer comprise one or more of: a tantalum layer coated with a tantalum oxide layer coated with a second tantalum layer and a gold layer coated over the second tantalum layer.

10. The surgical device of claim 1, wherein the supporting element has a thickness of 25-50 microns at a portion of the supporting element between the outer layer and the inner layer.

11. The surgical device of claim 1, wherein the supporting element is composed of elastic material.

12. The surgical device of claim 11, wherein at least a portion of the supporting element is coated with an adhesion material.

13. The surgical device of claim 12, wherein at least a portion of the adhesion material of the supporting element is coated with a diffusion barrier material.

14. The surgical device of claim 1, wherein the device comprises a capsulotomy device for performing a capsulotomy on a lens capsule of an eye.

15. A surgical device for cutting tissue, the device comprising:
   a reversibly collapsible supporting element;
   a reversibly collapsible cutting element attached to the supporting element, the cutting element comprising an electrically conductive surface layer on a surface of the supporting element, wherein the electrically conductive surface layer is configured to conduct an electrical current that causes a temperature increase in the electrically conductive surface layer for cutting the tissue and;
   wherein the electrically conductive surface layer comprises a tantalum layer coated with a tantalum oxide layer coated with a second tantalum layer configured to couple to the supporting element and to insulate the electrically conductive surface layer from the supporting element; and
   wherein current is configured to flow between a first lead and a second lead through the electrically conductive surface layer.

16. The surgical device of claim 15, wherein the electrically conductive surface layer is an electrically conductive outer layer on an outer diameter of the supporting element.

17. The surgical device of claim 15, wherein the electrically conductive surface layer is an electrically conductive inner layer on an inner diameter of the supporting element.

18. The surgical device of claim 15, further comprising a suction cup attached to the supporting element.

* * * * *